US007718846B2

(12) United States Patent
Koren et al.

(10) Patent No.: US 7,718,846 B2
(45) Date of Patent: May 18, 2010

(54) ANIMAL MODELS OF LONG QT SYNDROME AND USES THEREOF

(76) Inventors: Gideon Koren, 64 Blake Rd., Brookline, MA (US) 02446; Xuwen Peng, 270 Jacobs Creek Dr., Hershey, PA (US) 17033; Rajesh Mathur, 5-6395 Hawthorn Lane, Vancouver British Columbia (CA) V6T 1Z4; Manfred Zahender, Längenhardtstraβe 12, Freiburg (DE) 79104

( * ) Notice: Subject to any disclaimer, the term of this patent is extended or adjusted under 35 U.S.C. 154(b) by 314 days.

(21) Appl. No.: 11/130,031

(22) Filed: May 16, 2005

(65) Prior Publication Data

US 2006/0259992 A1 Nov. 16, 2006

(51) Int. Cl.

| | |
|---|---|
| ***A01K 67/027*** | (2006.01) |
| ***C12N 15/00*** | (2006.01) |
| ***C12N 5/00*** | (2006.01) |
| ***A01K 67/00*** | (2006.01) |

(52) U.S. Cl. ............................ 800/14; 800/13; 800/21; 800/25; 435/325

(58) Field of Classification Search ..................... 800/9, 800/8, 21, 14, 13, 25; 435/325
See application file for complete search history.

(56) References Cited

OTHER PUBLICATIONS

Wolf et al, Experimental Physiology, 85(6): 615-625, 2000.*
Smith Journal of Biotechnology, 99: 1-22, 2002.*
Hoppe et al, PNAS, 98(9): 5335-5340, 2001.*
Demolombe et al, Cardiovascular Research, 50: 314-327, 2001.*
Fan et al, Pharmacology & Therapeutics, 99: 261-282, 2003.*
Hong et al, Cardiovascular Research, 68: 433-440, 2005.*
Priori, Circ Res, 94: 140-145, 2004.*
Cowan et al. 2003, Xenotransplantation, 10: 223-231.*
Wang et al (Nature Genetics, 12: 17-23, 1996.*
Babij et al, (Circ Res, 83: 668-678, 1998.*
Tanaka et al (Circulation, 95: 565-567, 1997.*

* cited by examiner

*Primary Examiner*—Anne-Maria Falk
*Assistant Examiner*—Magdalene K Sgagias
(74) *Attorney, Agent, or Firm*—Foley Hoag LLP

(57) ABSTRACT

Provided are animal models of long QT syndrome (LQTS). The animal models are useful, for example, in screening of drugs for adverse effects in subjects with LQTS, in screening candidate therapeutics for the treatment or prevention of LQTS, and in determining gene expression in LQTS.

4 Claims, 16 Drawing Sheets

FIGURE 1

Genetic Background of Inherited Forms of LQTS (Romano-Ward Syndrome)

| LQTS Type | Chromosomal Locus | Mutated Gene | Ion Current Affected |
|---|---|---|---|
| LQT1 | 11p15.5 | *KVLQT1* (*KCNQ1*) (heterozygotes) | Potassium current ($I_{Ks}$) |
| LQT2 | 7q35-36 | *HERG* | Potassium current ($I_{Kr}$) |
| LQT3 | 3p21-24 | *SCN5A* | Sodium current ($I_{Na}$) |
| LQT4 | 4q25-27 | Ankyrin B | |
| LQT5 | 21q22.1-22.2 | *KCNE1* (heterozygotes) | Potassium current ($I_{Ks}$) |
| LQT6 | 21q22.1-22.2 | *MiRP1* | Potassium current ($I_{Kr}$) |
| LQT7 | 17q23.1-q24.2 | *Kir2.1* *KCNJ2* | Potassium current |

FIGURE 2

Genetic Background of Inherited Forms of LQTS (Jervell and Lang-Nielsen Syndrome)

| LQTS Type | Chromosomal Locus | Mutated Gene | Ion Current Affected |
|---|---|---|---|
| JLN1 | 11p15.5 | *KVLQT1* (*KCNQ1*) (homozygotes) | Potassium current ($I_{Ks}$) |
| JLN2 | 21q22.1-22.2 | *KCNE1* (homozygotes) | Potassium current ($I_{Ks}$) |

TRANSGENIC DOMINANT NEGATIVE FL-HERG G628S SUBUNIT IN RABBIT BETA MHC PROMOTER VECTOR CONSTRUCT

Transgenic construct of FLAG-KvLQT1 Y315S $K^+$ Channel Subunit, Downstream of the Rabbit Cardiac β-MHC Promoter

FIGURE 5
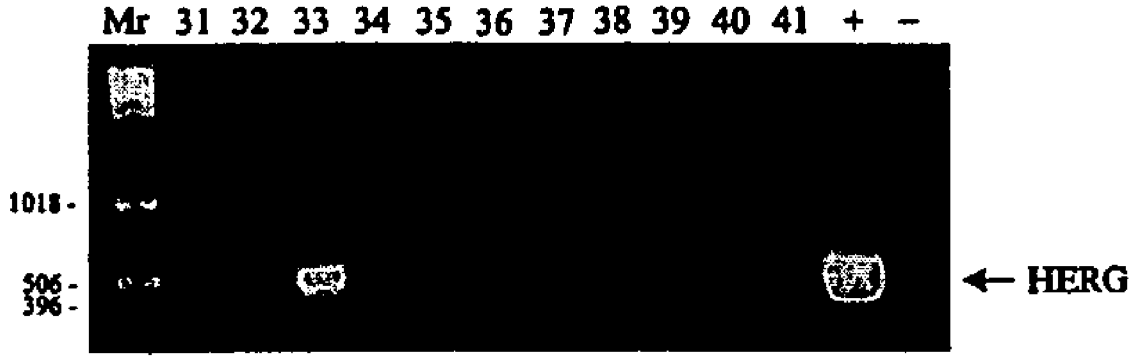
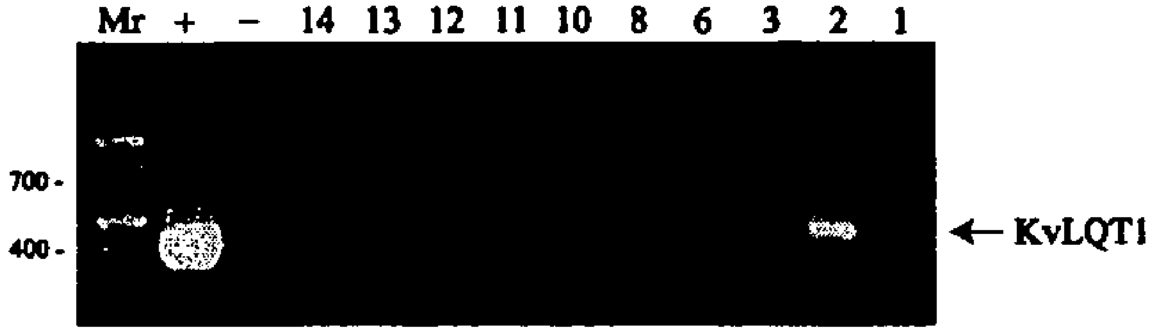

FIGURE 9
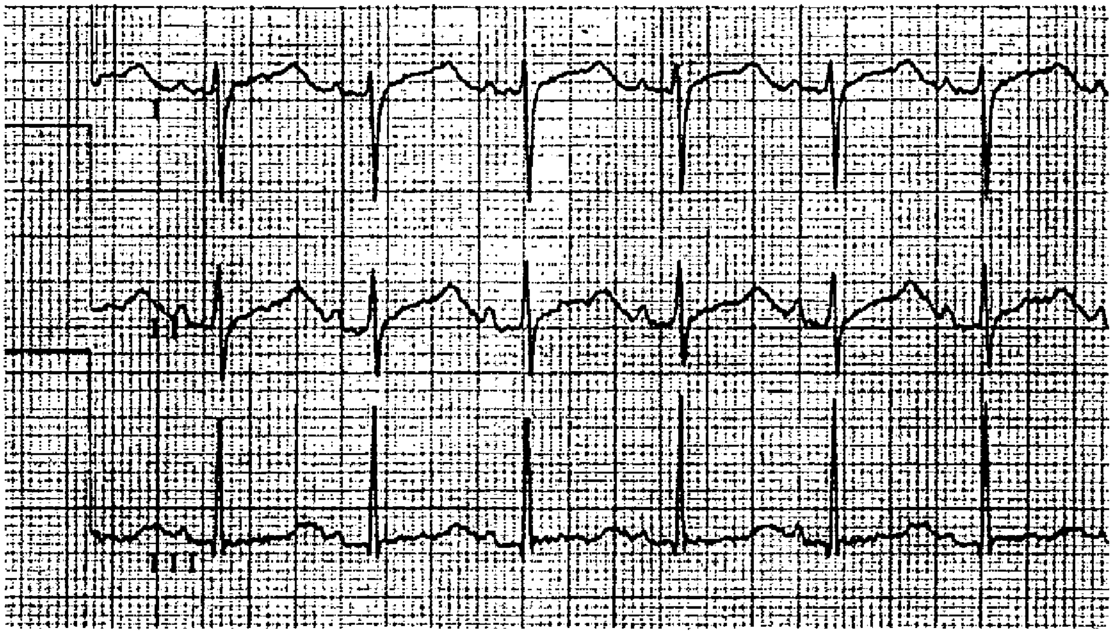
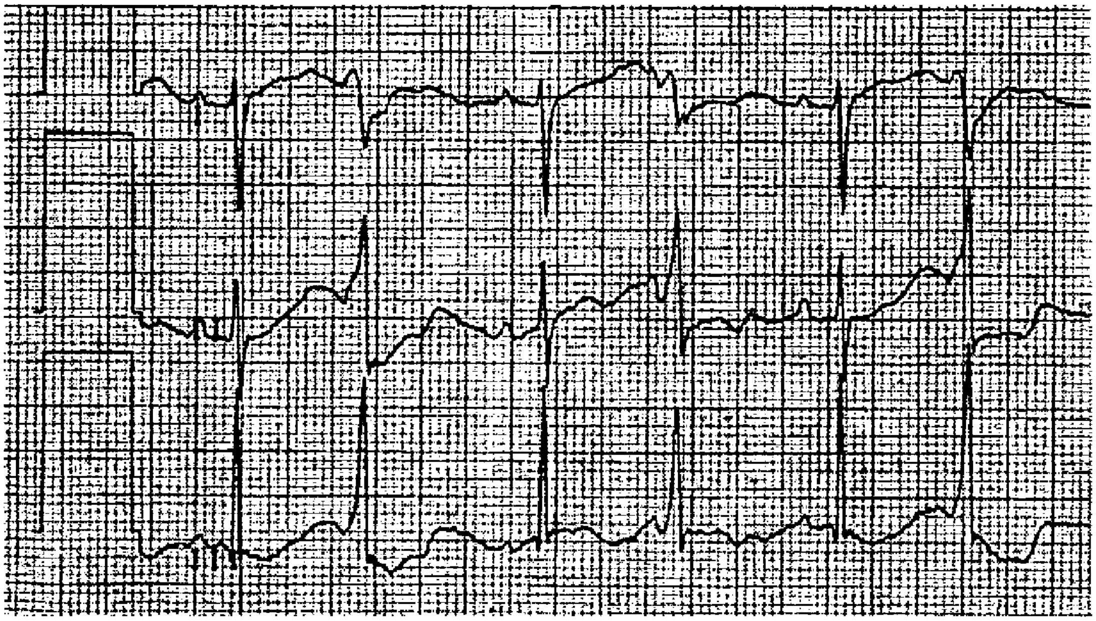

FIGURE 15

KvLQT1 (SEQ ID NO:1)

GGGCGGCGGGGCTGGCAGCAGTGGCTGCCCGCACTGCGCCCGGGCGCTCGCCTTCGCTGCAGCTCCCGGT
GCCGCCGCTCGGGCCGGCCCCCCGGCAGGCCCTCCTCGTTATGGCCGCGGCCTCCTCCCCGCCCAGGGCC
GAGAGGAAGCGCTGGGGTTGGGGCCGCCTGCCAGGCGCCCGGCGGGGCAGCGCGGGCCTGGCCAAGAAGT
GCCCCTTCTCGCTGGAGCTGGCGGAGGGCGGCCCGGCGGGCGGCGCGCTCTACGCGCCCATCGCGCCCGG
CGCCCCAGGTCCCGCGCCCCCTGCGTCCCCGGCCGCGCCCGCCGCGCCCCCAGTTGCCTCCGACCTTGGC
CCGCGGCCGCCGGTGAGCCTAGACCCGCGCGTCTCCATTTACAGCACGCGCCGCCCGGTGTTGGCGCGCA
CCCACGTCCAGGGCCGCGTCTACAACTTCCTCGAGCGTCCCACCGGCTGGAAATGCTTCGTTTACCACTT
CGCCGTCTTCCTCATCGTCCTGGTCTGCCTCATCTTCAGCGTGCTGTCCACCATCGAGCAGTATGCCGCC
CTGGCCACGGGGACTCTCTTCTGGATGGAGATCGTGCTGGTGGTGTTCTTCGGGACGGAGTACGTGGTCC
GCCTCTGGTCCGCCGGCTGCCGCAGCAAGTACGTGGGCCTCTGGGGGCGGCTGCGCTTTGCCCGGAAGCC
CATTTCCATCATCGACCTCATCGTGGTCGTGGCCTCCATGGTGGTCCTCTGCGTGGGCTCCAAGGGGCAG
GTGTTTGCCACGTCGGCCATCAGGGGCATCCGCTTCCTGCAGATCCTGAGGATGCTACACGTCGACCGCC
AGGGAGGCACCTGGAGGCTCCTGGGCTCCGTGGTCTTCATCCACCGCCAGGAGCTGATAACCACCCTGTA
CATCGGCTTCCTGGGCCTCATCTTCTCCTCGTACTTTGTGTACCTGGCTGAGAAGGACGCGGTGAACGAG
TCAGGCCGCGTGGAGTTCGGCAGCTACGCAGATGCGCTGTGGTGGGGGGTGGTCACAGTCACCACCATCG
GCTATGGGGACAAGGTGCCCCAGACGTGGGTCGGGAAGACCATCGCCTCCTGCTTCTCTGTCTTTGCCAT
CTCCTTCTTTGCGCTCCCAGCGGGGATTCTTGGCTCGGGGTTTGCCCTGAAGGTGCAGCAGAAGCAGAGG
CAGAAGCACTTCAACCGGCAGATCCCGGCGGCAGCCTCACTCATTCAGACCGCATGGAGGTGCTATGCTG
CCGAGAACCCCGACTCCTCCACCTGGAAGATCTACATCCGGAAGGCCCCCCGGAGCCACACTCTGCTGTC
ACCCAGCCCCAAACCCAAGAAGTCTGTGGTGGTAAAGAAAAAAAAGTTCAAGCTGGACAAAGACAATGGG
GTGACTCCTGGAGAGAAGATGCTCACAGTCCCCCATATCACGTGCGACCCCCCAGAAGAGCGGCGGCTGG
ACCACTTCTCTGTCGACGGCTATGACAGTTCTGTAAGGAAGAGCCCAACACTGCTGGAAGTGAGCATGCC
CCATTTCATGAGAACCAACAGCTTCGCCGAGGACCTGGACCTGGAAGGGGAGACTCTGCTGACACCCATC
ACCCACATCTCACAGCTGCGGGAACACCATCGGGCCACCATTAAGGTCATTCGACGCATGCAGTACTTTG
TGGCCAAGAAGAAATTCCAGCAAGCGCGGAAGCCTTACGATGTGCGGGACGTCATTGAGCAGTACTCGCA
GGGCCACCTCAACCTCATGGTGCGCATCAAGGAGCTGCAGAGGAGGCTGGACCAGTCCATTGGGAAGCCC
TCACTGTTCATCTCCGTCTCAGAAAAGAGCAAGGATCGCGGCAGCAACACGATCGGCGCCCGCCTGAACC
GAGTAGAAGACAAGGTGACGCAGCTGGACCAGAGGCTGGCACTCATCACCGACATGCTTCACCAGCTGCT
CTCCTTGCACGGTGGCAGCACCCCCGGCAGCGGCGGCCCCCCCAGAGAGGGCGGGGCCCACATCACCCAG
CCCTGCGGCAGTGGCGGCTCCGTCGACCCTGAGCTCTTCCTGCCCAGCAACACCCTGCCCACCTACGAGC
AGCTGACCGTGCCCAGGAGGGGCCCCGATGAGGGGTCCTGAGGAGGGGATGGGGCTGGGGGATGGGCCTG
AGTGAGAGGGGAGGCCAAGAGTGGCCCCACCTGGCCCTCTCTGAAGGAGGCCACCTCCTAAAAGGCCCAG
AGAGAAGAGCCCCACTCTCAGAGGCCCCAATACCCCATGGACCATGCTGTCTGGCACAGCCTGCACTTGG
GGGCTCAGCAAGGCCACCTCTTCCTGGCCGGTGTGGGGGCCCCGTCTCAGGTCTGAGTTGTTACCCCAAG
CGCCCTGGCCCCCACATGGTGATGTTGACATCACTGGCATGGTGGTTGGGACCCAGTGGCAGGGCACAGG
GCCTGGCCCATGTATGGCCAGGAAGTAGCACAGGCTGAGTGCAGGCCCACCCTGCTTGGCCCAGGGGGCT
TCCTGAGGGGAGACAGAGCAACCCCTGGACCCCAGCCTCAAATCCAGGACCCTGCCAGGCACAGGCAGGG
CAGGACCAGCCCACGCTGACTACAGGGCCACCGGCAATAAAAGCCCAGGAGCCCATTTGGAGGGCCTGGG
CCTGGCTCCCTCACTCTCAGGAAATGCTGACCCATGGGCAGGAGACTGTGGAGACTGCTCCTGAGCCCCC
AGCTTCCAGCAGGAGGGACAGTCTCACCATTTCCCCAGGGCACGTGGTTGAGTGGGGGAACGCCCACTT
CCCTGGGTTAGACTGCCAGCTCTTCCTAGCTGGAGAGGAGCCCTGCCTCTCCGCCCCTGAGCCCACTGTG
CGTGGGGCTCCCGCCTCCAACCCCTCGCCCAGTCCCAGCAGCCAGCCAAACACACAGAAGGGGACTGCCA
CCTCCCCTTGCCAGCTGCTGAGCCGCAGAGAAGTGACGGTTCCTACACAGGACAGGGGTTCCTTCTGGGC
ATTACATCGCATAGAAATCAATAATTTGTGGTGATTTGGATCTGTGTTTTAATGAGTTTCACAGTGTGAT
TTTGATTATTAATTGTGCAAGCTTTTCCTAATAAACGTGGAGAATCACA

FIGURE 15 continued

HERG (SEQ ID NO: 2)

ACGCGGCCTGCTCAGGCCTCCAGCGGCCGGTCGGAGGGGAGGCGGGAGGCGAGCGAGGACCCGCGCCCGC
AGTCCAGTCTGTGCGCGCCCGTGCTCGCTTGGCGCGGTGCGGGACCAGCGCCGGCCACCCGAAGCCTAGT
GCGTCGCCGGGTGGGTGGGCCCGCCCGGCGCCATGGGCTCAGGATGCCGGTGCGGAGGGGCCACGTCGCG
CCGCAGAACACCTTCCTGGACACCATCATCCGCAAGTTTGAGGGCCAGAGCCGTAAGTTCATCATCGCCA
ACGCTCGGGTGGAGAACTGCGCCGTCATCTACTGCAACGACGGCTTCTGCGAGCTGTGCGGCTACTCGCG
GGCCGAGGTGATGCAGCGACCCTGCACCTGCGACTTCCTGCACGGGCCGCGCACGCAGCGCCGCGCTGCC
GCGCAGATCGCGCAGGCACTGCTGGGCGCCGAGGAGCGCAAAGTGGAAATCGCCTTCTACCGGAAAGATG
GGAGCTGCTTCCTATGTCTGGTGGATGTGGTGCCCGTGAAGAACGAGGATGGGGCTGTCATCATGTTCAT
CCTCAATTTCGAGGTGGTGATGGAGAAGGACATGGTGGGGTCCCCGGCTCATGACACCAACCACCGGGGC
CCCCCCACCAGCTGGCTGGCCCCAGGCCGCGCCAAGACCTTCCGCCTGAAGCTGCCCGCGCTGCTGGCGC
TGACGGCCCGGGAGTCGTCGGTGCGGTCGGGCGGCGCGGGCGGCGCGGGCGCCCCGGGGGCCGTGGTGGT
GGACGTGGACCTGACGCCCGCGGCACCCAGCAGCGAGTCGCTGGCCCTGGACGAAGTGACAGCCATGGAC
AACCACGTGGCAGGGCTCGGGCCCGCGGAGGAGCGGCGTGCGCTGGTGGGTCCCGGCTCTCCGCCCCGCA
GCGCGCCCGGCCAGCTCCCATCGCCCCGGGCGCACAGCCTCAACCCCGACGCCTCGGGCTCCAGCTGCAG
CCTGGCCCGGACGCGCTCCCGAGAAAGCTGCGCCAGCGTGCGCCGCGCCTCGTCGGCCGACGACATCGAG
GCCATGCGCGCCGGGGTGCTGCCCCCGCCACCGCGCCACGCCAGCACCGGGGCCATGCACCCACTGCGCA
GCGGCTTGCTCAACTCCACCTCGGACTCCGACCTCGTGCGCTACCGCACCATTAGCAAGATTCCCCAAAT
CACCCTCAACTTTGTGGACCTCAAGGGCGACCCCTTCTTGGCTTCGCCCACCAGTGACCGTGAGATCATA
GCACCTAAGATAAAGGAGCGAACCCACAATGTCACTGAGAAGGTCACCCAGGTCCTGTCCCTGGGCGCCG
ACGTGCTGCCTGAGTACAAGCTGCAGGCACCGCGCATCCACCGCTGGACCATCCTGCATTACAGCCCCTT
CAAGGCCGTGTGGGACTGGCTCATCCTGCTGCTGGTCATCTACACGGCTGTCTTCACACCCTACTCGGCT
GCCTTCCTGCTGAAGGAGACGGAAGAAGGCCCGCCTGCTACCGAGTGTGGCTACGCCTGCCAGCCGCTGG
CTGTGGTGGACCTCATCGTGGACATCATGTTCATTGTGGACATCCTCATCAACTTCCGCACCACCTACGT
CAATGCCAACGAGGAGGTGGTCAGCCACCCCGGCCGCATCGCCGTCCACTACTTCAAGGGCTGGTTCCTC
ATCGACATGGTGGCCGCCATCCCCTTCGACCTGCTCATCTTCGGCTCTGGCTCTGAGGAGCTGATCGGGC
TGCTGAAGACTGCGCGGCTGCTGCGGCTGGTGCGCGTGGCGCGGAAGCTGGATCGCTACTCAGAGTACGG
CGCGGCCGTGCTGTTCTTGCTCATGTGCACCTTTGCGCTCATCGCGCACTGGCTAGCCTGCATCTGGTAC
GCCATCGGCAACATGGAGCAGCCACACATGGACTCACGCATCGGCTGGCTGCACAACCTGGGCGACCAGA
TAGGCAAACCCTACAACAGCAGCGGCCTGGGCGGCCCCTCCATCAAGGACAAGTATGTGACGGCGCTCTA
CTTCACCTTCAGCAGCCTCACCAGTGTGGGCTTCGGCAACGTCTCTCCCAACACCAACTCAGAGAAGATC
TTCTCCATCTGCGTCATGCTCATTGGCTCCCTCATGTATGCTAGCATCTTCGGCAACGTGTCGGCCATCA
TCCAGCGGCTGTACTCGGGCACAGCCCGCTACCACACACAGATGCTGCGGGTGCGGGAGTTCATCCGCTT
CCACCAGATCCCCAATCCCCTGCGCCAGCGCCTCGAGGAGTACTTCCAGCACGCCTGGTCCTACACCAAC
GGCATCGACATGAACGCGGTGCTGAAGGGCTTCCCTGAGTGCCTGCAGGCTGACATCTGCCTGCACCTGA
ACCGCTCACTGCTGCAGCACTGCAAACCCTTCCGAGGGGCCACCAAGGGCTGCCTTCGGGCCCTGGCCAT
GAAGTTCAAGACCACACATGCACCGCCAGGGGACACACTGGTGCATGCTGGGGACCTGCTCACCGCCCTG
TACTTCATCTCCCGGGGCTCCATCGAGATCCTGCGGGGCGACGTCGTCGTGGCCATCCTGGGGAAGAATG
ACATCTTTGGGGAGCCTCTGAACCTGTATGCAAGGCCTGGCAAGTCGAACGGGGATGTGCGGGCCCTCAC
CTACTGTGACCTACACAAGATCCATCGGGACGACCTGCTGGAGGTGCTGGACATGTACCCTGAGTTCTCC
GACCACTTCTGGTCCAGCCTGGAGATCACCTTCAACCTGCGAGATACCAACATGATCCCGGGCTCCCCCG
GCAGTACGGAGTTAGAGGGTGGCTTCAGTCGGCAACGCAAGCGCAAGTTGTCCTTCCGCAGGCGCACGGA
CAAGGACACGGAGCAGCCAGGGGAGGTGTCGGCCTTGGGGCCGGGCCGGGCGGGGGCAGGGCCGAGTAGC
CGGGGCCGGCCGGGGGGGCCGTGGGGGGAGAGCCCGTCCAGTGGCCCCTCCAGCCCTGAGAGCAGTGAGG
ATGAGGGCCCAGGCCGCAGCTCCAGCCCCCTCCGCCTGGTGCCCTTCTCCAGCCCCAGGCCCCCCGGAGA
GCCGCCGGGTGGGGAGCCCCTGATGGAGGACTGCGAGAAGAGCAGCGACACTTGCAACCCCCTGTCAGGC
GCCTTCTCAGGAGTGTCCAACATTTTCAGCTTCTGGGGGGACAGTCGGGGCCGCCAGTACCAGGAGCTCC

FIGURE 15 continued

CTCGATGCCCCGCCCCCACCCCCAGCCTCCTCAACATCCCCCTCTCCAGCCCGGGTCGGCGGCCCCGGGG
CGACGTGGAGAGCAGGCTGGATGCCCTCCAGCGCCAGCTCAACAGGCTGGAGACCCGGCTGAGTGCAGAC
ATGGCCACTGTCCTGCAGCTGCTACAGAGGCAGATGACGCTGGTCCCGCCCGCCTACAGTGCTGTGACCA
CCCCGGGGCCTGGCCCCACTTCCACATCCCCGCTGTTGCCCGTCAGCCCCCTCCCCACCCTCACCTTGGA
CTCGCTTTCTCAGGTTTCCCAGTTCATGGCGTGTGAGGAGCTGCCCCCGGGGGCCCCAGAGCTTCCCCAA
GAAGGCCCCACACGACGCCTCTCCCTACCGGGCCAGCTGGGGGCCCTCACCTCCCAGCCCCTGCACAGAC
ACGGCTCGGACCCGGGCAGTTAGTGGGGCTGCCCAGTGTGGACACGTGGCTCACCCAGGGATCAAGGCGC
TGCTGGGCCGCTCCCCTTGGAGGCCCTGCTCAGGAGGCCCTGACCGTGGAAGGGGAGAGGAACTCGAAAG
CACAGCTCCTCCCCCAGCCCTTGGGACCATCTTCTCCTGCAGTCCCCTGGGCCCCAGTGAGAGGGGCAGG
GGCAGGGCCGGCAGTAGGTGGGGCCTGTGGTCCCCCCACTGCCCTGAGGGCATTAGCTGGTCTAACTGCC
CGGAGGCACCCGGCCCTGGGCCTTAGGCACCTCAAGGACTTTTCTGCTATTTACTGCTCTTATTGTTAAG
GATAATAATTAAGGATCATATGAATAATTAATGAAGATGCTGATGACTATGAATAATAAATAATTATCCT
GAGGAGAAAA

SEQUENCE LISTING

<160> NUMBER OF SEQ ID NOS: 7

<210> SEQ ID NO 1
<211> LENGTH: 3129
<212> TYPE: DNA
<213> ORGANISM: Homo sapiens

<400> SEQUENCE: 1

```
gggcggcggg gctggcagca gtggctgccc gcactgcgcc cgggcgctcg ccttcgctgc     60

agctcccggt gccgccgctc gggccggccc cccggcaggc cctcctcgtt atggccgcgg    120

cctcctcccc gcccagggcc gagaggaagc gctggggttg gggccgcctg ccaggcgccc    180

ggcggggcag cgcgggcctg gccaagaagt gccccttctc gctggagctg gcggagggcg    240

gcccggcggg cggcgcgctc tacgcgccca tcgcgcccgg cgccccaggt cccgcgcccc    300

ctgcgtcccc ggccgcgccc gccgcgcccc cagttgcctc cgaccttggc ccgcggccgc    360

cggtgagcct agacccgcgc gtctccattt acagcacgcg ccgcccggtg ttggcgcgca    420

cccacgtcca gggccgcgtc tacaacttcc tcgagcgtcc caccggctgg aaatgcttcg    480

tttaccactt cgccgtcttc ctcatcgtcc tggtctgcct catcttcagc gtgctgtcca    540

ccatcgagca gtatgccgcc ctggccacgg ggactctctt ctggatggag atcgtgctgg    600

tggtgttctt cgggacggag tacgtggtcc gcctctggtc cgccggctgc cgcagcaagt    660

acgtgggcct ctgggggcgg ctgcgctttg cccggaagcc catttccatc atcgacctca    720

tcgtggtcgt ggcctccatg gtggtcctct gcgtgggctc caaggggcag gtgtttgcca    780

cgtcggccat caggggcatc cgcttcctgc agatcctgag gatgctacac gtcgaccgcc    840

agggaggcac ctggaggctc ctgggctccg tggtcttcat ccaccgccag gagctgataa    900

ccaccctgta catcggcttc ctgggcctca tcttctcctc gtactttgtg tacctggctg    960

agaaggacgc ggtgaacgag tcaggccgcg tggagttcgg cagctacgca gatgcgctgt   1020

ggtggggggt ggtcacagtc accaccatcg gctatgggga caaggtgccc cagacgtggg   1080

tcgggaagac catcgcctcc tgcttctctg tctttgccat ctccttcttt gcgctcccag   1140

cggggattct tggctcgggg tttgccctga aggtgcagca gaagcagagg cagaagcact   1200

tcaaccggca gatcccggcg gcagcctcac tcattcagac cgcatggagg tgctatgctg   1260

ccgagaaccc cgactcctcc acctggaaga tctacatccg gaaggccccc cggagccaca   1320

ctctgctgtc acccagcccc aaacccaaga agtctgtggt ggtaaagaaa aaaaagttca   1380

agctggacaa agacaatggg gtgactcctg gagagaagat gctcacagtc cccccatatca   1440

cgtgcgaccc ccagaagag cggcggctgg accacttctc tgtcgacggc tatgacagtt   1500

ctgtaaggaa gagcccaaca ctgctggaag tgagcatgcc ccatttcatg agaaccaaca   1560

gcttcgccga ggacctggac ctggaagggg agactctgct gacacccatc acccacatct   1620

cacagctgcg ggaacaccat cgggccacca ttaaggtcat tcgacgcatg cagtactttg   1680

tggccaagaa gaaattccag caagcgcgga agccttacga tgtgcgggac gtcattgagc   1740

agtactcgca gggccacctc aacctcatgg tgcgcatcaa ggagctgcag aggaggctgg   1800

accagtccat tgggaagccc tcactgttca tctccgtctc agaaaagagc aaggatcgcg   1860

gcagcaacac gatcggcgcc cgcctgaacc gagtagaaga caaggtgacg cagctggacc   1920

agaggctggc actcatcacc gacatgcttc accagctgct ctccttgcac ggtggcagca   1980

cccccggcag cggcggcccc cccagagagg gcggggccca catcacccag ccctgcggca   2040
```

-continued gtggcggctc cgtcgaccct gagctcttcc tgcccagcaa caccctgccc acctacgagc 2100
agctgaccgt gcccaggagg ggccccgatg aggggtcctg aggaggggat ggggctgggg 2160
gatgggcctg agtgagaggg gaggccaaga gtggccccac ctggccctct ctgaaggagg 2220
ccacctccta aaaggcccag agagaagagc cccactctca gaggccccaa taccccatgg 2280
accatgctgt ctggcacagc ctgcacttgg gggctcagca aggccacctc ttcctggccg 2340
gtgtgggggc cccgtctcag gtctgagttg ttaccccaag cgccctggcc cccacatggt 2400
gatgttgaca tcactggcat ggtggttggg acccagtggc agggcacagg gcctggccca 2460
tgtatggcca ggaagtagca caggctgagt gcaggcccac cctgcttggc ccagggggct 2520
tcctgagggg agacagagca accccctggac cccagcctca aatccaggac cctgccaggc 2580
acaggcaggg caggaccagc ccacgctgac tacagggcca ccggcaataa aagcccagga 2640
gcccatttgg agggcctggg cctggctccc tcactctcag gaaatgctga cccatgggca 2700
ggagactgtg gagactgctc ctgagccccc agcttccagc aggagggaca gtctcaccat 2760
ttccccaggg cacgtggttg agtgggggga acgcccactt ccctgggtta gactgccagc 2820
tcttcctagc tggagaggag ccctgcctct ccgcccctga gcccactgtg cgtggggctc 2880
ccgcctccaa cccctcgccc agtcccagca gccagccaaa cacacagaag gggactgcca 2940
cctccccttg ccagctgctg agccgcagag aagtgacggt tcctacacag gacaggggtt 3000
ccttctgggc attacatcgc atagaaatca ataatttgtg gtgatttgga tctgtgtttt 3060
aatgagtttc acagtgtgat tttgattatt aattgtgcaa gcttttccta ataaacgtgg 3120
agaatcaca 3129

<210> SEQ ID NO 2
<211> LENGTH: 4070
<212> TYPE: DNA
<213> ORGANISM: Homo sapiens

<400> SEQUENCE: 2
acgcggcctg ctcaggcctc cagcggccgg tcggagggga ggcgggaggc gagcgaggac 60
ccgcgcccgc agtccagtct gtgcgcgccc gtgctcgctt ggcgcggtgc gggaccagcg 120
ccggccaccc gaagcctagt gcgtcgccgg gtgggtgggc ccgcccggcg ccatgggctc 180
aggatgccgg tgcggagggg ccacgtcgcg ccgcagaaca ccttcctgga caccatcatc 240
cgcaagtttg agggccagag ccgtaagttc atcatcgcca acgctcgggt ggagaactgc 300
gccgtcatct actgcaacga cggcttctgc gagctgtgcg gctactcgcg ggccgaggtg 360
atgcagcgac cctgcacctg cgacttcctg cacgggccgc gcacgcagcg ccgcgctgcc 420
gcgcagatcg cgcaggcact gctgggcgcc gaggagcgca aagtggaaat cgccttctac 480
cggaaagatg ggagctgctt cctatgtctg gtggatgtgg tgcccgtgaa gaacgaggat 540
ggggctgtca tcatgttcat cctcaatttc gaggtggtga tggagaagga catggtgggg 600
tccccggctc atgacaccaa ccaccggggc ccccccacca gctggctggc cccaggccgc 660
gccaagacct tccgcctgaa gctgcccgcg ctgctggcgc tgacggcccg ggagtcgtcg 720
gtgcggtcgg gcggcgcggg cggcgcgggc gccccggggg ccgtggtggt ggacgtggac 780
ctgacgcccg cggcacccag cagcgagtcg ctggccctgg acgaagtgac agccatggac 840
aaccacgtgg cagggctcgg gcccgcggag gagcggcgtg cgctggtggg tcccggctct 900
ccgccccgca gcgcgcccgg ccagctccca tcgccccggg cgcacagcct caaccccgac 960

-continued

```
gcctcgggct ccagctgcag cctggcccgg acgcgctccc gagaaagctg cgccagcgtg   1020

cgccgcgcct cgtcggccga cgacatcgag gccatgcgcg ccggggtgct gcccccgcca   1080

ccgcgccacg ccagcaccgg ggccatgcac ccactgcgca gcggcttgct caactccacc   1140

tcggactccg acctcgtgcg ctaccgcacc attagcaaga ttccccaaat caccctcaac   1200

tttgtggacc tcaagggcga ccccttcttg gcttcgccca ccagtgaccg tgagatcata   1260

gcacctaaga taaaggagcg aacccacaat gtcactgaga aggtcaccca ggtcctgtcc   1320

ctgggcgccg acgtgctgcc tgagtacaag ctgcaggcac cgcgcatcca ccgctggacc   1380

atcctgcatt acagcccctt caaggccgtg tgggactggc tcatcctgct gctggtcatc   1440

tacacggctg tcttcacacc ctactcggct gccttcctgc tgaaggagac ggaagaaggc   1500

ccgcctgcta ccgagtgtgg ctacgcctgc cagccgctgg ctgtggtgga cctcatcgtg   1560

gacatcatgt tcattgtgga catcctcatc aacttccgca ccacctacgt caatgccaac   1620

gaggaggtgg tcagccaccc cggccgcatc gccgtccact acttcaaggg ctggttcctc   1680

atcgacatgg tggccgccat ccccttcgac ctgctcatct tcggctctgg ctctgaggag   1740

ctgatcgggc tgctgaagac tgcgcggctg ctgcggctgg tgcgcgtggc gcggaagctg   1800

gatcgctact cagagtacgg cgcggccgtg ctgttcttgc tcatgtgcac ctttgcgctc   1860

atcgcgcact ggctagcctg catctggtac gccatcggca acatggagca gccacacatg   1920

gactcacgca tcggctggct gcacaacctg ggcgaccaga taggcaaacc ctacaacagc   1980

agcggcctgg gcggcccctc catcaaggac aagtatgtga cggcgctcta cttcaccttc   2040

agcagcctca ccagtgtggg cttcggcaac gtctctccca acaccaactc agagaagatc   2100

ttctccatct gcgtcatgct cattggctcc ctcatgtatg ctagcatctt cggcaacgtg   2160

tcggccatca tccagcggct gtactcgggc acagcccgct accacacaca gatgctgcgg   2220

gtgcgggagt tcatccgctt ccaccagatc cccaatcccc tgcgccagcg cctcgaggag   2280

tacttccagc acgcctggtc ctacaccaac ggcatcgaca tgaacgcggt gctgaagggc   2340

ttccctgagt gcctgcaggc tgacatctgc ctgcacctga accgctcact gctgcagcac   2400

tgcaaaccct tccgaggggc caccaagggc tgccttcggg ccctggccat gaagttcaag   2460

accacacatg caccgccagg ggacacactg gtgcatgctg gggacctgct caccgccctg   2520

tacttcatct cccggggctc catcgagatc ctgcggggcg acgtcgtcgt ggccatcctg   2580

gggaagaatg acatctttgg ggagcctctg aacctgtatg caaggcctgg caagtcgaac   2640

ggggatgtgc gggccctcac ctactgtgac ctacacaaga tccatcggga cgacctgctg   2700

gaggtgctgg acatgtaccc tgagttctcc gaccacttct ggtccagcct ggagatcacc   2760

ttcaacctgc gagataccaa catgatcccg ggctccccgg gcagtacgga gttagagggt   2820

ggcttcagtc ggcaacgcaa gcgcaagttg tccttccgca ggcgcacgga caaggacacg   2880

gagcagccag gggaggtgtc ggccttgggg ccgggccggg cgggggcagg gccgagtagc   2940

cggggccggc cggggggccc gtggggggag agcccgtcca gtggcccctc cagccctgag   3000

agcagtgagg atgagggccc aggccgcagc tccagccccc tccgcctggt gcccttctcc   3060

agccccaggc cccccggaga gccgccgggt ggggagcccc tgatggagga ctgcgagaag   3120

agcagcgaca cttgcaaccc cctgtcaggc gccttctcag gagtgtccaa cattttcagc   3180

ttctgggggg acagtcgggg ccgccagtac caggagctcc ctcgatgccc cgcccccacc   3240

cccagcctcc tcaacatccc cctctccagc ccgggtcggc ggccccgggg cgacgtggag   3300

agcaggctgg atgccctcca gcgccagctc aacaggctgg agacccggct gagtgcagac   3360
```

-continued atggccactg tcctgcagct gctacagagg cagatgacgc tggtcccgcc cgcctacagt 3420
gctgtgacca ccccggggcc tggccccact tccacatccc cgctgttgcc cgtcagcccc 3480
ctccccaccc tcaccttgga ctcgctttct caggtttccc agttcatggc gtgtgaggag 3540
ctgcccccgg gggccccaga gcttccccaa gaaggcccca cacgacgcct ctccctaccg 3600
ggccagctgg gggccctcac ctcccagccc ctgcacagac acggctcgga cccgggcagt 3660
tagtggggct gcccagtgtg gacacgtggc tcacccaggg atcaaggcgc tgctgggccg 3720
ctccccttgg aggccctgct caggaggccc tgaccgtgga aggggagagg aactcgaaag 3780
cacagctcct cccccagccc ttgggaccat cttctcctgc agtcccctgg gccccagtga 3840
gaggggcagg ggcagggccg gcagtaggtg gggcctgtgg tccccccact gccctgaggg 3900
cattagctgg tctaactgcc cggaggcacc cggccctggg ccttaggcac ctcaaggact 3960
tttctgctat ttactgctct tattgttaag gataataatt aaggatcata tgaataatta 4020
atgaagatgc tgatgactat gaataataaa taattatcct gaggagaaaa 4070

<210> SEQ ID NO 3
<211> LENGTH: 32
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 3
gaaccagctt cttccgctca ctacaggtac ag 32

<210> SEQ ID NO 4
<211> LENGTH: 31
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 4
gggcaccaca tccaccagac ataggaagca g 31

<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 5
cccaccatgt ccatcaccac ctc 23

<210> SEQ ID NO 6
<211> LENGTH: 31
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 6
agccggtggg acgctcgagg aagttgtaga c 31

<210> SEQ ID NO 7

-continued

```
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7

aagatgaggc agaccaggac gatgaggaag ac                                32
```

ANIMAL MODELS OF LONG QT SYNDROME AND USES THEREOF

BACKGROUND OF THE INVENTION

Cardiac cell excitation is crucially controlled by several large superfamilies of ion channels that regulate the depolarization and repolarization phases, trigger calcium release in individual myocytes, and govern the conduction and coordinated contractile function of the heart. For example, voltage-gated outward $K^+$ currents control the shape and duration of the action potential (AP) in cardiac myocytes. Classically, the time-dependent $K^+$-channels are divided into the transient outward current ($I_{to}$) that underlies the first phase (phase 1) of AP repolarization and the ultra-rapid, rapid, and slow delayed rectifier currents ($I_{Kur}$, $I_{Kr}$, and $I_{Ks}$) that determine the middle and late phases of repolarization.

Long QT syndrome (LQTS) is a disorder characterized by a prolonged myocardial repolarization, an abnormally long QT interval in surface (ECG) and recurrent episodes of ventricular tachyarrhythmias, which may lead to syncope, cardiac arrest, or sudden death. LQTS may be congenital or induced, but both forms of the syndrome are caused by defects in the ion channel mechanism controlling cardiac cell excitation. Congenital LQTS is caused by mutations of cardiac ion channel genes; 7 chromosomal loci and 7 specific genes have been identified to date, and is subdivided into two different syndromes, Romano-Ward syndrome and Jervell and Lang-Nielsen (JLN) syndrome. Romano-Ward syndrome is characterized by familial occurrence with autosomal dominant inheritance, QT prolongation, and ventricular tachyarrhythmias, while JLN syndrome is characterized by familial occurrence with autosomal recessive inheritance, congenital deafness, QT prolongation, and ventricular arrhythmias. Based on genetic background, 6 types of LQTS and 2 types of JLN syndrome have been identified, as shown in FIGS. 1-2. The prevalence of LQTS is difficult to estimate, but, based on the currently increasing frequency of diagnosis, LQTS is expected to occur in 1 in 1,000-2,000 individuals. LQTS is an underdiagnosed disorder, especially because at least 10-15% of LQTS gene carriers have normal QTc duration.

The most prevalent congenital forms of LQTS, LQT1 and LQT2 and LQT3 are related to loss of function of delayed rectifier currents $I_{Ks}$ or $I_{Kr}$ due to mutations in the α-subunit KvLQT1 (KCNQ1) or HERG (KCNH2), respectively gain of function mutations of the voltage-gated cardiac sodium channel α-subunit SCN5A. Linkage studies have revealed that null mutations in HERG (KCNH2), a gene located on chromosome 7 that encodes the pore-forming subunit of a voltage-gated potassium channel $I_{Kr}$, the LQT2 form of LQTS. Gain-of-function mutations in the putative inactivation domain of the human cardiac $Na^+$ channel, SCN5A result in LQT3. Mutations in KCNE2, a minK-related peptide (MiRP1) that may co-assemble with HERG to form $I_{Kr}$, may cause LQT6. JLN syndrome, a variant of LQTS, is associated with prolonged repolarization, deafness, and sudden death. The disease is related to mutations in both of the alleles encoding KvLQT1. Loss of function mutations in the inward rectifier potassium channel Kir2.1 (KCNJ2) cause LQT7.

Torsade de pointes (TdP) is an atypical polymorphic ventricular tachycardia most often associated with QT prolongation in both congenital and acquired forms of LQTS. Several experimental and clinical observations using monophasic action potential suggest a significant role for early afterdepolarization (EAD)-induced triggered activity in the genesis of TdP. These EADs can induce reentry and TdP if there is dispersion of repolarization across the wall of the heart.

EADs may also be induced either by interventions that decrease the repolarizing $K^+$ currents (e.g., class III antiarrhythmic drugs) or increase the inward currents $I_{Na}$ or $I_{Ca}$.

However, the mechanisms behind the various types of LQTS and associated disorders are still not fully understood. Mice models have been instrumental in understanding the assembly and role of ionic channels in regulating repolarization in the heart. However, because the mouse heart is small, the resting heart rate is 600 beats/min, and the APD is very short, different time-dependent currents play a role in repolarization as compared with those in humans. A need exists, therefore, for an animal model system that is more similar to humans in terms of its repolarizing currents.

While mice and rats remain the most widely used animal models in genetic investigation of many human diseases, there remain certain diseases for which mice and rats are not an accurate model for human disease. The ionic mechanisms of repolarization in adult rats and mice differ from larger species, including humans (the primary ion currents controlling repolarization in adult rats and mice is $I_{to}$); therefore, use of these species is not considered appropriate for modeling cardiac ion channel disorders such as LQTS. To date there are no genetic models to study the long-term effects of suppression of $I_{Kr}$ and $I_{Ks}$ in a model in which these channels control cardiac repolarization and the shape of its action potential.

Other non-murine laboratory animal species that may be more suitable for in vivo electrophysiology and other studies to explore human cardiac diseases and study potential therapies include dog, monkey, swine, rabbit, ferret, and guinea pig. For example, the rabbit's larger size and slower heart rate allow performance of electrophysiologic studies that more accurately model human physiology. The rabbit heart is also more similar to the human heart in terms of the contractile proteins that are expressed and the ion channels important for repolarization. For example, similar to the case in humans, the calcium-insensitive $I_{to}$ plays an important role in the rabbit cardiomyocyte; it is likely coded by Kv1.4, Kv4.2 and Kv4.3, while in humans $I_{to}$ is coded by primarily Kv4.3. $I_{Ks}$ is also easily detected in the rabbit heart, but is less prominent than in guinea pigs and humans. This current is unique in its slow activation kinetics—it occurs on the order of seconds—and is constant among different species. However, its deactivation is slow in guinea pig, but relatively fast in the rabbit and human. Thus, $I_{Ks}$ is believed to be particularly important in situations in which repolarization is impaired by either inward-current enhancement or outward-current reduction (like β-adrenergic drive and impaired rapid delayed-rectifier function). Indeed, under resting conditions, $I_{Ks}$ seems to be smaller, but it is activated under sympathetic stimulation. Similar to humans, $I_{Kr}$ plays a major role in the rabbit heart. As a result, the rabbit is particularly sensitive to class III drugs and responds with prolongation of the QT interval and EADs. The dominant role of $I_{Kr}$ compared with $I_{Ks}$ is likely due to lower steady-state levels of minK transcript. Of note, Tsuji et al. demonstrated recently in rabbits that complete AV block leads to substantial QT prolongation and high incidence of spontaneous TdP. Both $I_{Kr}$ and $I_{Ks}$ were downregulated by about 50% in this model.

SUMMARY OF THE INVENTION

Provided herein are transgenic non-human mammalian models for LQTS and related disorders that more closely approximate such disorders in humans, for example, by having repolarizing currents more similar to those of humans. Also provided are constructs, vectors and methods for making such transgenic non-human mammalian models, as well as cell lines, tissues and samples derived from such transgenic non-human mammalian models. Further provided are various methods of using the transgenic non-human mammalian models and products derived therefrom, for example, in drug screening methods, gene expression studies, and drug discovery. In particular, the mammalian models for LQTS are useful for assessing the potential for a therapeutic to cause LQTS and related disorders, e.g. in a drug safety testing method. Kits for the practice of the methods are also provided.

These embodiments of the present invention, other embodiments, and their features and characteristics will be apparent from the description, drawings, and claims that follow.

BRIEF DESCRIPTION OF THE FIGURES

FIG. 1 depicts the chromosomal locus, mutation and ion channel affected for each of the known types of Romano Ward syndrome.

FIG. 2 depicts the chromosomal locus, mutation and ion channel affected for each of the known types of JLN syndrome.

FIG. 5 depicts the PCR products for HERG and KvLQT1 using genomic DNA obtained from rabbit ear biopsies. The reverse primer used for HERG was HERG-B. The reverse primer used for KvLQT1 was KvLQT1-A. The (+) denotes positive control PCR using the transgene plasmid as a template. The (−) denotes no template DNA. The lanes 33 and 2 denote rabbits #033 and #002, respectively.

FIG. 9 depicts surface ECGs of rabbit #80. Both panels depict simultaneously recorded leads I, II, and III. The top panel shows sinus rhythm with prolonged QT interval and ventricular bigeminy associated with R on T phenomena. The bottom panel depicts sinus rhythm with prolonged QT interval.

FIG. 15 depicts the wild-type sequences of some exemplary human genes that may comprise the genome of the transgenic animals of the invention (SEQ ID NOS 1 and 2).

DETAILED DESCRIPTION OF THE INVENTION

1. General

Figure 3:
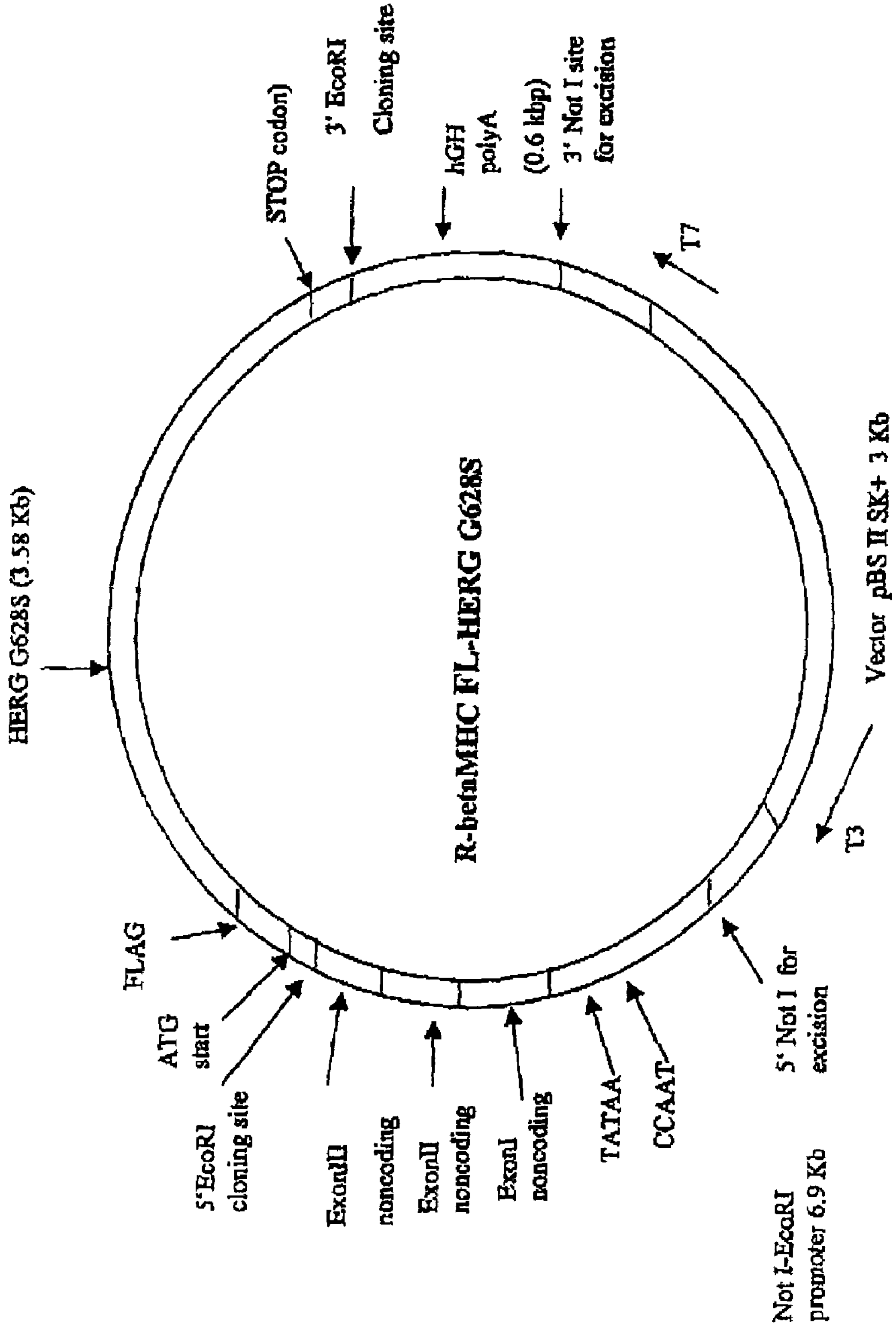
FIG. 3 depicts a construct comprising a FL-HERG G628S, mutant subunit and a rabbit β-MyHC promoter used to create the transgenic HERG dominant negative (ERG-DN) rabbits.

We reasoned that, due to the similarity in the repolarizing currents and to its arrhythmogenicity, the rabbit could serve as a useful genetic model system to study mechanisms of arrhythmias in congenital and acquired LQTS. Moreover, the transgene-mediated long-term suppression of $I_{Kr}$ and $I_{Ks}$ offers two different models to induce prolongation of the APD that will complement and extend the observations in short-term pharmacologic studies in dogs or adenoviral-mediated modulation of these currents in various animal models. It seems, however, that the high costs and the relatively slow process associated with making non-murine animal models deterred researchers from producing a non-murine model of LQTS, such as a rabbit model. Since no rabbit ES cell lines are yet available, we found that the most efficient model to modify the function of ion channels in vivo in the rabbit heart is a dominant negative approach, using a mutated channel overexpressed in the heart under the rabbit β-MyHC promoter.

2. Definitions

For convenience, certain terms employed in the specification, examples, and appended claims are collected here. Unless defined otherwise, all technical and scientific terms used herein have the same meaning as commonly understood by one of ordinary skill in the art to which this invention belongs.

The articles "a" and "an" are used herein to refer to one or to more than one (i.e., to at least one) of the grammatical object of the article. By way of example, "an element" means one element or more than one element.

"Allele", which is used interchangeably herein with "allelic variant", refers to alternative forms of a gene or portions thereof. Alleles occupy the same locus or position on homologous chromosomes. When a subject has two identical alleles of a gene, the subject is said to be homozygous for the gene or allele. When a subject has two different alleles of a gene, the subject is said to be heterozygous for the gene. Alleles of a specific gene may differ from each other in a single nucleotide, or several nucleotides, and may include substitutions, deletions, and insertions of nucleotides. An allele of a gene may also be a form of a gene containing a mutation.

"Amplification," refers to the production of additional copies of a nucleic acid sequence. Amplification is generally carried out using polymerase chain reaction (PCR) technologies well known in the art. (Dieffenbach, C. W. and G. S. Dveksler (1995) PCR Primer, a Laboratory Manual, Cold Spring Harbor Press, Plainview, N.Y.)

The term "amino acid" is intended to embrace all molecules, whether natural or synthetic, which include both an amino functionality and an acid functionality and capable of being included in a polymer of naturally-occurring amino acids. Exemplary amino acids include naturally-occurring amino acids; analogs, derivatives and congeners thereof; amino acid analogs having variant side chains; and all stereoisomers of any of any of the foregoing. The names of the natural amino acids are abbreviated herein in accordance with the recommendations of IUPAC-IUB.

"Biological sample" or "sample", refers to a sample obtained from an organism or from components (e.g., cells) of an organism. The sample may be of any biological tissue, component or fluid. Frequently the sample will be a "clinical sample" which is a sample derived from a patient. Such samples include, but are not limited to, sputum, blood, blood cells (e.g., white cells), tissue or fine needle biopsy samples, urine, peritoneal fluid, and pleural fluid, or cells therefrom. Biological samples may also include sections of tissues such as frozen sections taken for histological purposes. Samples may also comprise cell extracts and purified components, such as proteins, nucleic acids, and the like, from such cell extracts.

A "cardiac ion channel gene involved in long QT syndrome (LQTS)" refers to any gene encoding a cardiac ion channel that contributes (by deletion, mutation, variation in activity) to a defect in the ion channel mechanism controlling cardiac cell excitation. The term therefore includes both wild-type and mutant cardiac ion channel genes.

The terms "comprise" and "comprising" are used in the inclusive, open sense, meaning that additional elements may be included.

"Gene" or "recombinant gene" refer to a nucleic acid molecule comprising an open reading frame and including at least one exon and (optionally) an intron sequence. "Intron" refers to a DNA sequence present in a given gene which is spliced out during mRNA maturation.

"Gene construct" or "construct" refers to a vector, plasmid, viral genome or the like which includes a "coding sequence" for a polypeptide or which is otherwise transcribable to a biologically active RNA (e.g., antisense, decoy, ribozyme, etc), may transfect cells, in certain embodiments mammalian cells, and may cause expression of the coding sequence in cells transfected with the construct. The gene construct may include one or more regulatory elements operably linked to the coding sequence, as well as intronic sequences, poly adenylation sites, origins of replication, marker genes, etc.

A "gene involved in long QT syndrome (LQTS)" refers to any gene that contributes (by deletion, mutation, variation in activity) to a defect in the ion channel mechanism controlling cardiac cell excitation. A gene involved in long QT syndrome may be, for example, an ion channel gene, or other gene that is involved in the ion channel regulation and thus controls cardiac cell excitation, such as scaffolding and cytoskeletal proteins, a phosphatase or a kinase.

A "gene that regulates a cardiac ion channel" refers to a gene encoding a protein or other gene product that regulates the activity or expression of a cardiac ion channel. Exemplary genes that regulate a cardiac ion channel include but are not limited to scaffolding and cytoskeletal proteins, phosphatases or kinases.

The term "gene product" refers to a molecule that is produced as a result of transcription of a gene. Gene products include RNA molecules transcribed from a gene, as well as proteins translated from such transcripts.

"Heterozygote," refers to an individual with different alleles at corresponding loci on homologous chromosomes. Accordingly, "heterozygous" describes an individual or strain having different allelic genes at one or more paired loci on homologous chromosomes.

"Homozygote," refers to an individual with the same allele at corresponding loci on homologous chromosomes. Accordingly, "homozygous", describes an individual or a strain having identical allelic genes at one or more paired loci on homologous chromosomes.

"Host cell" refers to a cell transduced with a specified transfer vector. The cell is optionally selected from in vitro cells such as those derived from cell culture, ex vivo cells, such as those derived from an organism, and in vivo cells, such as those in an organism. "Recombinant host cells" refers to cells which have been transformed or transfected with vectors constructed using recombinant DNA techniques. "Host cells" or "recombinant host cells" are terms used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

"Hybridization" refers to any process by which a strand of nucleic acid binds with a complementary strand through base pairing.

"Interact" is meant to include detectable interactions between molecules, such as may be detected using, for example, a hybridization assay. Interact also includes "binding" interactions between molecules. Interactions may be, for example, protein-protein, protein-nucleic acid, protein-small molecule or small molecule-nucleic acid in nature.

The term "including" is used to mean "including but not limited to". "Including" and "including but not limited to" are used interchangeably.

"Isolated," with respect to nucleic acids, such as DNA or RNA, refers to molecules separated from other DNAs, or RNAs, respectively, that are present in the natural source of the macromolecule. Isolated also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state. "Isolated" also refers to polypeptides which are isolated from other cellular proteins and is meant to encompass both purified and recombinant polypeptides.

The terms "library" or "combinatorial library" refer to a plurality of molecules, which may be termed "members," synthesized or otherwise prepared from one or more starting materials by employing either the same or different reactants or reaction conditions at each reaction in the library. In general, the members of any library show at least some structural diversity, which often results in chemical and biological diversity. Such structural diversity in preparing libraries of coordination molecules may include, by way of example, metal ion diversity, ligand diversity, solvation diversity or counter-ion diversity. A library may contain any number of members from two different members to about $10^8$ members or more. In certain embodiments, libraries of the present invention have more than about 12, 50 and 90 members. In certain embodiments of the present invention, the starting materials and certain of the reactants are the same, and chemical diversity in such libraries is achieved by varying at least one of the reactants or reaction conditions during the preparation of the library. Combinatorial libraries of the present invention may be prepared in solution or on the solid phase. Further details regarding the libraries of the present invention are described below.

The term "long QT syndrome" or "LQTS" means any disease or disorder, whether congenital or acquired, that is caused by defects in the ion channel mechanism controlling cardiac cell excitation.

"Modulation" refers to up regulation (i.e., activation or stimulation), down regulation (i.e., inhibition or suppression) of a response, or the two in combination or apart.

"Non-human mammals" include any mammal that is not a human. Exemplary non-human mammals include vertebrates such as non-human primates, ovines, bovines, ruminants, lagomorphs, porcines, caprines, equines, canines, felines, etc.

"Non-murine mammal" means a mammal not of the order Rodentia and subfamily Murinae (e.g., mice, rats).

The term "nucleic acid" refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single-stranded (such as sense or antisense) and double-stranded polynucleotides. Exemplary nucleic acids for use in the subject invention include antisense, decoy molecules, recombinant genes (including transgenes) and the like. The term "nucleic acid" encompasses "aptamers", which are single-stranded nucleic acid molecules that have been developed to bind a molecular target, usually by in vitro selection methods.

"Nucleic acid corresponding to a gene" refers to a nucleic acid that may be used for detecting the gene, e.g., a nucleic acid which is capable of hybridizing specifically to the gene.

A "patient" or "subject" or "host" refers to either a human or non-human animal.

The terms "peptide" or "polypeptide" or "protein" refer to the class of molecules made up of a single chain of amino acid residues linked by peptide bonds. Peptides yield two or more amino acids on hydrolysis, and may form the constituent parts of a protein. The term as used herein encompasses both peptides that are derived from proteins, as well as those that are synthetically produced. The terms further encompasses peptides with naturally-occurring amino acid sequences, those with designed or randomly synthesized sequences, peptidomimetics, retro peptides, and variants of any one peptide. "Protein", "polypeptide" and "peptide" may be used interchangeably herein when referring to a naturally occurring or recombinant gene product, e.g., as may be encoded by a coding sequence. A "polypeptide" or "peptide" also may refer to a polymer of amino acids, either naturally occurring or synthetically produced. A "peptide nucleic acid" or "PNA" refers to an analogue of a nucleic acid in which the backbone of the molecule is not sugar-phosphate, but rather a peptide or peptidomimetic. A detailed description of PNAs may be found in Nielsen, et al. *Curr. Issues Mol. Biol.* (1999) 1:89-104. The term "peptidomimetic" refers to a molecule containing peptide-like structural elements that is capable of mimicking the biological action (s) of a natural parent polypeptide.

"Pharmaceutically-acceptable salts" refers to the relatively non-toxic, inorganic and organic acid addition salts of compounds.

"Pharmaceutically acceptable carrier" refers to a pharmaceutically-acceptable material, composition or vehicle, such as a liquid or solid filler, diluent, excipient, solvent or encapsulating material, involved in carrying or transporting any supplement or composition, or component thereof, from one organ, or portion of the body, to another organ, or portion of the body. Each carrier must be "acceptable" in the sense of being compatible with the other ingredients of the supplement and not injurious to the patient. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

"Regulatory relationship" between one gene and another gene refers to the instances in which the first gene is downstream of a gene as well as instances in which the first gene is upstream of a gene. If the expression of a first gene is regulated by a second gene, the second gene is called an "upstream" gene relative to the first gene, and the first gene is "downstream" from the second gene. Regulation of a first gene by a second gene may be through any regulatory method, such as trans-activation, or cis-activation.

"Small molecule" refers to a composition, which has a molecular weight no more than about 20 kDa. Small molecules may be nucleic acids, peptides, peptide-nucleic acids, aptamers polypeptides, peptidomimetics, or other organic (carbon-containing) or inorganic molecules. As those skilled in the art will appreciate, based on the present description, extensive libraries of chemical and/or biological mixtures, often fungal, bacterial, or algal extracts, may be screened with any of the assays of the invention to identify molecules that bind a microorganism.

The term "stress" as used herein refers to any stimulus or physical, chemical, biomechanical, or emotional factor that activates in an animal subjected to the stress LQTS. Examples of stresses include, but are not limited to, physical activities such as running or swimming, electrical stimulation, cardiac injury, administration of compounds, etc.

A "symptom associated with LQTS" refers to any evidence that a subject has LQTS, such as, for example, arrhythmia, death, TdP, long QT intervals, broad-based T waves and transmural dispersion of repolarization.

"Therapeutic agent" or "therapeutic" refers to an agent capable of having a desired biological effect on a host. Chemotherapeutic and genotoxic agents are examples of therapeutic agents that are generally known to be chemical in origin, as opposed to biological, or cause a therapeutic effect by a particular mechanism of action, respectively. Examples of therapeutic agents of biological origin include growth factors, hormones, and cytokines. A variety of therapeutic agents are known in the art and may be identified by their effects.

"Therapeutic effect" refers to a local or systemic effect in animals, particularly mammals, and more particularly humans caused by a pharmacologically active substance. The term thus means any substance intended for use in the diagnosis, cure, mitigation, treatment or prevention of disease or in the enhancement of desirable physical or mental development and conditions in an animal or human. The phrase "therapeutically-effective amount" means that amount of such a substance that produces some desired local or systemic effect at a reasonable benefit/risk ratio applicable to any treatment. In certain embodiments, a therapeutically effective amount of a compound will depend on its therapeutic index, solubility, and the like. For example, certain compounds discovered by the methods of the present invention may be administered in a sufficient amount to produce a at a reasonable benefit/risk ratio applicable to such treatment.

The term "treating" is art-recognized and refers to curing as well as ameliorating at least one symptom of any condition or disease or preventing a condition or disease from worsening.

"Vector" refers to a nucleic acid molecule capable of transporting another nucleic acid to which it has been linked. One type of preferred vector is an episome, i.e., a nucleic acid capable of extra-chromosomal replication. Preferred vectors are those capable of autonomous replication and/or expression of nucleic acids to which they are linked. Vectors capable of directing the expression of genes to which they are operatively linked are referred to herein as "expression vectors". In general, expression vectors of utility in recombinant DNA techniques are often in the form of "plasmids" which refer generally to circular double stranded DNA loops, which, in their vector form are not bound to the chromosome. In the present specification, "plasmid" and "vector" are used interchangeably as the plasmid is the most commonly used form of vector. However, as will be appreciated by those skilled in the art, the invention is intended to include such other forms of expression vectors which serve equivalent functions and which become known in the art subsequently hereto.

3. Non-Human, Non-Murine Transgenic Animal Models and Methods of Making the same Provided are non-human, non-murine transgenic mammals having an ionic mechanism of cardiac cell excitation similar to that of humans, e.g. so that they may serve as models of the human cardiac cell excitation mechanism. In certain embodiments, the non-human, non-murine transgenic mammal's genome comprise a mutated gene involved in long QT syndrome (LQTS). For example, the genome of a transgenic rabbit of the invention may comprise a mutation of one of the rabbit's own wild-type ion channel genes. In other embodiments, the non-human, non-murine transgenic mammals' genome comprises a gene involved in long QT syndrome (LQTS) that is from another mammalian species. For example, the genome of a transgenic rabbit of the invention may comprise a nucleic acid encoding a human gene involved in long QT syndrome (LQTS), such as, for example, a human ion channel gene.

In certain embodiments, the non-human, non-murine mammal may be selected from the group consisting of: lagomorphs (mammals of the order Lagomorpha, including, but not limited to, rabbits, hares, and pikas), cavies (mammals of the order Rodentia and family Caviidae, including, but not limited to guinea pigs), mustelids (mammals of the order Carnivora and family Mustlidae, including, but not limited to ferrets, weasels, and stoats), porcines (mammals of the order Artiodactyla and family Suidae, including, but not limited to hogs and pigs), canines (mammals of the order Carnivora and family Canidae, including, but not limited to domestic dogs), and non-human primates.

In certain embodiments, the genome of a non-human, non-murine transgenic mammal of the invention comprises a human gene involved in LQTS. The human gene involved in LQTS may be any cardiac ion channel gene (e.g. a potassium channel, sodium channel, calcium channel, etc.) implicated in LQTS and related disorders. In certain embodiments, the gene is selected from the group consisting of: KvLQT1 (KCNQ1), HERG (KCNH2), SCN5A, KCNE1, MiRP1, Kir2.1, KCNJ2 and Ankyrin B. The gene may be a wild-type gene or a mutant gene.

In certain embodiments, the gene is a wild-type gene selected from the group consisting of: KvLQT1 (KCNQ1, GenBank accession number AF000571) and HERG (KCNH2, GenBank accession number U04270). In other embodiments, the gene may be selected from the group consisting of: SCN5A, KCNE1, MiRP1, KCNJ2 (Ref Seq NM 000891), Ankyrin B and Kir2.1. The human KCNH2 and KCNQ1 wild-type sequences are listed in FIG. 15. Many naturally-occurring mutations of these sequences are known in the art, as are methods of engineering mutations and variants of these sequences. Such mutations and variations are within the scope of the present invention.

In other embodiments, the human gene involved in long QT syndrome (LQTS) may be a gene that regulates a channel, such as a scaffolding protein, a cytoskeletal protein, a phosphatases or a kinase.

In certain embodiments, the mammal is a rabbit, whose genome comprises either the human mutant cardiac ion channel gene KvLQT1 (KCNQ1-DN) or the human mutant cardiac ion channel gene HERG (ERG-DN). It is an embodiment of the present invention that the transgenes, methods and applications for using the transgenic rabbit of the present invention as described in the Exemplification in detail can be modified and applied to any suitable transgenic animal for the study of LQTS and related disorders.

The transgenic mammals of the invention may also contain genes having gain of function mutations in KCNH2, KvLQT1 and KCNJ2 that cause short QT syndrome type 1, 2 and type 3, respectively (SLQTS1-3) (Priori S G et al., *Circ Res*. 2005 Apr. 15; 96(7):800-7). In particular, the rabbits of the invention may be an ideal candidate for expressing these mutations as transgenes in the heart.

The transgenic mammals of the invention may be more susceptible to various LQT disorders and thus prone to symptoms of such disorders, such as sudden death and arrhythmias. Accordingly, implantable cardioverter defibrillators (ICDs), such as Medtronic's Marquis™ VR 7230B ICD, may be implanted into the subject transgenic mammals in order to monitor and deliver a shock and thus prevent symptoms of LQTS in the transgenic mammals.

The transgenic mammals provided herein all include within a plurality of their cells a transgene of the present invention, which transgene alters the phenotype of the "host cell." Since it is possible to produce transgenic mammals of the invention utilizing one or more of the transgene constructs described herein (such constructs and vectors containing them are embodiments of the invention), a general description will be given of the production of transgenic organisms by referring generally to exogenous genetic material. This general description can be adapted by those skilled in the art in order to incorporate specific transgene sequences into organisms utilizing the methods and materials described below.

In an exemplary embodiment, the "non-human, non-murine transgenic mammals" of the invention may be produced by introducing transgenes into the germline of the non-human, non-murine mammal. Embryonal cells at various developmental stages can be used to introduce transgenes for the production of transgenic animals. Different methods are used depending on the stage of development of the embryonal cell. The zygote is the best target for micro-injection. The use of zygotes as a target for gene transfer has a major advantage in that in most cases the injected DNA will be incorporated into the host genome before the first cleavage [Brinster, et al. (1985) Proc. Natl. Acad. Sci. USA 82:4438-4442]. As a consequence, all cells of the transgenic non-human animal will carry the incorporated transgene. This will in general also be reflected in the efficient transmission of the transgene to offspring of the founder since 50% of the germ cells will harbor the transgene.

Any technique which allows for the addition of the exogenous genetic material into nucleic genetic material can be utilized so long as it is not destructive to the cell, nuclear membrane or other existing cellular or genetic structures. The exogenous genetic material is preferentially inserted into the nucleic genetic material by microinjection. Microinjection of cells and cellular structures is known and is used in the art. Micro-injection of zygotes is the preferred method for incorporating transgenes in practicing the invention. U.S. Pat. No. 4,873,191 describes a method for the micro-injection of zygotes; the disclosure of this patent is incorporated herein in its entirety. The specific line(s) of any animal used to practice this invention are selected for general good health, good embryo yields, good pronuclear visibility in the embryo, and good reproductive fitness. In addition, the haplotype is a significant factor. The line(s) used to practice this invention may themselves be transgenics, and/or may be knockouts (i.e., obtained from animals which have one or more genes partially or completely suppressed).

Normally, fertilized embryos are incubated in suitable media until the pronuclei appear. At about this time, the nucleotide sequence comprising the transgene is introduced into the female or male pronucleus as described below. In certain embodiments, the exogenous genetic material may be added to the male DNA complement of the zygote prior to its being processed by the ovum nucleus or the zygote female pronucleus. It is thought that the ovum nucleus or female pronucleus release molecules which affect the male DNA complement, perhaps by replacing the protamines of the male DNA with histones, thereby facilitating the combination of the female and male DNA complements to form the diploid zygote.

For example, the exogenous genetic material is added to the early pronucleus, as soon as possible after the formation of the pronucleus, which is when the male and female pronuclei are well separated and both are located close to the cell membrane. Alternatively, the exogenous genetic material could be added to the nucleus of the sperm after it has been induced to undergo decondensation. Sperm containing the exogenous genetic material can then be added to the ovum or the decondensed sperm could be added to the ovum with the transgene constructs being added as soon as possible thereafter.

Introduction of the transgene nucleotide sequence into the embryo may be accomplished by any means known in the art such as, for example, microinjection, electroporation, or lipofection. Following introduction of the transgene nucleotide sequence into the embryo, the embryo may be incubated in vitro for varying amounts of time, or reimplanted into the surrogate host, or both. In vitro incubation to maturity is within the scope of this invention. One common method in to incubate the embryos in vitro for about 1-7 days, depending on the species, and then reimplant them into the surrogate host.

Lentiviruses may also be used to introduce the transgene nucleotide sequence into the embryo. The lentivirus containing the sequence is injected into the perivitellin space of the egg. In rabbits, the hit rate is greater than 50% of the offspring. The hit rate with pronuclear injection in pigs is smaller than in rabbits.

For the purposes of this invention, a zygote is essentially the formation of a diploid cell which is capable of developing into a complete organism. Generally, the zygote will be comprised of an egg containing a nucleus formed, either naturally or artificially, by the fusion of two haploid nuclei from a gamete or gametes. Thus, the gamete nuclei must be ones which are naturally compatible, i.e., ones which result in a viable zygote capable of undergoing differentiation and developing into a functioning organism. Generally, a euploid zygote is preferred. If an aneuploid zygote is obtained, then the number of chromosomes should not vary by more than one with respect to the euploid number of the organism from which either gamete originated.

In addition to similar biological considerations, physical ones also govern the amount (e.g., volume) of exogenous genetic material which can be added to the nucleus of the zygote or to the genetic material which forms a part of the zygote nucleus. If no genetic material is removed, then the amount of exogenous genetic material which can be added is limited by the amount which will be absorbed without being physically disruptive. Generally, the volume of exogenous genetic material inserted will not exceed about 10 picoliters. The physical effects of addition must not be so great as to physically destroy the viability of the zygote. The biological limit of the number and variety of DNA sequences will vary depending upon the particular zygote and functions of the exogenous genetic material and will be readily apparent to one skilled in the art, because the genetic material, including the exogenous genetic material, of the resulting zygote must be biologically capable of initiating and maintaining the differentiation and development of the zygote into a functional organism.

The number of copies of the transgene constructs which are added to the zygote is dependent upon the total amount of exogenous genetic material added and will be the amount which enables the genetic transformation to occur. Theoretically only one copy is required; however, generally, numerous copies are utilized, for example, 1,000-20,000 copies of the transgene construct, in order to insure that one copy is functional. As regards the present invention, there will often be an advantage to having more than one functioning copy of each of the inserted exogenous DNA sequences to enhance the phenotypic expression of the exogenous DNA sequences.

Reimplantation is accomplished using standard methods. Usually, the surrogate host is anesthetized, and the embryos are inserted into the oviduct. The number of embryos implanted into a particular host will vary by species, but will usually be comparable to the number of off spring the species naturally produces.

Transgenic offspring of the surrogate host may be screened for the presence and/or expression of the transgene by any suitable method. Screening is often accomplished by PCR, Southern blot or Northern blot analysis, using oligonucleotides or a probe that is complementary to at least a portion of the transgene. Western blot analysis using an antibody against the protein encoded by the transgene may be employed as an alternative or additional method for screening for the presence of the transgene product. Typically, DNA is prepared from ear tissue and analyzed by Southern analysis or PCR for the transgene. Alternatively, the tissues or cells believed to express the transgene at the highest levels are tested for the presence and expression of the transgene RNA or polypeptides using Northern analysis or PCR western or immunoprecipitations, although any tissues or cell types may be used for DNA analysis for the presence of the transgene.

Alternative or additional methods for evaluating the presence of the transgene include, without limitation, suitable biochemical assays such as enzyme and/or immunological assays, histological stains for particular marker or enzyme activities, flow cytometric analysis, and the like. Analysis of the blood may also be useful to detect the presence of the transgene product in the blood, as well as to evaluate the effect of the transgene on the levels of various types of blood cells and other blood constituents.

Progeny of the transgenic animals may be obtained by mating the transgenic animal with a suitable partner, or by in vitro fertilization of eggs and/or sperm obtained from the transgenic animal. Where mating with a partner is to be performed, the partner may or may not be transgenic and/or a knockout; where it is transgenic, it may contain the same or a different transgene, or both. Alternatively, the partner may be a parental line. Where in vitro fertilization is used, the fertilized embryo may be implanted into a surrogate host or incubated in vitro, or both. Using either method, the progeny may be evaluated for the presence of the transgene using methods described above, or other appropriate methods.

In certain embodiments, a method of making a non-human, non-murine transgenic mammal having an ionic mechanism of cardiac cell excitation similar to that of humans and whose genome comprises a nucleic acid construct, wherein the construct comprises a mammalian cardiac β-MyHC promoter operably linked to cDNA sequence encoding a human mutant cardiac ion channel gene implicated in long QT syndrome (LQTS), comprises the steps of: transferring said nucleic acid construct to a zygote; allowing said zygote to develop to term; obtaining a non-human, non-murine mammal whose genome comprises the nucleic acid construct; breeding said mammal with a non-transgenic non-human, non-murine mammal to obtain F.sub.1 offspring and selecting a mammal whose genome comprises the nucleic acid construct, wherein said mammal expresses a human mutant cardiac ion channel gene implicated in long QT syndrome (LQTS).

The transgenic animals produced in accordance with the present invention will include exogenous genetic material. As set out above, the exogenous genetic material will, in certain embodiments, be a DNA sequence which results in the production of a target mutant. Further, in such embodiments the sequence will be attached to a transcriptional control element, e.g., a promoter, which preferably allows the expression of the transgene product in a specific type of cell.

Genetic techniques, which allow for the expression of transgenes can be regulated via site-specific genetic manipulation in vivo, are known to those skilled in the art. It may be appreciated by one skilled in the art that use of recombinant DNA technologies can improve expression of transgenes disclosed herein by manipulating, for example, the number of copies of the nucleic acid molecules integrated into a host cell, the efficiency with which those nucleic acid molecules are transcribed, the efficiency with which the resultant transcripts are translated, and the efficiency of post-translational modifications. Recombinant techniques useful for increasing the expression of nucleic acid molecules of the present invention include, but are not limited to, substitutions or modifications of expression control signals (e.g., promoters, operators, enhancers), substitutions or modifications of translational control signals (e.g., ribosome binding sites, Shine-Dalgarno sequences) and deletion of sequences that destabilize transcripts.

A transgene can encode the wild-type form of the protein, a mutant form of the protein or can encode homologs thereof, including both agonists and antagonists, as well as antisense constructs. In preferred embodiments, the expression of the transgene is restricted to specific subsets of cells, tissues or developmental stages utilizing, for example, cis-acting sequences that control expression in the desired pattern. In the present invention, such mosaic expression of a target protein can be essential for many forms of lineage analysis and can additionally provide a means to assess the effects of, for example, lack of target expression which might grossly alter development in small patches of tissue within an otherwise normal embryo. Toward this end, tissue-specific regulatory sequences and conditional regulatory sequences can be used to control expression of the transgene in certain spatial patterns. Moreover, temporal patterns of expression can be provided by, for example, conditional recombination systems or prokaryotic transcriptional regulatory sequences.

Figure 4:
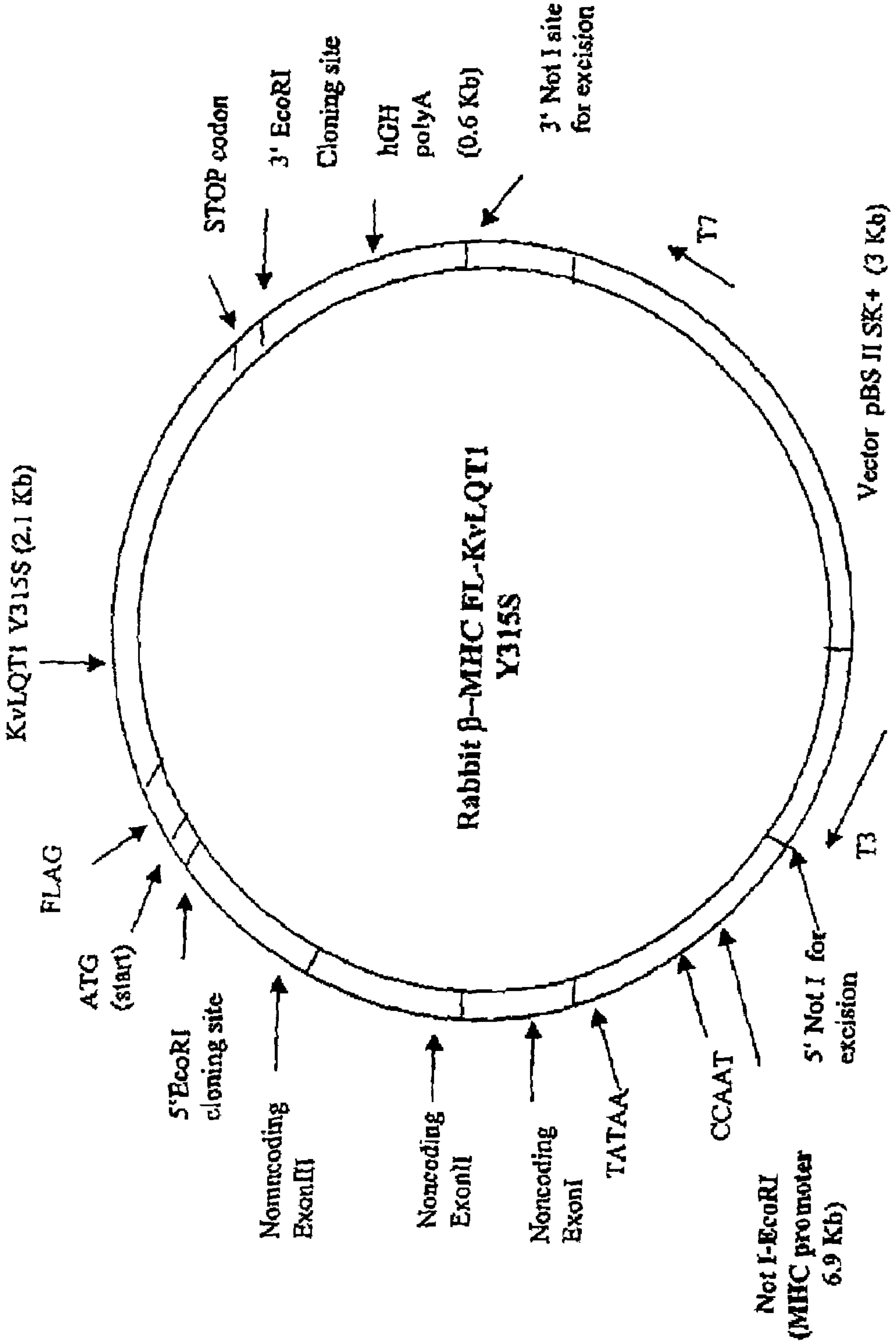
FIG. 4 depicts a construct comprising a FLAG-KvLQT1 Y315S mutant K+ channel subunit and a rabbit β-MyHC promoter used to create the transgenic KvLQT1 dominant negative (KvLQT1-DN) rabbits.

In certain embodiments, DNA constructs and vectors containing such constructs for preparing a non-human, non-murine transgenic mammal of the invention comprise a β-MyHC promoter and a wild-type or mutant cardiac ion channel gene selected from the group consisting of: KvLQT1 (KCNQ1), HERG (KCNH2), SCN5A, KCNE1, MiRP1, Kir2.1 (KCNJ2) and Ankyrin B. In certain embodiments, the promoter is operably linked to the ion channel gene. FIGS. 3 and 4 depicts the constructs used to create the KvLQT1-DN and ERG-DN rabbits of the present invention, which constructs are also embodiments of the present invention.

4. Cells, Cell Lines, Tissues and Samples from Non-Human, Non-Murine Transgenic Animal Models The invention further provides cells, cell lines, tissues and samples derived or prepared from the above-described transgenic animals. Such cells, cell lines, tissues and samples may be used as models for various cardiac disorders in which the cardiac ion channel mechanism is impaired or disrupted and used with any of the gene expression profiling, therapeutic screening, and diagnostic methods described herein. Methods of isolating cells, tissues and samples as well as the preparation of cell lines are well-known in the art.

The tissues of the animal which is the object of this invention may be utilized both as sources of cells for in vitro culture by means of standard culturing techniques, as well as "samples" within the meaning given it herein. In certain embodiments, a "tissue" as defined herein is a ventricular wedge preparation, the preparation of which is described in the Exemplification.

Culturing techniques make it possible to obtain primary cultures of cells which can be utilized directly as nontransformed lines for the screening of substances with activity, or can be transformed in order to obtain lines whose cells continue to proliferate, e.g. in an immortalized cell line. These cultures can be used, for example, in the screening of compounds with a therapeutic effect on LQTS, or for gene expression analysis, according the methods of the present invention. Such primary and immortalized cell cultures comprise the "cell lines" of the present invention.

Such cell lines may be prepared from any cell derived from a transgenic animal provided herein. In embodiments, the cells are derived from the heart of a transgenic animal. In certain embodiments, the cell line is prepared from myocytes.

A myocyte may be obtained from an animal or may be cultured from an embryo of an animal. The animal is preferably a mammal, such as a mouse or a rat, or an animal from which myocytes may be easily obtained, such as a chick. In certain embodiments, the myocyte is a cardiac myocyte such as an adult ventricular myocyte or a ventricular myocyte obtained by culturing a ventricular cell obtained from an embryo.

Preparation of a myocyte cell suspension may be based on methods outlined in Chien et al., J. Clin. Invest., 75: 1770-1780 (1985) and Iwaki et al., Circulation 1993 June; 87(6): 2023-32). Exemplary published methods for plating and culturing cardiac myocytes are as follows: Thum, et al. Xenobiotica 2000 November; 30(11):1063-77; Van Winkle, et al. In Vitro Cell Dev Biol Anim 1996 September; 32(8): 478-85; Jacobson, et al. Basic Res Cardiol 1985; 80 Suppl 1:79-82. Methods for producing cardiac myocyte cell lines which actively proliferate in culture while maintaining the differentiated phenotype are known in the art and have been described in, for example, Kimes and Brandt, Exp. Cell Res 98:367-381 (1976); Jaffredo, et al. Exp. Cell Res. 192:481-491 (1991); Eisenberg, Anat. Rec. 232:30A (1992); and Wang, et al. In Vitro Cell. Dev. Biol. 27:63-74 (1991).

The invention also includes a recombinant myocyte comprising at least one introduced nucleic acid. Such a recombinant myocyte may be prepared from a myocyte from a normal animal, and then a nucleic acid may be introduced. The introduced nucleic acid is constructed such that it is expressed in the myocyte. Innumerable nucleic acid expression constructs are known in the art, and the introduced nucleic acid(s) may comprise essentially any such construct. The recombinant myocyte may be made by preparing a nucleic acid vector comprising the introduced nucleic acid and delivering the nucleic acid vector to an animal myocyte. Any known method of preparing a nucleic acid vector and any known method of transforming or transfecting an animal cell using the vector may be used. By way of example, the vector may be the plasmid designated pcDNA3, the recombinant gene may be incorporated into the plasmid using standard molecular biology techniques, and a chick embryonic ventricular myocyte may be transfected using the plasmid by performing the modified calcium phosphate transfection method described by Xu et al., (1992, Nucl. Acids Res. 20:6425-6426). In certain embodiments, the recombinant myocyte contains a mutant human cardiac ion channel gene implicated in LQTS, for example, KvLQT1 (KCNQ1), HERG (KCNH2), SCN5A, KCNE1, MiRP1, Kir2.1 (KCNJ2) and Ankyrin B. In some embodiments, the plasmid may be pBS II SK.

The above-described cell lines and cell cultures may be cultured using well-known techniques of cell culture. Suitable media for culture include natural media based on tissue extracts and bodily fluids as well chemically defined media. Media suitable for use with the present invention include media containing serum as well as media that is serum-free. Serum may be from any source, including calf, fetal bovine, horse, and human serum. Any selected medium may contain one or more of the following in any suitable combination: basal media, water, buffers, free-radical scavengers, detergents, surfactants, polymers, cellulose, salts, amino acids, vitamins, carbon sources, organic supplements, hormones, growth factors, antibiotics, nutrients and metabolites, lipids, minerals, and inhibitors. Media may be selected or developed so that a particular pH, $CO_2$ tension, oxygen tension, osmolality, viscosity, and/or surface tension results from the composition of the medium. The incubation steps of the above method may be accomplished by maintaining the cell cultures in an environment wherein temperature and atmosphere are controlled. The culture conditions may be altered to maintain cellular proliferation and contractile activity in the cell cultures (optimum culture conditions are described below).

Cells, tissues, or other samples taken from the transgenic animals may be used in a variety of methods according to the present invention. Tissues and samples may be extracted from the animals using a variety of methods known in the art, for example, surgical resection, withdrawal of blood or other bodily fluid, urine collection, swabbing, and the like. Examples of experiments that can be performed to evaluate the cells and/or tissues and or samples from the animals include, but are not limited to, morphological examination of cardiac cells; histological examination of coronary vessels, of heart sections, of myocytes and/or of myofibrils; evaluation of cardiac myocyte DNA replication and/or expression; assays to evaluate enzyme activity; and assays studying programmed cell death, or apoptosis. The methods to perform such experiments are standard and are well known in the art.

5. Methods of Identifying Genes Involved in LQTS

The present invention relates to methods of identifying expression of genes involved in LQTS. In certain embodiments, a method of identifying genes that are involved in LQTS may comprise (a) analyzing the expression of at least one gene in a non-human, non-murine transgenic mammal, and in certain embodiments may further comprise: (b) subjecting said mammal to a stress; and (c) analyzing the expression of at least one gene in said mammal subsequent to said subjecting step. In certain embodiments, the method may still further comprise: (d) comparing the expression of the at least one gene analyzed before and after said subjecting step. In certain embodiments, more than one non-human, non-murine transgenic mammal may be used in the methods of the invention. In certain embodiments, each transgenic mammal has a different human gene involved in LQTS in its genome. In certain embodiments, the transgenic mammals have the same human gene involved in LQTS in their genomes.

The methods of identifying gene expression may be conducted using a cell, cell line, tissue or sample as described above. The stress may in certain embodiments be a physical stress, such as electrical stimulation, or may be a drug-induced stress, e.g. by administering a drug to the animal or culturing a cell or tissue derived therefrom in the presence of a drug. Exemplary drugs that may be used include, but are not limited to, α-adrenoreceptor agonists including methoxamine, prazosin, ephedrine, pseudoephedrine, phenylpropanolamine, midodrine, phenylephrine, methylphenidate and dextroamphetamine sulphate, β-adrenoreceptor agonists such as isoproterenol, propanolol, and channel blocking drugs (e.g., blockers of calcium, potassium, and sodium ion channels) such as sodium or potassium channel blockers such as lidocaine, ibutilide, mexiletine, propafenon, clofilium and hydroxylamine sotalol, amiodarone, Norpace, quinidine, calcium channel blockers such as amlodipine, bepridil, diltiazem, felodipine, flunarizine, isradipine, mibefradil, nicardipine, nifedipine, nimodipine, nisoldipine, nivaldipine, verapamil, sodium channel blockers such as benzothialzole, phenyl benzothialzole, disopyramide, propafenone, flecainide, lorcainide, aprindine, encainide, GEA-968, azure A, pancuronium, N-methylstrychnine, CNS 1237, BW1003C87, BW619C89, U54494A, PD85639, ralitoline, C1953, lifarizine, zonisamide and riluzole. Other drugs may include antibiotics such as erythromycin and anti histamines such as seldane, as well as new drugs to be screened for proarrhythmic effects.

Expression of the genes may be evaluated by methods known to those of skill in the art, for example, gene profiling methods. A person of skill in the art will recognize that in certain screening assays, it will be sufficient to assess the level of expression of a single gene and that in others, the expression of two or more is preferred, whereas still in others, the expression of essentially all the genes involved in a particular cellular activity is preferably assessed. Likewise, it will be sufficient to assess the activity of a single protein in some screening assays, whereas in others, the activities of multiple proteins may be assessed. Such assays are well-known to one of skill in the art and may be adapted to the methods of the present invention with no more than routine experimentation.

5.1. Gene Profiling

In one aspect, the methods of the present invention will comprise gene profiling methods using arrays. Arrays are often divided into microarrays and macroarrays, where microarrays have a much higher density of individual probe species per area. Microarrays may have as many as 1000 or more different probes in a 1 $cm^2$ area. There is no concrete cut-off to demarcate the difference between micro- and macroarrays, and both types of arrays are contemplated for use with the invention.

Microarrays are known in the art and generally consist of a surface to which probes that correspond in sequence to gene products (e.g., cDNAs, mRNAs, oligonucleotides) are bound at known positions. In one embodiment, the microarray is an array (e.g., a matrix) in which each position represents a discrete binding site for a product encoded by a gene (e.g., a protein or RNA), and in which binding sites are present for products of most or almost all of the genes in the organism's genome. In certain embodiments, the binding site or site is a nucleic acid or nucleic acid analogue to which a particular cognate cDNA can specifically hybridize. The nucleic acid or analogue of the binding site may be, e.g., a synthetic oligomer, a full-length cDNA, a less-than full length cDNA, or a gene fragment.

Generally, determining expression profiles with microarrays involves the following steps: (a) obtaining a mRNA sample from a subject and preparing labeled nucleic acids therefrom (the "target nucleic acids" or "targets"); (b) contact of the target nucleic acids with the array under conditions sufficient for target nucleic acids to bind with corresponding probe on the array, e.g. by hybridization or specific binding; (c) optional removal of unbound targets from the array; and (d) detection of bound targets, and analysis of the results, e.g., using computer based analysis methods. As used herein, "nucleic acid probes" or "probes" are nucleic acids attached to the array, whereas "target nucleic acids" are nucleic acids that are hybridized to the array.

There are various ways to perform each of the above steps, which are well-known to one of skill in the art. Such techniques are widely described in the literature. See, for example, Brady, G. (2000) *Expression profiling of single mammalian cells—small is beautiful*. Yeast 17:211-217; Hegde P, et al. (2000) *A concise guide to cDNA microarray analysis*. BioTechniques 29: 548-562; Scheidl S J, Nilsson S, Kalén M, Hellström M, Takemoto M, Håakansson J, and Lindahl P. (2002) mRNA Expression Profiling of Laser Microbeam Microdissected Cells from Slender Embryonic Structures. Am J Pathol 160:801-813; Schulze A, and Downward J. (2001) *Navigating gene expression using microarrays—a technology review*. Nature Cell Biology 3:E190-E195; Siedow J N. (2001) *Making sense of microarrays*. Genome Biology 2(2): Reports 4003; Van Berkum N L, Holstege F C. (2001) *DNA microarrays: raising the profile*. Curr Opin Biotechnol 12(1):48-52; Rajeevan M S, Vernon S D, Taysavang N, and Unger E R. (2001) *Validation of array-based gene expression profiles by real-time (kinetic)* RT-PCR. Journal of Molecular Diagnostics 3(1): 26-31; Pradet-Balade B, Boulmé F, Müllner E W, and Garcia-Sanz J A. (2001) *Reliability of mRNA Profiling: Verification for Samples with Different Complexities*. BioTechniques 31:1352-1357; Yue H, et al. (2001) *An evaluation of the performance of cDNA microarrays for detecting changes in global mRNA expression*. Nuc. Acids. Res. 29(8): e41; and Zarrinkar P P, et al. (2001) *Arrays of arrays for high-throughput gene expression profiling*. Genome Research 11:1256-1261

5.2 Other Methods for Determining Gene Expression Levels

In certain embodiments, it is sufficient to determine the expression of one or only a few genes, as opposed to hundreds or thousands of genes. Although microarrays may be used in these embodiments, various other methods of detection of gene expression are available. This section describes a few exemplary methods for detecting and quantifying mRNA or polypeptide encoded thereby. Where the first step of the methods includes isolation of mRNA from cells, this step may be conducted as described above. Labeling of one or more nucleic acids may be performed as described above.

In one embodiment, mRNA obtained from a sample is reverse transcribed into a first cDNA strand and subjected to PCR, e.g., RT-PCR. House keeping genes, or other genes whose expression does not vary may be used as internal controls and controls across experiments. Following the PCR reaction, the amplified products may be separated by electrophoresis and detected. By using quantitative PCR, the level of amplified product will correlate with the level of RNA that was present in the sample. The amplified samples may also be separated on an agarose or polyacrylamide gel, transferred onto a filter, and the filter hybridized with a probe specific for the gene of interest. Numerous samples may be analyzed simultaneously by conducting parallel PCR amplification, e.g., by multiplex PCR.

In another embodiment, mRNA levels is determined by dotblot analysis and related methods (see, e.g., G. A. Beltz et al., in Methods in Enzymology, Vol. 100, Part B, R. Wu, L. Grossmam, K. Moldave, Eds., Academic Press, New York, Chapter 19, pp. 266-308, 1985). In one embodiment, a specified amount of RNA extracted from cells is blotted (i.e., non-covalently bound) onto a filter, and the filter is hybridized with a probe of the gene of interest. Numerous RNA samples may be analyzed simultaneously, since a blot may comprise multiple spots of RNA. Hybridization is detected using a method that depends on the type of label of the probe. In another dotblot method, one or more probes of one or more genes involved in LQTS are attached to a membrane, and the membrane is incubated with labeled nucleic acids obtained from and optionally derived from RNA of a cell or tissue of a subject. Such a dotblot is essentially an array comprising fewer probes than a microarray.

"Dot blot" hybridization gained wide-spread use, and many versions were developed (see, e.g., M. L. M. Anderson and B. D. Young, in Nucleic Acid Hybridization-A Practical Approach, B. D. Hames and S. J. Higgins, Eds., IRL Press, Washington D.C., Chapter 4, pp. 73-111, 1985).

Another format, the so-called "sandwich" hybridization, involves covalently attaching oligonucleotide probes to a solid support and using them to capture and detect multiple nucleic acid targets (see, e.g., M. Ranki et al., Gene, 21, pp. 77-85, 1983; A. M. Palva, T. M. Ranki, and H. E. Soderlund, in UK Patent Application GB 2156074A, Oct. 2, 1985; T. M. Ranki and H. E. Soderlund in U.S. Pat. No. 4,563,419, Jan. 7, 1986; A. D. B. Malcolm and J. A. Langdale, in PCT WO 86/03782, Jul. 3, 1986; Y. Stabinsky, in U.S. Pat. No. 4,751, 177, Jan. 14, 1988; T. H. Adams et al., in PCT WO 90/01564, Feb. 22, 1990; R. B. Wallace et al. 6 Nucleic Acid Res. 11, p. 3543, 1979; and B. J. Connor et al., 80 Proc. Natl. Acad. Sci. USA pp. 278-282, 1983). Multiplex versions of these formats are called "reverse dot blots."

mRNA levels may also be determined by Northern blots. Specific amounts of RNA are separated by gel electrophoresis and transferred onto a filter which is then hybridized with a probe corresponding to the gene of interest. This method, although more burdensome when numerous samples and genes are to be analyzed provides the advantage of being very accurate.

A preferred method for high throughput analysis of gene expression is the serial analysis of gene expression (SAGE) technique, first described in Velculescu et al. (1995) *Science* 270, 484-487. Among the advantages of SAGE is that it has the potential to provide detection of all genes expressed in a given cell type, provides quantitative information about the relative expression of such genes, permits ready comparison of gene expression of genes in two cells, and yields sequence information that may be used to identify the detected genes. Thus far, SAGE methodology has proved itself to reliably detect expression of regulated and nonregulated genes in a variety of cell types (Velculescu et al. (1997) *Cell* 88, 243-251; Zhang et al. (1997) *Science* 276, 1268-1272 and Velculescu et al. (1999) *Nat. Genet.* 23, 387-388.

Techniques for producing and probing nucleic acids are further described, for example, in Sambrook et al., "Molecular Cloning: A Laboratory Manual" (New York, Cold Spring Harbor Laboratory, 1989).

Alternatively, the level of expression of one or more genes is determined by in situ hybridization. In one embodiment, a tissue sample is obtained from a subject, the tissue sample is sliced, and in situ hybridization is performed according to methods known in the art, to determine the level of expression of the genes of interest.

In other methods, the level of expression of a gene is detected by measuring the level of protein encoded by the gene. This may be done, e.g., by immunoprecipitation, ELISA, or immunohistochemistry using an agent, e.g., an antibody, that specifically detects the protein encoded by the gene. Other techniques include Western blot analysis. Immunoassays are commonly used to quantitate the levels of proteins in cell samples, and many other immunoassay techniques are known in the art. The invention is not limited to a particular assay procedure, and therefore is intended to include both homogeneous and heterogeneous procedures. Exemplary immunoassays which may be conducted according to the invention include fluorescence polarization immunoassay (FPIA), fluorescence immunoassay (FIA), enzyme immunoassay (EIA), nephelometric inhibition immunoassay (NIA), enzyme linked immunosorbent assay (ELISA), and radioimmunoassay (RIA). An indicator moiety, or label group, may be attached to the subject antibodies and is selected so as to meet the needs of various uses of the method which are often dictated by the availability of assay equipment and compatible immunoassay procedures. General techniques to be used in performing the various immunoassays noted above are known to those of ordinary skill in the art.

In the case of polypeptides which are secreted from cells, the level of expression of these polypeptides may be measured in biological fluids.

6. Genes and Gene Products

The present invention also relates to novel genes and/or the encoded gene products identified as being involved in LQTS. Such genes may be directly regulating or regulated by a cardiac ion channel gene or gene product or along a pathway in which the cardiac ion channel gene is trafficked to the membrane or in the membrane associated macromolecular complex that contains cardiac ion channels. The present invention also relates to novel panels of molecular targets comprised of groups of genes and/or the encoded gene products affected by a cardiac ion channel mutation and involved in LQTS. The novel panels of the present invention may also be comprised of the gene products of the panel genes, for example, mRNAs and proteins.

Such genes, for example, may be responsible for certain symptoms of LQTS. In certain embodiments, such genes may comprise the pathophysiologic pathways that regulate the depolarization and repolarization phases, trigger calcium release in individual myocytes, and govern the conduction and coordinated contractile function of the heart.

Genes and/or gene products involved in LQTS discovered using the animals and methods described may be used to develop probes derived from them to produce microarrays and other similar compositions. In one embodiment of the present invention, the composition is a microarray. There may be one or more than one probe corresponding to each gene on a microarray. For example, a microarray may contain from 2 to 20 probes corresponding to one gene and preferably about 5 to 10. The probes may correspond to the full length RNA sequence or complement thereof of genes involved in LQTS, or they may correspond to a portion thereof, which portion is of sufficient length for permitting specific hybridization. Such probes may comprise from about 50 nucleotides to about 100, 200, 500, or 1000 nucleotides or more than 1000 nucleotides. As further described herein, microarrays may contain oligonucleotide probes, consisting of about 10 to 50 nucleotides, preferably about 15 to 30 nucleotides and even more preferably 20-25 nucleotides. The probes are preferably single stranded. The probe will have sufficient complementarity to its target to provide for the desired level of sequence specific hybridization. Microarrays may be prepared by methods known in the art, as described below, or they may be custom made by companies, e.g., Affymetrix (Santa Clara, Calif.).

Arrays preferably include control and reference nucleic acids. Control nucleic acids are nucleic acids which serve to indicate that the hybridization was effective. Reference nucleic acids allow the normalization of results from one experiment to another, and to compare multiple experiments on a quantitative level. Exemplary reference nucleic acids include housekeeping genes of known expression levels, e.g., GAPDH, hexokinase and actin. Mismatch controls may also be provided for the probes to the target genes, for expression level controls or for normalization controls. Mismatch controls are oligonucleotide probes or other nucleic acid probes identical to their corresponding test or control probes except for the presence of one or more mismatched bases.

Arrays may also contain probes that hybridize to more than one allele of a gene. For example the array may contain one probe that recognizes allele 1 and another probe that recognizes allele 2 of a particular gene.

The construction of solid phase nucleic acid arrays to detect target nucleic acids is well described in the literature. See, Fodor et al. (1991) Science, 251: 767-777; Sheldon et al. (1993) Clinical Chemistry 39(4): 718-719; Kozal et al. (1996) Nature Medicine 2(7): 753-759 and Hubbell U.S. Pat. No.

5,571,639; Pinkel et al. PCT/US95/16155 (WO 96/17958); U.S. Pat. Nos. 5,677,195; 5,624,711; 5,599,695; 5,451,683; 5,424,186; 5,412,087; 5,384,261; 5,252,743 and 5,143,854; PCT Patent Publication Nos. 92/10092 and 93/09668; and PCT WO 97/10365.

cDNA probes may be prepared according to methods known in the art and further described herein, e.g., reverse-transcription PCR (RT-PCR) of RNA using sequence specific primers. Oligonucleotide probes may be synthesized chemically. Sequences of the genes or cDNA from which probes are made may be obtained, e.g., from GenBank, other public databases or publications.

Nucleic acid probes may be natural nucleic acids, chemically modified nucleic acids, e.g., composed of nucleotide analogs, as long as they have activated hydroxyl groups compatible with the linking chemistry. A nucleic acid probe may be at least about 10 nucleotides long, preferably at least about 15, 20, 25, 30, 50, 100 nucleotides or more, and may comprise the full length gene. If the nucleic acid is short (i.e., 20 nucleotides or less), the sequence is preferably perfectly complementary to the target gene (i.e., a gene that is involved in LQTS), such that specific hybridization may be obtained. However, nucleic acids, even short ones, that are not perfectly complementary to the target gene may also be included in a composition of the invention, e.g., for use as a negative control. Certain compositions may also comprise nucleic acids that are complementary to, and capable of detecting, an allele of a gene.

The probes may be attached to a solid support, such as paper, membranes, filters, chips, pins or glass slides, or any other appropriate substrate, such as those further described herein. For example, probes of genes involved in LQTS may be attached covalently or non covalently to membranes for use, e.g., in dotblots, or to solids such as to create arrays, e.g., microarrays.

Arrays, e.g., microarrrays, may conveniently be stored following fabrication or purchase for use at a later time. Under appropriate conditions, the subject arrays are capable of being stored for at least about 6 months and may be stored for up to one year or longer. Arrays are generally stored at temperatures between about −20° C. to room temperature, where the arrays are preferably sealed in a plastic container, e.g. bag, and shielded from light.

In another embodiment, the invention provides a composition comprising a plurality of agents which may detect a polypeptide encoded by a gene involved in LQTS. An agent may be, e.g., an antibody. Antibodies to polypeptides described herein may be obtained commercially, or they may be produced according to methods known in the art.

7. Safety Screening for Therapeutics which Adversely Affect Normal Subjects or Subjects Susceptible to Developing LQTS when Receiving Drugs that Suppress the Function of IKr Currents in the Heart More than 40 marketed drugs have been associated with $K^+$ channel block, QT prolongation and TdP. Heightened regulatory awareness has had significant impact on drug development schedules, approval and labeling. If done early, non-clinical safety testing can identify potentially lethal drugs and produce large savings in invested time & development costs. Drug-induced QT prolongation is a serious complication of drugs due to impaired repolarization and is associated with an increased risk of lethal ventricular arrhythmias. It is almost always associated with block of HERG. A 50-100 millisecond increase in QTc may indicate risk of ventricular arrhythmia particularly TdP. However, the incidence of TdP is too low to be detected in phase III clinical trials.

Thus, in both normal individuals and individual susceptible to developing drug-induced LQTS, certain therapeutic agents can induce or exacerbate symptoms of LQTS, and may lead to sudden death. The transgenic animal models provided herein, and in particular the transgenic animal models for LQT1 (KvLQT1-DN) provided herein may be used to screen existing therapeutics as well as novel therapeutics to identify those that would have adverse affects in normal patients or patients susceptible to develop LQTS via suppression the expression or blocking the function of $I_{Kr}$ (HERG). This is the most frequent cause of drug-induced sudden death and has resulted in the withdrawal of several drugs from the market. The transgenic animal (ERG-DN) may be used to screen existing therapeutics as well as novel therapeutics that may suppress the expression of KCNQ1. Indeed, many of the ERG-DN rabbits die suddenly between the age of 6 to 8 months, as estimated by Kaplan-Meier survival analysis.

Accordingly, one aspect of the present invention is to provide methods for screening for various candidate therapeutics and compounds for their ability to induce LQTS and arrhythmia. In certain embodiments, a method of identifying compounds that cause at least one symptom associated with LQTS may comprise: (a) administering a candidate compound to a non-human, non-murine transgenic mammal of the invention; and (b) evaluating whether said administration induces at least one symptom associated with LQTS. The symptom may be, for example, arrhythmia, death, TdP, long QT intervals, broad-based T waves and transmural dispersion of repolarization. Measurement of such symptoms is well-known to one of skill in the art, and certain measurements are described in more detail in the Exemplification. In certain embodiments, KvLQT1-DN rabbits will like be very sensitive to compounds that block HERG in humans and therefore can be used to screen new compounds for proarrhythmic effect.

Any existing or novel therapeutic or compound in any formulation may be used with the methods of the present invention.

Therapeutics or compounds to be tested using the methods of the present invention may be formulated into compositions comprising a pharmaceutically efficient amount of the therapeutic or compound to be tested in a pharmaceutically acceptable carrier. Candidate therapeutics or compounds to be tested by the above methods may be formulated into pharmaceutical compositions, e.g. the composition intended to be sold or administered to patients.

The candidate therapeutics or compounds of the present invention may be administered by various means, depending on their intended use, as is well known in the art. For example, if the candidate therapeutics or compounds are to be administered orally, they may be formulated as tablets, capsules, granules, powders or syrups. Alternatively, the candidate therapeutics or compounds may be administered parenterally as injections (intravenous, intramuscular or subcutaneous), drop infusion preparations or suppositories. For application by the ophthalmic mucous membrane route, candidate therapeutics or compounds may be formulated as eyedrops or eye ointments. These formulations may be prepared by conventional means, and, if desired, the candidate therapeutics or compounds may be mixed with any conventional additive, such as an excipient, a binder, a disintegrating agent, a lubricant, a corrigent, a solubilizing agent, a suspension aid, an emulsifying agent or a coating agent.

In formulations of the candidate therapeutics or compounds, wetting agents, emulsifiers and lubricants, such as sodium lauryl sulfate and magnesium stearate, as well as coloring agents, release agents, coating agents, sweetening, flavoring and perfuming agents, preservatives and antioxidants may be present in the formulated agents.

Candidate therapeutics or compounds may be suitable for oral, nasal, topical (including buccal and sublingual), rectal, vaginal, aerosol and/or parenteral administration. The formulations may conveniently be presented in unit dosage form and may be prepared by any methods well known in the art of pharmacy. The amount of agent that may be combined with a carrier material to produce a single dose vary depending upon the subject being treated, and the particular mode of administration.

Methods of preparing these formulations include the step of bringing into association agents of the present invention with the carrier and, optionally, one or more accessory ingredients. In general, the formulations are prepared by uniformly and intimately bringing into association agents with liquid carriers, or finely divided solid carriers, or both, and then, if necessary, shaping the product.

Examples of suitable aqueous and non-aqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity may be maintained, for example, by the use of coating materials, such as lecithin, by the maintenance of the required particle size in the case of dispersions, and by the use of surfactants.

In certain embodiments, a range of dosages of a candidate therapeutic or compound may be tested for safety using the transgenic animals and testing methods provided herein. In certain embodiments, a range of dosages is tested.

The dosage of any candidate therapeutics or compounds will vary depending on the symptoms, age and body weight of the patient in which they are to be used, the nature and severity of the disorder to be treated or prevented, the route of administration, and the form of the supplement. Any of the candidate therapeutics or compounds may be administered in a single dose or in divided doses. Dosages for the candidate therapeutics or compounds may be readily determined by techniques known to those of skill in the art or as taught herein. Also, mixtures of more than one candidate therapeutic or compound, as well as other therapeutic agents, may be tested using the transgenic animals and testing methods of the invention.

The precise time of administration and amount of any particular candidate therapeutic or compound that will yield the most effective treatment in a given patient will depend upon the activity, pharmacokinetics, and bioavailability of a particular compound, physiological condition of the patient (including age, sex, disease type and stage, general physical condition, responsiveness to a given dosage and type of medication), route of administration, and the like. The guidelines presented herein may be used to optimize the treatment to be tested for safety before testing it for safety, e.g., determining the optimum time and/or amount of administration, which will require no more than routine experimentation consisting of monitoring the subject and adjusting the dosage and/or timing.

The candidate therapeutics may also be screened for safety using cells, adherent or nonadherent cell lines, tissues, and samples from the subject transgenic mammals in in vitro methods. Such in vitro methods are well-known to those of skill in the art. For example, patch-clamp screening of channel activity in a cell, tissue, sample, etc., e.g. of HERG, may be performed. One example of a commercially available, automated patch-clamp assay is ChanTest's FASTpatch® assay.

Ion channel expression, activity and trafficking may also be monitored in cells, cell lines, tissues, and samples from the subject transgenic mammals to assess the safety of candidate therapeutic agents. For example, one such commercially available assay is ChanTest's HERG-Lite® chemiluminescent screening assay that monitors HERG expression at the cell surface and identifies both hERG channel blockers and hERG trafficking inhibitors. Other assays which may be used to assess candidate therapeutic safety in vitro include kinetic, cell-based intracellular calcium-signaling assays (such as monitoring of intracellular calcium, calcium release assays, etc), membrane potential assays, repolarization assays (i.e., measurements of concentration-response and rate-dependence of test articles on action potential parameters such as resting membrane potential (RMP, mV), action potential amplitude (APA, mV), maximum rate of rise (Vmax, V/s), and action potential duration at 60 and 90% repolarization (APD60 and APD90, ms)), concentration response assays, block comparator tests and gene block screens. Such assays are well-known to those skilled in the art and are described in detail, for example, at www.chantest.com.

Combinations of such assays may be used, e.g., in a battery of tests to determine a candidate's safety. For example, ChanTest's MICE Detection Assay (MDA) includes two components: the MDA I component of the assay combines a hERG concentration-response assay and a simultaneous Action Potential Duration (APD) assay to reveal the presence of MICE (Mixed Ion Channel Effects). If MICE are detected in MDA I, then the MDA II component of the assay simultaneously tests the 4 other primary cardiac ion channels (Na, Ca, KvLQT1/minK & Kv4.3) at the hERG IC50 (or multiple thereof) to determine the relative inhibitory potency versus the HERG channel, thereby identifying the cardiac ion channel(s) responsible for creating those mixed ion channel effects.

Dosages may be determined in vitro, for example, by determining a candidate's potential to impair cardiac repolarization. Drug concentrations, chosen to block current from 10 to 90%, may be applied to a cardiac ion channel of interest in a cell, tissue, sample, etc., e.g. HERG, KvLQT1, etc. Dose solution analysis may be used to verify applied concentrations with analytical sample testing of dose solutions.

Assays may be modified to accommodate automation of the assay and may be accomplished in any vessel suitable for containing the reactants. Examples include microtitre plates, test tubes, and micro-centrifuge tubes.

8. Methods of Screening for Therapeutic Compounds

The present invention further relates to the use of the transgenic mammals, cell line, tissues, and samples derived therefrom, as well as the novel genes, gene products, and panels of genes and gene products of the invention in methods of screening candidate therapeutic agents for use in inhibiting the progression of or preventing or treating LQTS. The compounds may modulate the expression or activity of genes or gene products involved in LQTS as described above.

In certain embodiments, a method of screening candidate therapeutic compounds for the treatment or prevention of LQTS, may comprise: (a) administering a candidate therapeutic compound to a non-human, non-murine transgenic mammal of the invention and (b) analyzing the effect of the compound. The analyzing step may comprise the evaluation of gene expression using a cell, tissue or sample from said mammal, wherein the effect of modulating gene expression indicates a potential therapeutic agent. In other embodiments, the analyzing step may comprise the physiological evaluation of the transgenic animal, wherein the effect of inhibiting a symptom of LQTS indicates a potential therapeutic agent. Symptoms that are evaluated may be, for example, arrhythmia, death, TdP, long QT intervals, broad-based T waves and transmural dispersion of repolarization, prolongation of action potential duration (APD) of cardiomyocytes as well as inducing EADs, and inhibiting $I_{Kr}$.

In other embodiments, a method of screening candidate therapeutic compounds for the treatment or prevention of LQTS may comprise (a) contacting a candidate therapeutic compound with a cell line, tissue or sample derived from a non-human, non-murine mammal of the invention; and (b) analyzing the effect of the compound. In certain embodiments, the analyzing step may comprise the evaluation of gene expression, wherein the effect of modulating gene expression indicates a potential therapeutic agent.

In still other embodiments, a method of screening candidate therapeutic compounds for the treatment or prevention of LQTS may comprise: (a) contacting a gene or gene product involved with LQTS with a candidate therapeutic compound; and (b) evaluating the ability of the compound to modulate the expression of the gene or activity of the gene product, wherein the ability to modulate expression or activity indicates a potential therapeutic agent.

In certain embodiments, candidate therapeutic compounds, or "therapeutics", are evaluated for their ability to inhibit the progression, reverse a symptom of, treat or prevent LQTS. In certain embodiments, the candidate therapeutic will be evaluated for its ability to normalize the level of expression of a gene or group of genes in a transgenic mammal of the invention, cell line, tissues, or sample derived therefrom, that are involved in LQTS. In other embodiments, the candidate therapeutic will be evaluated for its ability to normalize the level of expression of a gene or group of genes selected from the panels of targets the invention in a subject at risk or suffering from LQTS. In certain embodiments, candidate therapeutics will be evaluated for their ability to affect certain physiological factors in a subject having LQTS or a transgenic mammal of the invention. If LQTS is treated or prevented by any of said compounds, the compound will be considered a therapeutic agent for LQTS.

In still other embodiments, candidate therapeutics, are evaluated for their ability to bind a target gene or gene product involved in LQTS. Alternatively, candidate therapeutic agents may be evaluated for their ability to modulate the activity of such genes or gene products by contacting the cells of a subject with said candidate therapeutic agents. In certain embodiments, a candidate therapeutic may be evaluated for its ability to inhibit the activity of a protein that normally promotes LQTS. In this embodiment, a candidate therapeutic agent that exhibits the ability to inhibit the protein's activity may be considered a candidate therapeutic for treating LQTS. In certain embodiments, a candidate therapeutic may be evaluated for its ability to inhibit a gene that normally promotes LQTS. In this embodiment, a candidate therapeutic agent that exhibits the ability to inhibit the gene may be considered a candidate therapeutic for treating LQTS. In still other embodiments, a candidate therapeutic may be evaluated for its ability to promote the activity of a protein or gene whose inactivity is thought to promote LQTS. In these embodiments, a candidate therapeutic agent that exhibits the ability to promote the activity of the protein or gene may be considered a candidate therapeutic for treating LQTS.

Furthermore, a candidate therapeutic may be evaluated for its ability to normalize the level of turnover of a protein encoded by a gene involved in LQTS. In another embodiment, a candidate therapeutic may be evaluated for its ability to normalize the translational level of a protein encoded by a gene involved in LQTS. In yet another embodiment, a candidate therapeutic may be evaluated for its ability to normalize the level of turnover of an mRNA encoded by a gene involved in LQTS.

Assays and methods of developing assays appropriate for use in the methods described above are known to those of skill in the art, and are contemplated for use as appropriate with the methods of the present invention. In certain embodiments of the present invention, a candidate compound may be evaluated by an in vitro assay. In certain embodiments, the assay may be an in vivo assay. Assays may be conducted to identify molecules that modulate the expression and/or activity of a gene. Alternatively, assays may be conducted to identify molecules that modulate the activity of a protein encoded by a gene. Such assays are well-known to one of skill in the art and may be adapted to the methods of the present invention with no more than routine experimentation.

Compounds for use with the present invention may be selected from any of lipids, carbohydrates, peptides, peptidomimetics, peptide-nucleic acids (PNAs), proteins, small molecules, natural products, aptamers and oligonucleotides. Such compounds may be selected from a library of such compounds. The synthesis and screening of combinatorial libraries is a validated strategy for the identification and study of compounds of interest. According to the present invention, the synthesis of libraries containing molecules or compounds may be performed using established combinatorial methods for solution phase, solid phase, or a combination of solution phase and solid phase synthesis techniques. The synthesis of combinatorial libraries is well known in the art and has been reviewed (see, e.g., "Combinatorial Chemistry", *Chemical and Engineering News*, Feb. 24, 1997, p. 43; Thompson et al., *Chem. Rev.* (1996) 96:555). Many libraries are commercially available. One of ordinary skill in the art will realize that the choice of method for any particular embodiment will depend upon the specific number of molecules to be synthesized, the specific reaction chemistry, and the availability of specific instrumentation, such as robotic instrumentation for the preparation and analysis of the inventive libraries. In certain embodiments, the reactions to be performed to generate the libraries are selected for their ability to proceed in high yield, and in a stereoselective and regioselective fashion, if applicable.

All of the above screening methods may be accomplished using a variety of assay formats. In light of the present disclosure, those not expressly described herein will nevertheless be known and comprehended by one of ordinary skill in the art. The assays may identify compounds which are, e.g., either agonists or antagonists, of expression of a target gene of interest, or of a protein:protein or protein-substrate interaction of a target of interest, or of the role of target gene products in the pathogenesis of normal or abnormal cellular physiology, proliferation, and/or differentiation and disorders related thereto. The assays may further identify compounds which affect the generation of normal or abnormal cellular physiology, cell proliferation, and/or cell differentiation and disorders related thereto. Assay formats which approximate such conditions as formation of protein complexes or protein-nucleic acid complexes, enzymatic activity, and even specific signaling pathways in cardiac cells, may be generated in many different forms, and include but are not limited to assays based on cell-free systems, e.g. purified proteins or cell lysates, as well as cell-based assays which utilize intact cells.

8.1. In Vivo Methods

One aspect of the present invention provides methods for screening various compounds for their ability to inhibit the progression of, e.g., treat LQTS. Such methods are referred to within this section as in vivo as they involve the use of whole cells in culture or the use of the transgenic animals of the invention or samples taken therefrom. In an illustrative embodiment, the subject progenitor cells, and their progeny, can be used to screen various compounds. Such cells can be maintained in minimal culture media for extended periods of time (e.g., for 7-21 days or longer) and can be contacted with any compound, to determine the effect of such compound on one of cellular growth, proliferation or differentiation of progenitor cells in the culture. Detection and quantification of growth, proliferation or differentiation of these cells in response to a given compound provides a means for determining the compound's efficacy at inducing one of the growth, proliferation or differentiation in a given ductal explant. Methods of measuring cell proliferation are well known in the art and most commonly include determining DNA synthesis characteristic of cell replication. However, because cardiomyocytes do not significantly divide, measurement of protein synthesis is preferable. There are numerous methods in the art for measuring protein synthesis, any of which may be used according to the invention. In an embodiment of the invention, protein synthesis has been determined using a radioactive labeled amino acid (e.g., $^3$H-leucine) or labeled amino acid or amino acid analogues for detection by immunofluorescence. The efficacy of the compound can be assessed by generating dose response curves from data obtained using various concentrations of the compound. A control assay can also be performed to provide a baseline for comparison. Identification of the progenitor cell population(s) amplified in response to a given test compound can be carried out according to such phenotyping as described above.

In still further embodiments, a protein-protein, protein: substrate, or protein:nucleic acid interaction of interest is generated in whole cells, taking advantage of cell culture techniques to support the subject assay. For example, as described below, the interaction of interest may be constituted in a eukaryotic cell culture system, including mammalian and yeast cells. Advantages to generating the subject assay in an intact cell include the ability to detect inhibitors which are functional in an environment more closely approximating that which therapeutic use of the inhibitor would require, including the ability of the compound to gain entry into the cell. Furthermore, certain of the in vivo embodiments of the assay, such as examples given below, are amenable to high through-put analysis of candidate agents.

The components of the interaction of interest may be endogenous to the cell selected to support the assay. Alternatively, some or all of the components may be derived from exogenous sources. For instance, fusion proteins may be introduced into the cell by recombinant techniques (such as through the use of an expression vector), as well as by microinjecting the fusion protein itself or mRNA encoding the fusion protein.

In any case, the cell may be ultimately manipulated after incubation with a candidate inhibitor in order to facilitate detection of a protein-protein, protein:substrate, or protein: nucleic acid interaction-mediated signaling event (e.g. modulation of a post-translational modification of a protein-protein interaction component substrate, such as phosphorylation, modulation of transcription of a gene in response to cell signaling, etc.). As described above for assays performed in reconstituted protein mixtures or lysate, the effectiveness of a candidate inhibitor may be assessed by measuring direct characteristics of an interaction component, such as shifts in molecular weight by electrophoretic means or detection in a binding assay. For these embodiments, the cell will typically be lysed at the end of incubation with the candidate agent, and the lysate manipulated in a detection step in much the same manner as might be the reconstituted protein mixture or lysate, e.g., described above.

Indirect measurement of an interaction may also be accomplished, for example, by detecting a biological activity associated with a protein-protein interaction component that is modulated by a protein-protein interaction mediated signaling event. As set out above, the use of fusion proteins comprising a protein-protein interaction component polypeptide and an enzymatic activity are representative embodiments of the subject assay in which the detection means relies on indirect measurement of a protein-protein interaction component polypeptide by quantitating an associated enzymatic activity.

In other embodiments, the biological activity of a nucleic acid-protein, protein-substrate or protein-protein interaction component polypeptide may be assessed by monitoring changes in the phenotype of the targeted cell. For example, the detection means may include a reporter gene construct which includes a transcriptional regulatory element that is dependent in some form on the level of an interaction component or a interaction component substrate. The protein interaction component may be provided as a fusion protein with a domain which binds to a DNA element of the reporter gene construct. The added domain of the fusion protein may be one which, through its DNA-binding ability, increases or decreases transcription of the reporter gene. Whichever the case may be, its presence in the fusion protein renders it responsive to the protein-protein interaction-mediated signaling pathway. Accordingly, the level of expression of the reporter gene will vary with the level of expression of the protein interaction component.

The reporter gene product is a detectable label, such as luciferase, β-lactamase or β-galactosidase, and is produced in the intact cell. The label may be measured in a subsequent lysate of the cell. However, the lysis step is preferably avoided, and providing a step of lysing the cell to measure the label will typically only be employed where detection of the label cannot be accomplished in whole cells.

Moreover, in the whole cell embodiments of the subject assay, the reporter gene construct may provide, upon expression, a selectable marker. A reporter gene includes any gene that expresses a detectable gene product, which may be RNA or protein. Preferred reporter genes are those that are readily detectable. The reporter gene may also be included in the construct in the form of a fusion gene with a gene that includes desired transcriptional regulatory sequences or exhibits other desirable properties. For instance, the product of the reporter gene may be an enzyme which confers resistance to antibiotic or other drug, or an enzyme which complements a deficiency in the host cell (i.e. thymidine kinase or dihydrofolate reductase). To illustrate, the aminoglycoside phosphotransferase encoded by the bacterial transposon gene Tn5 neo may be placed under transcriptional control of a promoter element responsive to the level of a protein-protein interaction component polypeptide present in the cell. Such embodiments of the subject assay are particularly amenable to high through-put analysis in that proliferation of the cell may provide a simple measure of inhibition of an interaction.

Other examples of reporter genes include, but are not limited to CAT (chloramphenicol acetyl transferase) (Alton and Vapnek (1979), *Nature* 282: 864-869) luciferase, and other enzyme detection systems, such as β-galactosidase, β-lactamase, (G. Zlokarnik, et al. (1998) *Science,* 279:84-88); firefly luciferase (deWet et al. (1987), *Mol. Cell. Biol.* 7:725-737); bacterial luciferase (Engebrecht and Silverman (1984), *PNAS* 1: 4154-4158; Baldwin et al. (1984), *Biochemistry* 23: 3663-3667); alkaline phosphatase (Toh et al. (1989) *Eur. J. Biochem.* 182: 231-238, Hall et al. (1983) *J. Mol. Appl. Gen.* 2: 101), human placental secreted alkaline phosphatase (Cullen and Malim (1992) *Methods in Enzymol.* 216:362-368).

The amount of transcription from the reporter gene may be measured using any method known to those of skill in the art to be suitable. For example, specific mRNA expression may be detected using Northern blots or specific protein product may be identified by a characteristic stain, western blots or an intrinsic activity.

In preferred embodiments, the product of the reporter gene is detected by an intrinsic activity associated with that product. For instance, the reporter gene may encode a gene product that, by enzymatic activity, gives rise to a detection signal based on color, fluorescence, or luminescence.

The amount of expression from the reporter gene is then compared to the amount of expression in either the same cell in the absence of the test compound or it may be compared with the amount of transcription in a substantially identical cell that lacks a component of the interaction of interest.

8.2. In Vitro Methods

In many drug screening programs which test libraries of compounds and natural extracts, high throughput assays are desirable in order to maximize the number of compounds surveyed in a given period of time. Assays of the present invention which are performed in cell-free systems, such as may be derived with purified or semi-purified proteins or with lysates, are often preferred as "primary" screens in that they may be generated to permit rapid development and relatively easy detection of an alteration in a molecular target which is mediated by a test compound. Moreover, the effects of cellular toxicity and/or bioavailability of the test compound may be generally ignored in the in vitro system, the assay instead being focused primarily on the effect of the compound on the molecular target as may be manifest in an alteration of binding affinity with other proteins or changes in enzymatic properties of the molecular target. Accordingly, potential modifiers, e.g., activators or inhibitors of protein-substrate, protein-protein interactions or nucleic acid:protein interactions of interest may be detected in a cell-free assay generated by constitution of function interactions of interest in a cell lysate. Such protein-substrate, protein-protein, or nucleic acid:protein interactions of interest may be identified by the gene expression profiling methods described herein. In an alternate format, the assay may be derived as a reconstituted protein mixture which, as described below, offers a number of benefits over lysate-based assays.

In one aspect, the present invention provides assays that may be used to screen for compounds which modulate protein-protein interactions, nucleic acid-protein interactions, or protein-substrate interactions of interest. For instance, the drug screening assays of the present invention may be designed to detect agents which disrupt binding of protein-protein interaction binding moieties. In other embodiments, the subject assays will identify inhibitors of the enzymatic activity of a protein or protein-protein interaction complex. In a preferred embodiment, the compound is a mechanism based inhibitor which chemically alters one member of a protein-protein interaction or one chemical group of a protein and which is a specific inhibitor of that member, e.g. has an inhibition constant 10-fold, 100-fold, or more preferably, 1000-fold different compared to homologous proteins.

In one embodiment of the present invention, screening assays may be generated which detect inhibitory compounds on the basis of their ability to interfere with binding of components of a given protein-substrate, protein-protein, or nucleic acid-protein interaction of interest. In an exemplary binding assay, the compound of interest is contacted with a mixture generated from protein-protein interaction component polypeptides. Detection and quantification of expected activity from a given protein-protein interaction provides a means for determining the compound's efficacy at inhibiting (or potentiating) complex formation between the two polypeptides. The efficacy of the compound may be assessed by generating dose response curves from data obtained using various concentrations of the test compound. Moreover, a control assay may also be performed to provide a baseline for comparison. In the control assay, the formation of complexes is quantitated in the absence of the test compound.

Complex formation between component polypeptides, polypeptides and genes, or between a component polypeptide and a substrate may be detected by a variety of techniques, many of which are effectively described above. For instance, modulation in the formation of complexes may be quantitated using, for example, detectably labeled proteins (e.g. radiolabeled, fluorescently labeled, or enzymatically labeled), by immunoassay, or by chromatographic detection.

Accordingly, one exemplary screening assay of the present invention includes the steps of contacting a polypeptide or functional fragment thereof or a binding partner with a test compound or library of test compounds and detecting the formation of complexes. For detection purposes, the molecule may be labeled with a specific marker and the test compound or library of test compounds labeled with a different marker. Interaction of a test compound with a polypeptide or fragment thereof or binding partner may then be detected by determining the level of the two labels after an incubation step and a washing step. The presence of two labels after the washing step is indicative of an interaction.

An interaction between molecules may also be identified by using real-time BIA (Biomolecular Interaction Analysis, Pharmacia Biosensor AB) which detects surface plasmon resonance (SPR), an optical phenomenon. This technique is further described, e.g., in BIAtechnology Handbook by Pharmacia.

Another exemplary screening assay of the present invention includes the steps of (a) forming a reaction mixture including: (i) a polypeptide, (ii) a binding partner, and (iii) a test compound; and (b) detecting interaction of the polypeptide and the binding partner. The polypeptide and binding partner may be produced recombinantly, purified from a source, e.g., plasma, or chemically synthesized, as described herein. A statistically significant change (potentiation or inhibition) in the interaction of the polypeptide and binding partner in the presence of the test compound, relative to the interaction in the absence of the test compound, indicates a potential agonist (mimetic or potentiator) or antagonist (inhibitor) of polypeptide bioactivity for the test compound. The compounds of this assay may be contacted simultaneously. Alternatively, a polypeptide may first be contacted with a test compound for an appropriate amount of time, following which the binding partner is added to the reaction mixture. The efficacy of the compound may be assessed by generating dose response curves from data obtained using various concentrations of the test compound. Moreover, a control assay may also be performed to provide a baseline for comparison. In the control assay, isolated and purified polypeptide or binding partner is added to a composition containing the binding partner or polypeptide, and the formation of a complex is quantitated in the absence of the test compound.

Typically, it will be desirable to immobilize either polypeptide or its binding partner to facilitate separation of complexes from uncomplexed forms of one or both of the proteins, as well as to accommodate automation of the assay. Binding of polypeptide to a binding partner, may be accomplished in any vessel suitable for containing the reactants. Examples include microtitre plates, test tubes, and micro-centrifuge tubes. In one embodiment, a fusion protein may be provided which adds a domain that allows the protein to be bound to a matrix.

For processes that rely on immunodetection for quantitating one of the proteins trapped in the complex, antibodies against the protein, such as anti-polypeptide antibodies, may be used. Alternatively, the protein to be detected in the complex may be "epitope-tagged" in the form of a fusion protein which includes, in addition to the polypeptide sequence, a second polypeptide for which antibodies are readily available (e.g. from commercial sources). For instance, the GST fusion proteins described above may also be used for quantification of binding using antibodies against the GST moiety. Other useful epitope tags include myc-epitopes (e.g., see Ellison et al. (1991) J Biol Chem 266:21150-21157) which includes a 10-residue sequence from c-myc, as well as the pFLAG system (International Biotechnologies, Inc.) or the pEZZ-protein A system (Pharmacia, N.J.).

In certain in vitro embodiments of the present assay, the protein or the set of proteins engaged in a protein-protein, protein-substrate, or protein-nucleic acid interaction comprises a reconstituted protein mixture of at least semi-purified proteins. By semi-purified, it is meant that the proteins utilized in the reconstituted mixture have been previously separated from other cellular or viral proteins. For instance, in contrast to cell lysates, the proteins involved in a protein-substrate, protein-protein or nucleic acid-protein interaction are present in the mixture to at least 50% purity relative to all other proteins in the mixture, and more preferably are present at 90-95% purity. In certain embodiments of the subject method, the reconstituted protein mixture is derived by mixing highly purified proteins such that the reconstituted mixture substantially lacks other proteins (such as of cellular or viral origin) which might interfere with or otherwise alter the ability to measure activity resulting from the given protein-substrate, protein-protein interaction, or nucleic acid-protein interaction.

Assaying biological activity resulting from a given protein-substrate, protein-protein or nucleic acid-protein interaction, in the presence and absence of a candidate inhibitor, may be accomplished in any vessel suitable for containing the reactants. Examples include microtitre plates, test tubes, and micro-centrifuge tubes.

In yet another embodiment, the protein-protein interaction component or potential interacting polypeptide may be used to generate an two-hybrid or interaction trap assay See U.S. Pat. No. 5,283,317; Zervos et al. (1993) *Cell* 72:223-232; Madura et al. (1993) *J Biol Chem* 268:12046-12054; Bartel et al. (1993) *Biotechniques* 14:920-924; and Iwabuchi et al. (1993) *Oncogene* 8:1693-1696), for subsequently detecting agents which disrupt binding of the interaction components to one another.

9. Pharmaceutical Compositions of Therapeutic Agents and Uses Thereof

Therapeutic agents or compounds identified by the methods described above are within the scope of the invention. Compositions comprising such therapeutics or compounds, in particular, compositions comprising a pharmaceutically efficient amount of the drug in a pharmaceutically acceptable carrier are also provided. Candidate therapeutics or compounds identified by the above methods may be formulated into pharmaceutical compositions, which are also within the scope of the present invention.

The compounds of the present invention may be administered by various means, depending on their intended use, as is well known in the art. For example, if compounds of the present invention are to be administered orally, they may be formulated as tablets, capsules, granules, powders or syrups. Alternatively, formulations of the present invention may be administered parenterally as injections (intravenous, intramuscular or subcutaneous), drop infusion preparations or suppositories. For application by the ophthalmic mucous membrane route, compounds of the present invention may be formulated as eyedrops or eye ointments. These formulations may be prepared by conventional means, and, if desired, the compounds may be mixed with any conventional additive, such as an excipient, a binder, a disintegrating agent, a lubricant, a corrigent, a solubilizing agent, a suspension aid, an emulsifying agent or a coating agent.

In formulations of the subject invention, wetting agents, emulsifiers and lubricants, such as sodium lauryl sulfate and magnesium stearate, as well as coloring agents, release agents, coating agents, sweetening, flavoring and perfuming agents, preservatives and antioxidants may be present in the formulated agents.

Subject compounds may be suitable for oral, nasal, topical (including buccal and sublingual), rectal, vaginal, aerosol and/or parenteral administration. The formulations may conveniently be presented in unit dosage form and may be prepared by any methods well known in the art of pharmacy. The amount of agent that may be combined with a carrier material to produce a single dose vary depending upon the subject being treated, and the particular mode of administration.

Methods of preparing these formulations include the step of bringing into association agents of the present invention with the carrier and, optionally, one or more accessory ingredients. In general, the formulations are prepared by uniformly and intimately bringing into association agents with liquid carriers, or finely divided solid carriers, or both, and then, if necessary, shaping the product.

Examples of suitable aqueous and non-aqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity may be maintained, for example, by the use of coating materials, such as lecithin, by the maintenance of the required particle size in the case of dispersions, and by the use of surfactants.

The present invention further provides methods of treating LQTS using pharmaceutical compositions comprised of therapeutic agents identified using the screening methods provided by the invention. The present invention contemplates the use of pharmaceutical compositions, e.g., to inhibit the progression of, treat, or prevent LQTS. Such methods may include administering to a subject a pharmaceutically effective amount of an agonist or antagonist of one or more genes or their encoded gene products involved in LQTS.

The dosage of any pharmaceutical composition of the present invention will vary depending on the symptoms, age and body weight of the patient, the nature and severity of the disorder to be treated or prevented, the route of administration, and the form of the supplement. Any of the subject formulations may be administered in a single dose or in divided doses. Dosages for the compounds of the present invention may be readily determined by techniques known to those of skill in the art or as taught herein. Also, the present invention provides mixtures of more than one subject compound, as well as other therapeutic agents.

The precise time of administration and amount of any particular compound that will yield the most effective treatment in a given patient will depend upon the activity, pharmacokinetics, and bioavailability of a particular compound, physiological condition of the patient (including age, sex, disease type and stage, general physical condition, responsiveness to a given dosage and type of medication), route of administration, and the like. The guidelines presented herein may be used to optimize the treatment, e.g., determining the optimum time and/or amount of administration, which will require no more than routine experimentation consisting of monitoring the subject and adjusting the dosage and/or timing.

While the subject is being treated, the health of the patient may be monitored by measuring one or more of the relevant indices at predetermined times during a 24-hour period. Treatment, including supplement, amounts, times of administration and formulation, may be optimized according to the results of such monitoring. The patient may be periodically reevaluated to determine the extent of improvement by measuring the same parameters, the first such reevaluation typically occurring at the end of four weeks from the onset of therapy, and subsequent reevaluations occurring every four to eight weeks during therapy and then every three months thereafter. Therapy may continue for several months or even years, with a minimum of one month being a typical length of therapy for humans. Adjustments to the amount(s) of agent administered and possibly to the time of administration may be made based on these reevaluations.

Treatment may be initiated with smaller dosages which are less than the optimum dose of the compound. Thereafter, the dosage may be increased by small increments until the optimum therapeutic effect is attained.

The combined use of several compounds of the present invention, or alternatively other chemotherapeutic agents, may reduce the required dosage for any individual component because the onset and duration of effect of the different components may be complimentary. In such combined therapy, the different active agents may be delivered together or separately, and simultaneously or at different times within the day.

Toxicity and therapeutic efficacy of subject compounds may be determined by standard pharmaceutical procedures in cell cultures or experimental animals, e.g., for determining the $LD_{50}$ and the $ED_{50}$. Compositions that exhibit large therapeutic indices are preferred. Although compounds that exhibit toxic side effects may be used, care should be taken to design a delivery system that targets the compounds to the desired site in order to reduce side effects.

The data obtained from the cell culture assays and animal studies may be used in formulating a range of dosage for use in humans. The dosage of any supplement, or alternatively of any components therein, lies preferably within a range of circulating concentrations that include the $ED_{50}$ with little or no toxicity. The dosage may vary within this range depending upon the dosage form employed and the route of administration utilized. For agents of the present invention, the therapeutically effective dose may be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information may be used to more accurately determine useful doses in humans. Levels in plasma may be measured, for example, by high performance liquid chromatography.

10. Kits

Any of the above-provided animals, cells, cell lines, vectors, microarrays, therapeutic agents etc. may be incorporated into kits. For example, provided are kits for preparing a non-human, non-murine transgenic mammal of invention, comprising a vector of the invention, such as a vector comprising a β-MyHC promoter and a mutant cardiac ion channel gene selected from the group consisting of: KvLQT1 (KCNQ1), HERG (KCNH2), SCN5A, KCNE1, MiRP1, Kir2.1, KCNJ2 and Ankyrin B. A kit may further comprise nucleic acid controls, buffers, and instructions for use.

Kits for evaluating the safety of drugs using the transgenic animals of the invention may comprise at least one transgenic animal of the invention.

Kits for evaluating a drug using genes identified herein may, for example, comprise an array having a plurality of addresses, wherein each address has disposed thereon at least one capture probe that hybridizes to at least one gene that is differentially expressed in a subject having LQTS. Yet other kits comprise compounds identified herein as candidate therapeutics for LQTS. The compositions may be pharmaceutical compositions comprising a pharmaceutically acceptable excipient.

Kit components may be packaged for either manual or partially or wholly automated practice of the foregoing methods. In other embodiments involving kits, this invention contemplates a kit including compositions or animals of the present invention, and optionally instructions for their use. Such kits may have a variety of uses, including, for example, imaging, diagnosis, therapy, and other applications.

EXEMPLIFICATION

The invention now being generally described, it will be more readily understood by reference to the following examples which are included merely for purposes of illustration of certain aspects and embodiments of the present invention, and are not intended to limit the invention in any way.

Example 1

Transgenic Rabbit Models of LQT1 and LQT2

We selected the human KvLQT1-Y315S (for LQT1) and HERG-G628S (for LQT2) mutations. Since KvLQT1 and ERG play only a minor role in mouse physiology, we decided to create genetic models in a relatively large mammal in which the currents encoded by KvLQT1 and ERG genes play a major role in cardiac repolarization. Both mutations are located in the 'pore' region, which is a highly conserved signature sequence of the voltage-gated $K^+$ channels across species. These mutations have been described in families afflicted with LQT1 and LQT2, respectively, within different ethnic group. However, the cellular phenotype of the cardiomyocytes and the electrical remodeling associated with long-term expression of these mutations in the heart were never described because of difficulties in obtaining human ventricular myocytes. Each of the mutations has been shown to generate completely non-functional channels, which exerted a strong dominant negative suppression of the wild-type (WT) $I_{Ks}$ and $I_{Kr}$-like currents, respectively, in heterologous systems. We reasoned that these mutations should exert strong dominant negative suppression of the endogenously expressed $I_{Ks}$ and $I_{Kr}$ currents to create human-like LQT phenotypes in rabbit heart. Such expectations are well-supported by the experimental designs of the prior mouse models of LQTS. The coding sequences of KvLQT1 and ERG genes deposited in the GenBank databases show a high degree of identity across mammalian species. For example, alignments of HERG (KCNH2) and rabbit ERG show nearly 90% identity at the nucleotide level. Similarly, the KvLQT1 (KCNQ1) coding sequence from humans and mice is also 90% identical but has not yet been cloned from rabbit.

The human HERG pore mutation (HERG-G628S-3.58 Kb), and KvLQT1 pore mutant (KvLQT1-Y315S-2.1 Kb) were used for this project. A FLAG epitope was introduced at the N-terminus of the channel polypeptides, and the cDNAs were both cloned under the control of the rabbit cardiac β-MyHC (6.9 kb) into a unique EcoRI site located in the noncoding exon 3 of the β-MyHC gene. The vectors contain the hGH polyA signal located 3' to the channel cDNA (pBlue Script II plasmid).

We decided to use the rabbit β-MyHC promoter, since unlike the α-MyHC protein, which is downregulated in the adult rabbit ventricles, β-MyHC is the predominant protein in the ventricles of both adult humans and rabbit, comprising greater than 95% and 85% of the total myosin pool, respectively. The rabbit β-MyHC promoter confers a high level of expression of transgenes in the rabbit heart, where the β-MyHC is naturally expressed (J. Robbins, personal communication). The constructs were sequenced on both strands to verify the presence of the pore mutation as well as the correct sequence of the channels. The entire transgene, including the β-MyHC+KvLQT1-Y31S or HERG-G628S+3'UT of the human growth hormone (hGH), were released from the vector by a NotI digestion, separated from the vector by gel electrophoresis, purified and diluted in water, and injected into oocytes. Both constructs were tested in COS-7 cells for expression of the FLAG-tagged polypeptides (under the control of the CMV promoter). The results showed that they each expressed the appropriately sized polypeptides (data not shown).

Donor New Zealand White rabbits were created by inducing superovulation with human chorionic gonadotropin hormone (hCG). Female rabbits to be used as embryo donors were injected intravenously with 120 U PMSG and 150 U hCG on day 1 and day 4, respectively. The rabbits were mated with a fertile male on day 4 immediately prior to the hCG injection. Embryos at the single-cell stage were harvested on day 5. The recipient rabbits were mated with a sterile (vasectomized) male at the same time point the donor rabbits were mated. Injected embryos were transplanted to the oviducts of anesthetized recipient rabbits via laparotomy. The embryos were transplanted to oviducts exposed by a small incision through the middle line of the abdominal wall. The procedure was performed on a surgical table located in a separated area within the laboratory set aside specifically for the surgery. The whole procedure was performed with animals under appropriate anesthesia and by the standard aseptic procedures addressed in the Medical Center's Program of Veterinary Care, including the preparation of surgical site and use of sterile supplies. Successful generation of transgenic rabbit lines requires a great deal of effort and much expertise because of the low pregnancy rate and high rate of neonatal mortality.

Newborn rabbits were screened by PCR for the presence of the transgene. Rabbit DNA was obtained from ear biopsies using a standard protocol. The forward primer used for all PCR reactions is derived from the β-MyHC sequence adjacent to the EcoRI cloning site (5'-GAA CCA GCT TCT TCC GCT CAC TAC AGG TAC AG-3') (SEQ ID NO: 3). Two reverse oligonucleotides were used for each transgene. The oligonucleotides for HERG were: 5'-GGG CAC CAC ATG CAC CAG ACA TAG GAA GCA G-3' (SEQ ID NO: 4) (HERG-A) and 5'-CCC ACC ATG TCC ATC ACC ACC TC-3' (SEQ ID NO: 5) (HERG-B) with products of 420 and 479 bp, respectively. The oligonucleotides for KvLQT1 were: 5'-AGC CGG TGG GAC GCT CGA GGA AGT TGT AGA G-3' (SEQ ID NO: 6) (KvLQT1-A) and 5'-AAG ATG AGG CAG ACC AGG ACG ATG AGG AAG AG-3' (SEQ ID NO: 7) (KvLQT1-B) with products of 405 and 478 bp, respectively. Based on the PCR results, we identified two male founders for ERG-DN [#033 (FIG. 5—top panel) and #3 (dead, not shown)], and a single male founder for KvLQT1-DN line [#002 (FIG. 5, bottom panel)]. One of the ERG-DN founders died 3 weeks after birth, with 4 other littermates likely killed by their foster mother. The overall efficiency of success was in the range of 4.3 to 7.1% (1 of 23 born rabbits for KvLQT1 and 2 of 28 born rabbits for ERG-DN). In addition to the primers detailed above, we designed primers derived from the 3' end of the transgene cDNA. These primers confirmed our previous observations with the founders' DNA. The quality of the genomic DNA was checked using PCR with primers that amplified the rabbit ERG endogenous gene.

Figure 6:
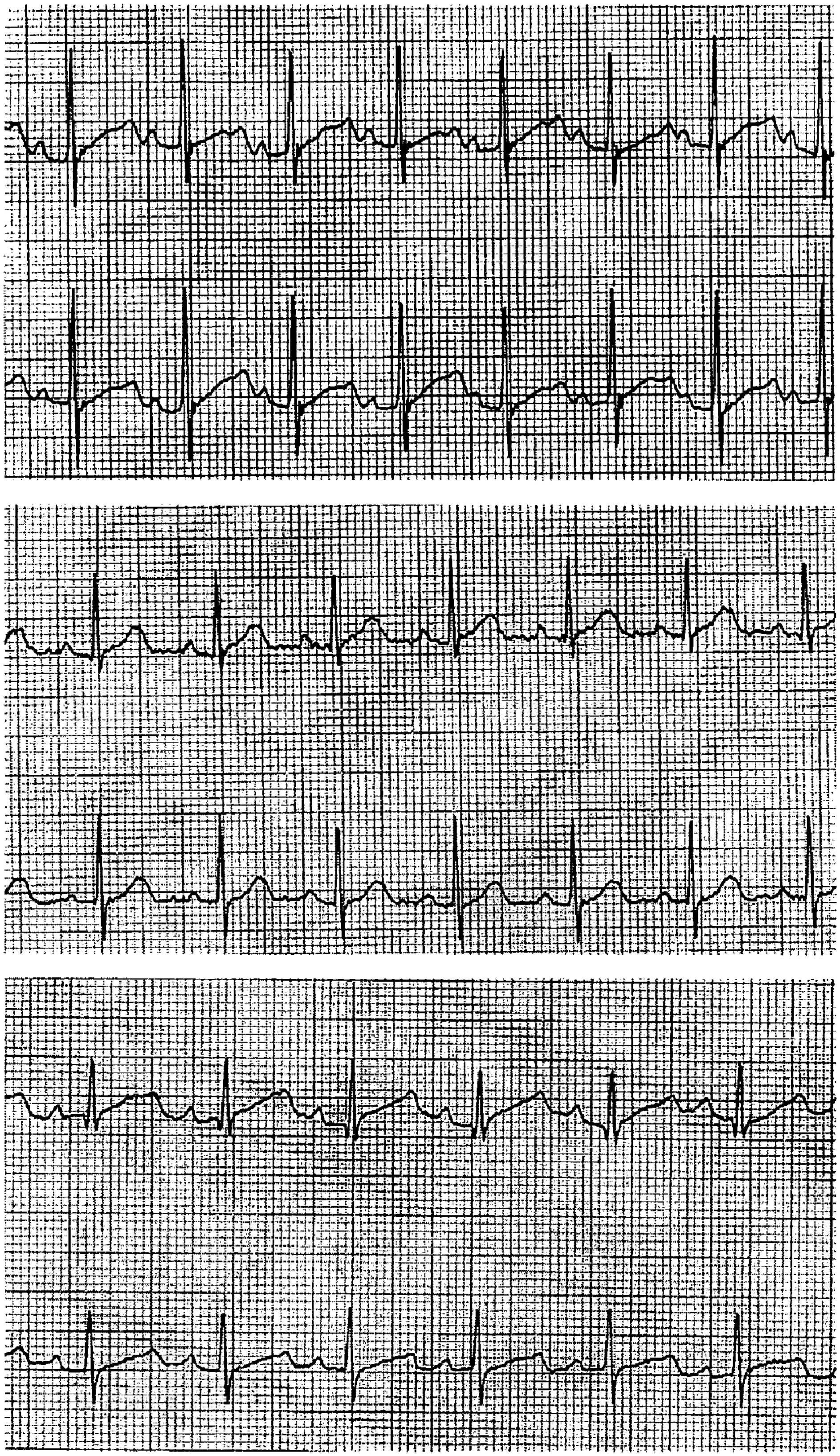
FIG. 6 depicts surface ECGs of the founders and a control rabbit. Each panel depicts simultaneously recorded leads II (top) and V5 (bottom). The top panel was recorded from ERG-DN rabbit (#033); the middle panel, from control rabbit (#031); and the bottom panel, from KvLQT1-DN rabbit (#002). Note the marked difference in length of the QT interval and the shape of the T-waves.
Figure 7:
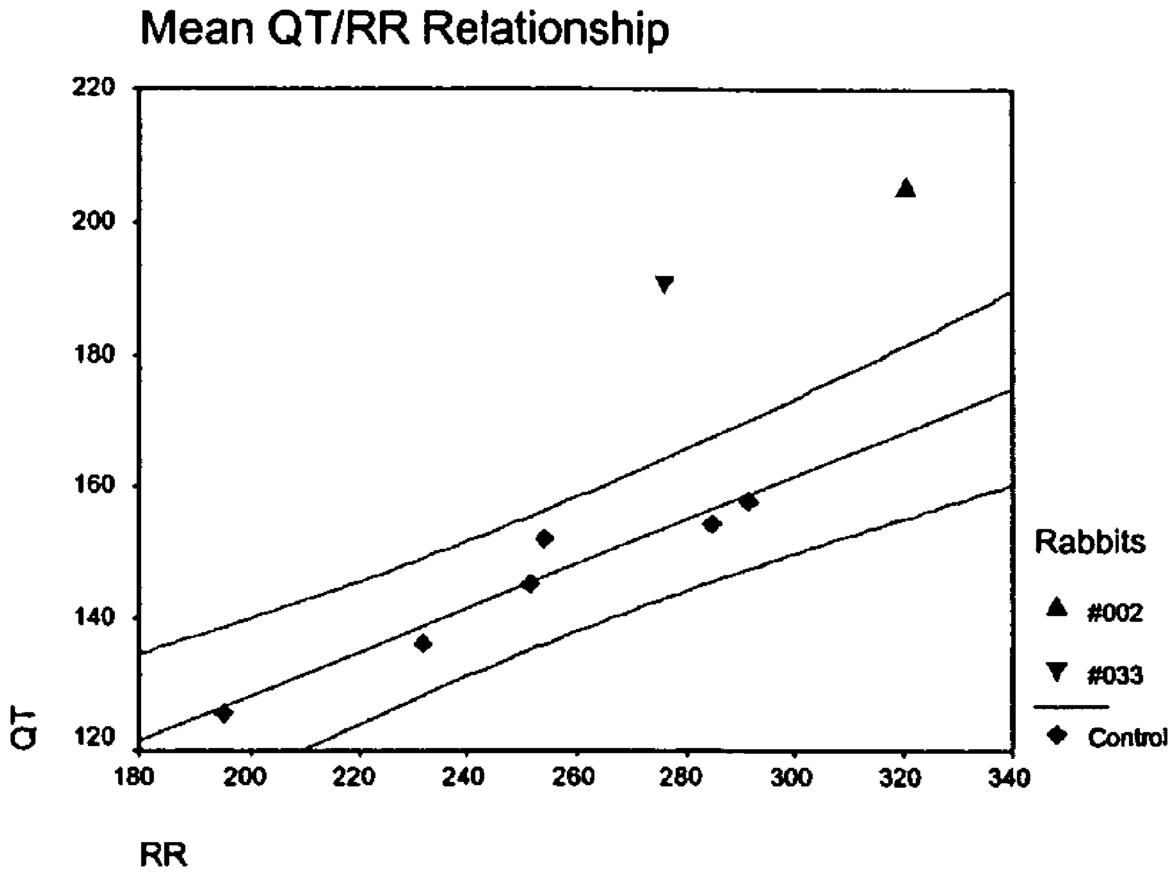
FIG. 7 depicts mean QT/RR relationships drawn with 95% confidence intervals. Solid triangles depict KvLQT1-DN (#002) and ERG-DN (#033).

We next screened the two founders and six age- and sex-matched littermate controls by surface ECG. The ECGs were recorded using a Marquette System with a paper speed of 50 mm/sec and 20 mm/1 mV with animals under anesthesia with midazolam 2.0 mg/kg BW administered intramuscularly. Rabbit #033 was 16 weeks old and weighed 3.5 kg. Three of his littermates were included in the controls, and their weight ranged from 3.4 to 3.6 kg. Rabbit #002 was 22 weeks old and weighed 3.6 kg. Three of his littermates were included in the study, and their weight ranged from 3.6 to 4.2 kg. All rabbits were males. FIG. 6 depicts simultaneously recorded leads II and V5. The top panel was recorded from ERG-DN rabbit (#033), the middle panel from control rabbit (#031), and the bottom panel from KvLQT1-DN rabbit (#002). Note the unique morphology of the T-waves. ERG-DN rabbit has a bifurcated T-wave, while KvLQT1-DN rabbit has a shallow T-wave with a late peak. Analyses of the data show that the mean QT from all 12 leads of the ERG-DN (#033) rabbit was (mean±SEM) 190.8±3.6 ms, with a longest QT of 210 ms at an RR interval of 290 ms. The mean QT of KvLQT1-DN (rabbit #002) rabbit was 205.4±3.6 ms, with a maximal QT of 225 ms at an RR interval of 325 ms. The mean QT interval of the 6 control rabbits was 144±2.4 ms. FIG. 7 illustrates that the mean QT interval of all 12 leads of rabbit #033 and rabbit #002 lies outside the 95% confidence interval of the mean QT intervals of the control rabbits. A two-tail t-test showed that the raw QT intervals of ERG-DN and KvLQT1-DN were significantly longer than that of control rabbits ($p<0.001$).

Thus, the mean QT intervals of the founder rabbits are substantially longer than those of controls.

Taken together, these data demonstrate that additional transgenic founders may be generated and that the long QT phenotype observed in rabbits #002 and #033 indicates that our dominant negative approach can be used in the rabbit to generate models with long QT phenotype.

Figure 8:
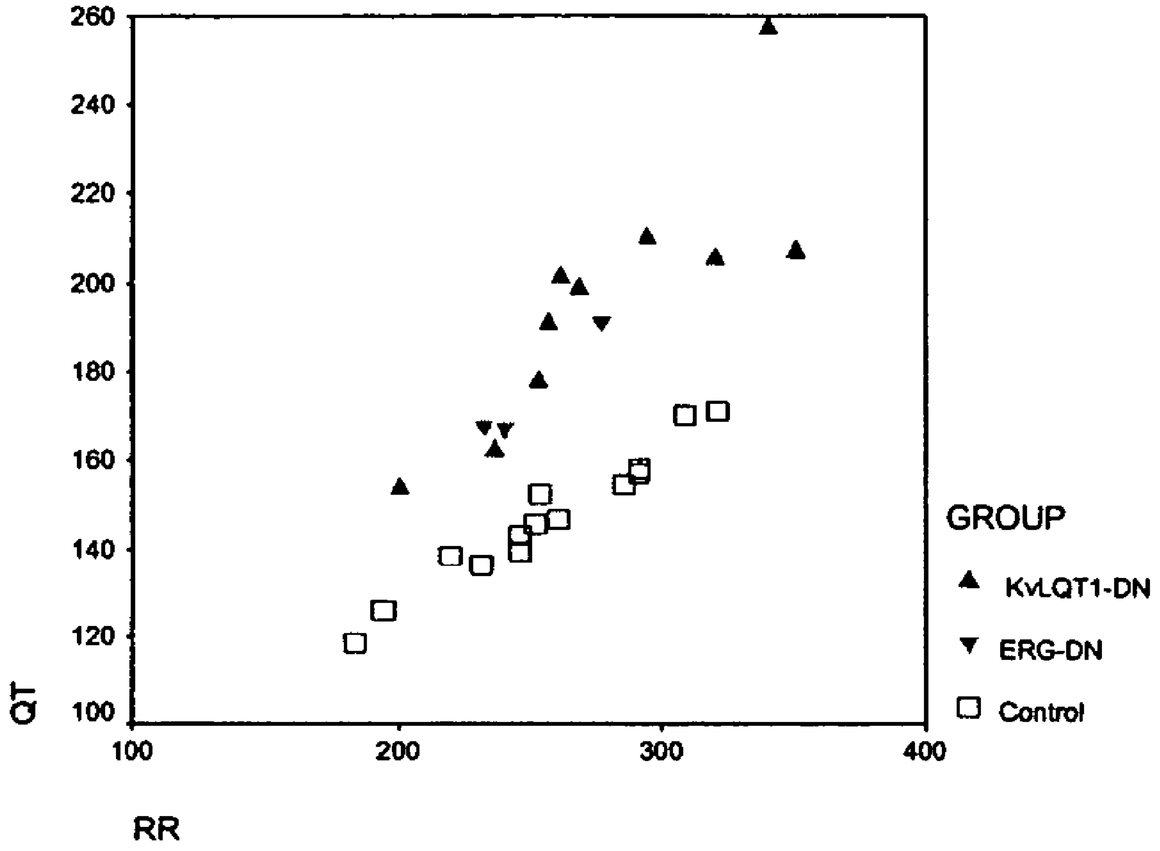
FIG. 8 depicts mean QT/RR relationships (ms). Solid triangles depict the ERG-DN (n=3 males including the founder) and KvLT1-DN (n=10 including the founder, of which 5 are males) transgenic rabbits. The squares denote control wild-type littermates (n=14 of which 12 are males).

We next analyzed offspring of these founders. The first KvLQT1 litter consisted of 12 rabbits; PCR of genomic DNA using multiple primers revealed that 9 (5 females and 4 males) were positive for the KvLQT1 transgene and 3 (males) were littermate controls. The first litter of ERG-DN consisted of 6 rabbits; PCR of genomic DNA revealed that 1 (male) was positive for the ERG-DN transgene and 5 (3 males and 2 females) were littermate controls. The second litter consisted of 6 rabbits (4 males and 2 females); PCR of genomic DNA revealed that 1 male was positive for the ERG transgene. We next screened the F1 rabbits by surface ECG (FIG. 6). All rabbits that were analyzed were 3 to 3.5 months old, and their weights ranged from 2.7 to 3.5 kg. The ECGs were recorded using a Marquette System with a paper speed of 50 mm/sec and 20 mm/1 mV with animals under anesthesia with midazolam 2.0 mg/kg body weight administered intramuscularly. The QT/RR relationships of the founders and their littermate controls as well as all the F1 rabbits are shown in FIG. 8. The results show a clear separation between the QTs of the founders and the F1 transgenic rabbits (triangles) and the QTs of their littermate controls (squares).

The mean QT interval (±SD) of the control rabbits was 146.8±15.1 ms (n=14). The mean QT intervals of the KvLQT1-DN rabbits (196.5±28.9 ms; n=10) and the ERG-DN rabbits (175.2±13.6 ms; n=3) were significantly longer than the QT of controls ($P<0.001$ and $P<0.05$, respectively). Clearly, the founder rabbits transmitted the long QT phenotype to the F1 rabbits that inherited the transgene. We generated 16 additional KvLQT1-DN F1 rabbits, of which 6 are positive for the transgene (3 females and 3 males). The overall transmission rate of KvLQT1-DN transgene to F1 is 53.5% (15 positive of 28 F1 rabbits). We also generated 35 additional newborn ERG-DN F1, of which 9 are positive for the transgene. Of these ERG-DN rabbits, 4 are females and 5 are males. The overall transmission rate of the ERG-DN transgene to F1 rabbits is 23.4% (11 of 47). We also mated an F1 ERG-DN male rabbit with a WT female rabbit and generated 8 F2 rabbits, of which 4 are positive for the transgene (50%). We therefore believe that the lower rate of transmission from the ERG-DN founder to the F1 rabbits likely reflected heterogeneous expression of the transgene in the sperm. By contrast, the F1 ERG-DN rabbit transmitted the transgene to 50% of the F2 rabbits (as expected).

Of note, the founder ERG-DN rabbit (#033) was found dead in the cage at the age of 7.5 months. In addition, during the recording of the surface ECG of rabbit #318 (ERG-DN F1 rabbit), we documented a paroxysm of VPBs every eighth beat for a total of 9 VPBs; this was triggered by a startled response after the rabbit's ear was touched to verify the tag number. The arrhythmia resolved spontaneously. Two months after this arrhythmia was recorded, the rabbit was found dead in the cage at the age of 5.5 months. The rabbits looked and acted normal when examined the day before the event, and both died while mating. A complete necropsy of rabbit #033, including histology, done by a veterinary pathologist revealed diffuse, moderate congestion of trachea, lung, liver, and kidneys, consistent with acute cardiac failure. We recently repeated the surface ECG of ERG-DN F1 rabbit #80 at the age of 6 months. The results showed sinus rhythm with prolonged QT interval and ventricular bigeminy with the premature beats arising before the end of the T-wave (R on T) (FIG. 9-B*ottom*). The arrhythmia lasted for at least 4 minutes. Repeat ECG done a week later revealed sinus rhythm with prolonged QT interval without premature beats (FIG. 9-T*op*). We reason that the first ECG was associated with much more stress due to the shaving and extra handling for hair removal. Collectively, these observations indicate that the ERG-DN phenotype is associated with premature "sudden" death (2 of 15) and significant ventricular arrhythmias. We therefore reason that the ERG-DN rabbits that died prematurely at ages between 5.5 and 7.5 months developed ventricular arrhythmias. By contrast, we did not observe any unexplained death or arrhythmias in any of the KvLQT1-DN rabbits. Since the extent of the QT prolongation is similar in both groups, it is likely that prolongation of the QT interval itself is not sufficient to cause sudden death.

Example 2

Analysis of the Surface ECG, Spontaneous and Inducible Arrhythmias

The ECG and arrhythmic phenotype of the two established transgenic lines may be characterized to confirm that the expression of a pore mutant of the human KvLQT1 or HERG as a transgene in rabbit heart has created a genetic model for LQT1 or LQT2 and that the phenotype is associated with spontaneous ventricular arrhythmias and sudden death.

The surface ECG of 10 transgenic KvLQT1-DN male and 10 transgenic KvLQT1-DN female rabbits, as well as an identical number of male and female ERG-DN rabbits, may be characterized. QT and QTc from surface ECGs may be assessed as compared with 10 age- and sex-matched littermate controls. The serial ECGs may be done at 8 weeks and at 3, 6, 9, and 12 months to assess the effect of the transgenes during development. The QT dispersion (QTd) as defined by the differences between the longest and shortest QT interval in the 12-lead ECG may be assessed and tested whether it is predictive of arrhythmias in our model. Whether there are changes in QTd between male and female transgenic rabbits and whether there is a correlation between QTd and spontaneous and inducible arrhythmias may be determined, as well as whether or not QTd is predictable in the model system. Collectively, such experiments may define the phenotype during different developmental stages and explore whether sex modulates the phenotype.

Whether male or female ERG-DN and KvLQT1-DN rabbits will exhibit spontaneous arrhythmias under control conditions may be determined as follows. 10 ERG-DN male and 10 ERG-DN female rabbits, a similar number of KvLQT1-DN rabbits (16 to 24 weeks old), and a similar number of age- and sex-matched littermate controls will be monitored for 48 hours using electrodes with transmitters developed by Data Sciences (D70-EEE). The D70-EEE transmitters may be modified to reduce the number of electrodes implanted from six to four. The transmitters may be implanted after anesthetizing the animals by initial subcutaneous injection of Butorphanol (0.5 to 1 mg/kg) and Acepromazine (0.5 to 1 mg/kg), followed by intramuscular injection of ketamine (30 to 40 mg/kg) and xylazine (5 to 10 mg/kg). The implantable device may be placed subcutaneously on the back of the animals through a small incision. During implantation, one electrode may be tunneled subcutaneously to an incision above the right shoulder; another one may be placed in a similar fashion above the left shoulder. The wires may then be secured with a suture to the muscle. Likewise, the tip of the third electrode may be tunneled and placed subcutaneously below the apex of the heart, and the fourth electrode may be placed in an identical subcutaneous location on the right side of the animal. This may enable an ECG similar to standard ECG limb leads I-III to be recorded. The rabbits will be allowed to recover for 72 hours before data is recorded. The analog telemetric signals may be digitized at 1 kHz using an A/D converter in a PC, and the data may be acquired by Windows-based Dataquest A.R.T. data acquisition software (Data Sciences International). The data may be analyzed and QT, QTpeak, JT, QRS, and RR intervals may be measured using Physiostat ECG analysis software (Data Sciences International). Average values of the P, PQ, QT, QT-peak, T-peak to T-end, QRS, and RR intervals for wild-type and transgenic rabbits may be established by statistical analysis, and corrected QTc intervals will be established using regression models similar to those used previously in mice.

The role of stimulation such as fright (alarm clock), exercise, and hot/cold environments for induction of TdP in LQT1 and LQT2 rabbits may be determined. Reproducible induction of spontaneous arrhythmia may allow analysis of the cellular processes that trigger and maintain the arrhythmias as described below. Our data indicate that the mating of adult ERG-DN males with WT females is associated with premature death. We reason that these rabbits developed TdP that deteriorated to ventricular fibrillation, thereby inducing acute cardiac failure, though we cannot rule out bradyarrhythmia as the cause of death. Therefore all ERG-DN male rabbits that will be bred with WT females may be monitored to determine the cause of death, if it occurs. If the cause of death is TdP, an ICD may be implanted to try and prevent the rabbit's premature death, for example, by using a Medtronic GEM III AT ICD (with atrial detection). As heart rates of rabbits are markedly higher than the highest programmable ventricular rate for a VT/VF zone of all currently available ICDs, ICDs with the additional option of detecting atrial arrhythmias may be used. In the atria, detection of atrial fibrillation can be programmed to rates of 400 bpm and above, whereas the maximal rate for the detection of ventricular arrhythmias is 250 bpm. Thus, the use of an "atrial" electrode for the detection and therapy of ventricular arrhythmias may enable the use of off-the-shelf devices both for monitoring and protection of these animals.

For a more complete description of the phenotype of LQT1 and LQT2 rabbits, programmed electrical stimulation (PES) of the right atrium and the right ventricle may be carried out in 10 KvLQT1-DN male and 10 KvLQT1-DN female rabbits, an identical number of ERG-DN rabbits, as well as age- and sex-matched littermate controls. These studies may be carried out in an animal EP laboratory equipped with a two-channel computer-based programmable cardiac stimulator (EP Med Systems, Inc), and an EP digital recording system (Pruka Engineering, Inc) capable of simultaneous recordings of 32 channels of either surface electrocardiogram or intracardiac recordings at a sampling rate of 1 KHz. A transvenous 2F octopolar EP-catheter (Cypher, NuMed, New York) may be placed first in the right atrium and then in the right ventricle. Bipolar electrogram recordings may be obtained from the right atrium and right ventricle. During the procedure a continuous ECG of the limb leads, and the chest leads V1, V3, and V5, may be recorded. Stimulation may be performed at twice the diastolic threshold. All ECG intervals (P, PR, QRS, QT, JT, QTc, JTc, and RR) and axes (P, QRS, T) may be measured for each rabbit by a blinded observer. To correct the QT and the JT intervals, a new correction formula specific for rabbits may be established using an approach similar to the one used to establish a formula for mice (Mitchell, G. F., A. Jeron, and G. Koren, *Measurement of heart rate and Q-T interval in the conscious mouse*. Am J Physiol, 1998. 274(3): p. H747-51). The sinus node recovery time may be obtained at three different cycle lengths, including the corrected SNRT (SNRT minus basic sinus cycle length, SCL) and SNRT/SCL percentage. The atrial refractory period, AV node refractory period, minimum cycle length maintaining a 1:1 AV conduction, AV Wenkebach cycle length, and maximum paced cycle length with a 2:1 AV block may be measured to determine the atrial and AV conduction properties for each animal. The atrial and ventricular refractory periods may be measured at two pacing rates using a single extrastimulus. Depending on the type of anesthesia and the basal heart rate of the animals during anesthesia, the BCLs may be adapted. Initially, a BCL1: 220 ms and BCL2: 180 ms may be used. The programmed stimulation protocol may consist of a train of 10 beats (S1) at BCL1 or BCL2 with a single extrastimulus added to the train. The S2 interval may be progressively shortened by 5 ms until the VERP is reached; S2 is thereafter coupled with the last effective interval. Similarly, S3 and S4 stimuli may be added sequentially. If no ventricular arrhythmias are induced, isoproterenol (0.05 μg/kg) may be given i.v. to increase the heart rate by at least 20%, and the ventricular stimulation may be repeated. In case of the induction of a persistent ventricular tachycardia during the stimulation, overdrive stimulation and/or electrical cardioversion (2-5 Joule/kg) may be attempted.

In both KvLQT1 and ERG-DN rabbits, it is likely that a relatively long QT interval from the surface ECG with electrocardiographic characteristics of long QT syndromes will be recorded, i.e., broad-based T-waves in the case of KvLQT1-DN and low-voltage and/or bifurcated T-waves in the case of ERG-DN. Indeed, the preliminary surface ECGs show some of these characteristics. Sex-related differences in the QT interval may be observed, with female KvLQT1-DN rabbits likely having longer QTs and QTcs due to sex-related differences in the expression of $I_{Kr}$, which is lower in female rabbits.

Recording of only a single ECG lead makes it difficult to differentiate between arrhythmias and artifacts resulting from movement or scratching. Thus, transmitters with the capability of recording two or more ECG leads simultaneously may be used. It is likely that spontaneous arrhythmias in ERG-DN rabbits will be detected; however, arousal reactions and stress may be necessary to trigger arrhythmias in KvLQT1-DN rabbits. It is anticipated that in ERG-DN rabbits, no sex differences in the prevalence of spontaneous arrhythmias will be observed, since there are no known sex differences in the expression of KvLQT1-encoded currents. By contrast, in KvLQT1-DN rabbits, sex-related differences in the incidence of spontaneous arrhythmias may be observed, since the female rabbits express lower $I_{Kr}$ currents and might thus be more prone to spontaneous arrhythmias. Reproducible induction of spontaneous arrhythmias will set the stage for biochemical studies of cardiomyocytes and cardiac muscle tissue derived from rabbits that are prone to or have just developed arrhythmias.

The control rabbits should not be inducible. By contrast, ERG-DN rabbits may be inducible by PES without β adrenergic stimulation, and isoproterenol will likely increase the incidence of induced arrhythmias in these rabbits. A significantly lower inducibility of KvLQT1-DN rabbits is anticipated, since no TDR in the absence of β adrenergic stimulation is expected (for extensive discussion, see Example 6). By contrast, isoproterenol should significantly increase the incidence of inducible arrhythmias in KvLQT1-DN rabbits. Indeed, in acute pharmacologic models in dogs, chromanol 293B never produced TdP in experimental models either spontaneously or in response to program stimulation. The mechanisms that underlie the inducibility of arrhythmia and the effect of β adrenergic stimulation may be further explored at the cellular and organ (i.e., wedge preparation) levels as discussed below. A gender difference in inducibility in KvLQT1-DN rabbits is anticipated, wherein female rabbits will be more prone to induction of arrhythmias under isoproterenol than will male rabbits due to lower expression of IKr currents. To complement the PES experiments, the α1-adrenoreceptor agonist methoxamine (70 nmol/kg/min) may be used to determine whether it induces arrhythmias in LQT1, LQT2, or control littermates. The model was described by Carlsson et al., who induced TdP by infusion of methoxamine and clofilium to WT rabbits (100 nmol/kg). This protocol may be modified so that methoxamine alone is infused. If methoxamine induces arrhythmias, then pretreatment with prazosin (1 mg/kg) should abolish its proarrhythmic effect. These studies will explore whether the α1-adrenoreceptor agonist can induce arrhythmias in either LQT1 or LQT2. If this is the case, the mechanism of induction of arrhythmias may be explored by adding methoxamine to LV wedge preparation derived from either LQT1 or LQT2 hearts (see Example 6). This is important since methoxamine has a profound effect on blood pressure and aortic impedance, and therefore the arrhythmias may not necessarily reflect a direct α1-adrenoreceptor agonist effect on the myocardium.

To rule out cardiac hypertrophy, serial echocardiography studies on sedated rabbits may be carried out to assess the effect of the transgene expression on heart size, left ventricular size, and left ventricular function. Using a Toshiba 140 echocardiography machine and a 7.5 MHz probe, 10 transgenic male and 10 female rabbits may be serially examined, as well as littermate control rabbits, at 8 weeks and at 6, 9, and 12 months. Analysis may include: dimensions of LV, RV, LA, wall thickness, valve function, and LV function. This may offer insight into what effect the action potential prolongation has on the heart in vivo and whether this influences the development of cardiac hypertrophy. These studies may be validated by anatomical and histological studies including chamber size, weight, and histological analyses of LV walls of LQT and control littermate rabbits. It is not expected that the echocardiogram will reveal changes in left ventricular function or hypertrophy in these models, since similar experiments with pore mutants of several channels in mice did not induce such changes.

Example 3

Analyses of the Expression and Subcellular Distribution of Potassium Channels Expressed in Cardiomyocytes Derived from KvLQT1-DN and ERG-DN Rabbits In order to better understand the pathogenesis of arrhythmias and sudden death in these models, the steady-state levels of potassium channel polypeptides in different layers (and regions) of the myocardium of the left ventricle may be studied. These experiments will test the hypothesis that K+ channel dysfunction in LQT1 and LQT2 results in compensatory changes in function and expression of other ion channels and that the manifestations of LQT1 and LQT2 depend on modulation by autonomic factors and function of other ion channels. Having a realistic model of LQT1 and LQT2 will enable us to elucidate the long-term remodelling effects of overexpression of dominant negative pore mutants of HERG and KvLQT1 in cardiomyocytes derived from different regions of the left ventricle. These findings can then be correlated with electrophysiological studies of cardiomyocytes derived from these layers functional studies at the cellular, tissue (wedge preparation), and organ levels, as described below.

Figure 10:
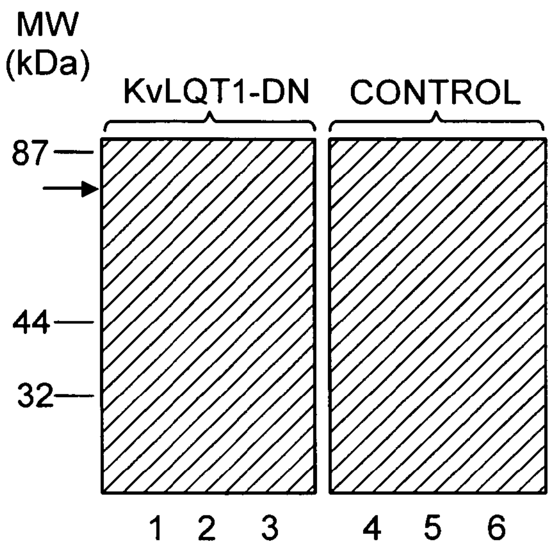
FIG. 10 depicts immunoblot assays of precipitates of crude heart lysates derived from the free wall of a KvLQT1-DN rabbit (lanes 1-3) and a control littermate (lanes 4-6). The lysates were first reacted with anti-FLAG antibodies (lanes 1 and 4), anti-KvLQT1 antibodies (Santa Cruz) (lanes 2 and 5), or control IgG (lanes 3 and 6), and the precipitated proteins were analyzed by immunoblotting with anti-FLAG antibodies. The arrow denotes FL-KvLQT1-Y315S polypeptides. Faster migrating background bands represent immunoglobulins.

The expression of the transgene polypeptides in the rabbit ventricular myocardium may be studied first. For such studies, rabbits that are 16 to 24 weeks old may be used. In preliminary studies, crude heart lysates derived from the free wall of the left ventricle of a KvLQT1-DN rabbit and a control littermate have been analyzed. Immunoprecipitation with anti-FLAG and anti-KvLQT1 antibodies precipitated FL-KvLQT1-Y315S polypeptides with an apparent molecular weight of about 75 kDa from KvLQT1-DN heart lysates (FIG. 10, lanes 1 and 2) but not from a control littermate heart (FIG. 10, lanes 4 and 5). Control precipitation with IgG did not precipitate the transgene polypeptides (FIG. 10, lane 3). Because of the relatively small colony of young adult ERG-DN rabbits and the episodes of sudden death, none of these rabbits have yet been sacrificed. However, on the basis of these results and our transfection studies, the HERG-G628S polypeptides are expected to be detected in the heart as well.

The steady-state levels of several cardiac potassium channel polypeptides expressed in crude membrane preparations of epicardial, mid-myocardial, and endocardial layers of the left ventricular free wall may also be studied as follows. The transcripts of these channels may be analyzed using total RNA derived from the same layers. These studies may use cardiac muscle derived from the apical, mid, and basal regions of the free wall of the left ventricle, as well as the free wall of the right ventricle. Thin (1.0-1.5 mm) sections of the epicardial and endocardial sides may be cut. Some of these regions will correspond to the segments of the myocardium that are used for wedge preparation (see Example 6). Northern blots, quantitative RT-PCR, and immunoblots with antibodies to FLAG (for the transgenes), Kv1.4, Kv4.2, Kv4.3, ERG, and KvLQT1 polypeptides may be used to compare the expression of these channel polypeptides in the three layers with extracts derived from age- and sex-matched myocardial sections of control rabbits. The antibodies are available from commercial resources as well as from our collaborators. The same antibodies may be used for immunocytochemistry of cardiomyocytes isolated from these layers of the left ventricle. These experiments are designed to study the transmural distribution of these polypeptides at different regions of the heart as well as their intracellular distribution.

The expression of Kv1.4, Kv4.2, and Kv4.3 in control rabbits may prove to be higher in the epicardial layer. Though $I_{to}$ in the rabbit behaves like Kv1.4, preliminary studies indicate that the epicardial layer is rich in the transcripts and polypeptides of Kv1.4, Kv4.2, and Kv4.3 (Stanley Nattel, personal communication). Similar distribution of these polypeptides in ERG-DN and KvLQT1-DN rabbits is anticipated. To identify the rabbit native KvLQT1 (RKvLQT1) and ERG (RERG) polypeptides, specific polyclonal anti-peptide antibodies to RKvLQT1 and RERG may be generated using unique sequences at the C- or N-termini where the rabbit sequence differs from those of HERG and KvLQT1. These antibodies will be raised in goats. The commercially available antibodies may cross-react with the human transgene as well as with the native channels. The methodology for developing anti-peptide antibodies and the appropriate controls are described in our previous publications. Extracts derived both from male and female rabbit hearts may be studied, since there are sex-related differences in the expression of rabbit $I_{Kr}$ currents. A decrease in KvLQT1 polypeptides in the mid-myocardial layer may be observed, while ERG polypeptides are likely to be evenly distributed. The LQT1 and LQT2 models may address whether the pattern of potassium channel expression in ERG-DN and KvLQT1-DN models will be modified by electrical remodelling due to prolongation of the APD and QT interval related to the respective absence of $I_{Kr}$ and $I_{Ks}$ in these models.

The dominant negative transgene polypeptides may be evenly distributed across the myocardium, and may form heteromultimeric complexes with the homologous native channel polypeptides, which complexes may reach the plasma membrane. Alternatively, complexes between FL-KvLQT1-Y315S or FL-HERG-G628S polypeptides and the WT channels could be retained in the ER and degraded. In this case, the steady-state levels of native KvLQT1 and the native ERG (RERG) will be downregulated. Our preliminary data suggest that FL-KvLQT1-Y315 S polypeptides are detectable, and therefore we favor the hypothesis that WT KvLQT1 and the transgene form stable heteromultimeric complexes. Thus, the immunoprecipitation of FL-KvLQT1-Y315S with high-affinity murine anti-FLAG antibodies (FIG. 10) may coprecipitate additional polypeptides that participate in the formation of a multimeric complex that contains WT KvLQT1. Thus, in future studies, the precipitated peptides may be analyzed using proteomics in order to identify additional polypeptides that associate and regulate KvLQT1. To that end, we recently demonstrated that Kv1.5 coprecipitates with caveolin-3 and SAP97 in the heart and that the complex regulates Kv1.5 expression (Folco E J, Roder K, Mitchell G F, Koren G. *Cardiac memory" a struggle against forgetting* (*Editorial*). Circulation Research 2003; 93: 384-386.).

These models may also help address the potential role of signal transduction pathways such as calmodulin (CaM)-dependent cellular signaling in triggering cardiac arrhythmias. A significant number of studies highlight the potential role of Ca2+/CaM-dependent protein kinase II (CaMK) in the induction of TdP through the augmentation of L-type calcium channel currents. However, most of these studies were carried out in acute pharmacologic models in rabbits or in mice, and thus their applicability to humans is questionable. Having a realistic model of LQTS could help future studies address the potential role of CaMK by measuring directly CaMK activity in LQT1 and LQT2 heart lysates or indirectly by assaying for the steady-state levels of phosphorylated CaMK as compared with levels in littermate controls.

Example 4

Analysis of Currents Expressed in Cardiomyocytes Derived from LQT1 and LQT2 Hearts The action potentials and the expression of outward and inward potassium as well as the inward calcium currents expressed in myocytes derived from the same transmural layers described in Example 3 may be studied to correlate the phenotype of the cells from the different layers of the heart with the molecular biochemical studies described above and the functional studies (wedge preparation) described below. For example, the studies may be used to ascertain whether the transgenes alter the action potential pattern and duration and whether they regulate the density of the different components of the voltage-gated outward potassium currents expressed in adult rabbit cardiac myocytes derived from different transmural layers of the myocardium of the left ventricle. These studies may be done under control conditions and in the presence of isoproterenol (10-100 nmol/L) in order to investigate the effect of β-adrenergic agonists on the action potential duration, inward calcium currents, and outward potassium currents of cardiomyocytes derived from different layers of the rabbit left ventricle.

β-adrenergic stimulation is known to increase L-type calcium channel currents, IKs currents, and chloride channel currents. The increase in outward current tends to shorten APD, whereas the increase in $I_{Ca}$ tends to prolong APD. In normal canine ventricles, in vivo sympathetic stimulation has been observed to shorten the APD and decrease the dispersion of repolarization; however, in LQT1 and LQT2, the effect may be an increased APD in M cells and thus an increased APD dispersion. These effects on the single-cell levels may then be compared with the studies of wedge preparation (see Example 6). All current recordings may be obtained in the whole-cell, voltage-clamp configuration of the patch-clamp technique. The data may be obtained with electrodes whose resistance will be 0.5-2 M'Ω when filled with a standard pipette solution containing (in mmol/L) 130 KCl, 1 MgCl2, 0.5 CaCl2, 10 HEPES, 5 EGTA, 5 Mg2ATP, 5 Na-creatine phosphate, and 0.5 GTP-Tris, pH 7.2 with KOH. The electrodes may be connected to an Axopatch 200B amplifier (Axon Instruments, CA). A DigiData 1322A (Axon Instruments, CA) interface controlled by pClamp 8.1 software (Axon Instruments, CA) may be used to generate the command pulses and to acquire data. After the formation of a high-resistance seal between the recording electrode and the myocyte membrane (5-40 G'Ω in this study), electrode capacitance may be fully compensated electronically before breaking the membrane patch. Cells may be superfused at 1-2 ml/min with Tyrode's solution containing (in mmol/L) 137 NaCl, 5.4 KCl, 1 $MgCl_2$, 0.33 $NaH_2PO_4$, 1 $CaCl_2$, 10 glucose, and 10 HEPES, pH 7.4 with NaOH. Action potentials will be recorded in current-clamp mode in normal Tyrode's solution by injecting suprathreshold current pulses through the patch-clamp electrode. To record the depolarization-activated potassium currents, 2 mmol/L $CoCl_2$ may be used to inhibit $I_{Ca}$. $Mg_2ATP$ in the pipettes may be used to suppress the ATP-sensitive potassium current. Quasi-steady-state activation and inactivation relations may be obtained to further characterize the voltage-dependent properties of the whole-cell current. A normalized (I/Imax) activation relation may be obtained by plotting the peak tail current (I) amplitude, obtained in response to a fixed depolarizing step (+40 to +55 mV) following repolarizing steps from various activating potentials (i.e., $^-60$ to +60 mV), versus the activating potentials. Benzenesulfonamide E-4031 (5 μM) may be used to identify the rapidly activating component of the delayed rectifier current ($I_{Kr}$). The $I_{Ks}$ currents may be identified by their sensitivity to chromanol 293B (30 μM). The inward rectifier potassium current may be recorded in normal Tyrode solution by serial hyperpolarizing steps (1s), from a holding potential of $^-40$ mV to a test potential ranging from $^-50$ mV to $^-130$ mV. The current elicited should display a large inward rectification and should be blocked by barium (1 mM). The remaining E-4031- and chromanol 293B-resistant currents may be tested for their sensitivity to blocking by 4-aminopyridine (4-AP) and tetraethylammonium (TEA). Data may be analyzed by using the Clampfit in pClamp 8.1, Microsoft Excel®, and Microcal® Origin 6.0.

The $I_{Ks}$ (chromanol 293B-sensitive) currents are anticipated to be substantially reduced or completely eliminated in cardiomyocytes derived from KvLQT1-DN hearts. This may produce uniform prolongation of the action potential across all layers of the left ventricle. This is consistent with the lack of TDR at control conditions. By contrast, $I_{Kr}$ (E-4031-sensitive) currents will be substantially reduced or eliminated in ERG-DN rabbits in all layers. However, since mid myocardial cells express sluggish IKs currents, it is expected that the APDs of mid-myocardial cells will be substantially longer than those of epicardial or endocardial cardiomyocytes. In both transgenic rabbits, high expression of $I_{to}$ in epicardial cells is expected. It is important to note that studies of APDs of single cardiomyocytes may yield greater differences between epicardial or endocardial cells and mid-myocardial cells, especially in ERG-DN rabbits, than the APDs that are to be recorded in wedge preparations from groups of cells in these layers because of the homogenizing effect of cell-to-cell coupling present in the intact tissue (see Example 6).

Figure 11:
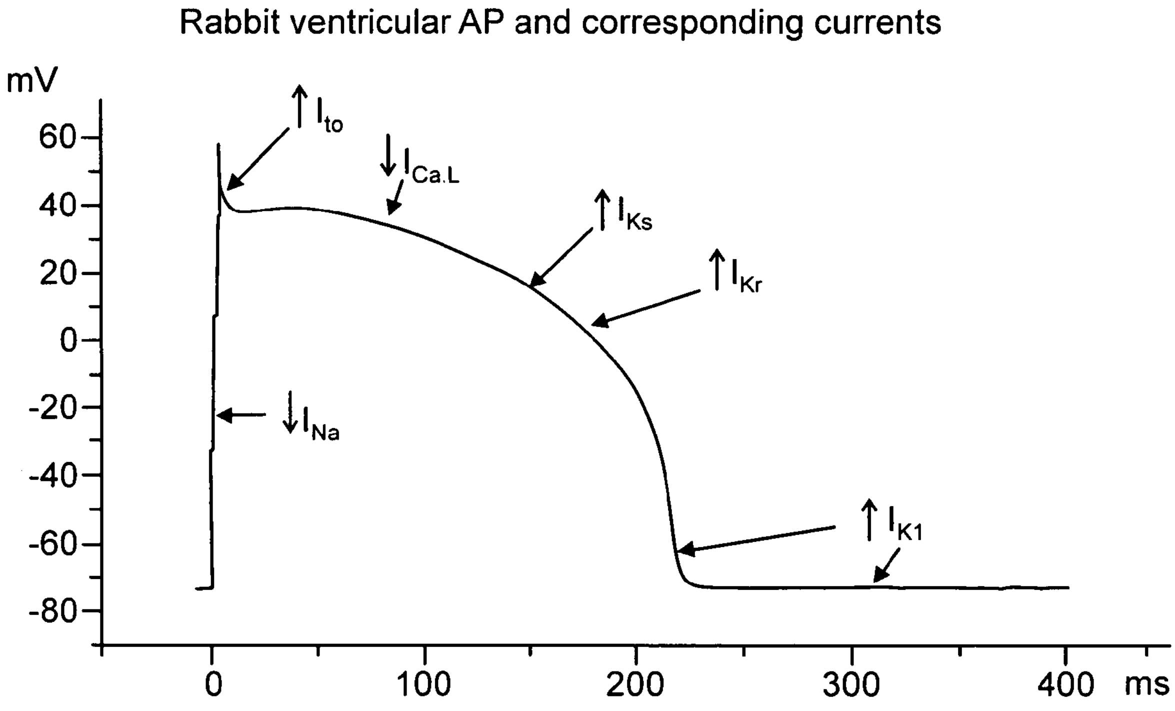
FIG. 11 depicts a typical rabbit ventricular action potential recorded at 1 Hz (37° C.), with principal voltage-gated current participation in various phases of the action potential noted. Inward currents are indicated by downward arrows, and outward currents by upward arrows.
Figure 12A:
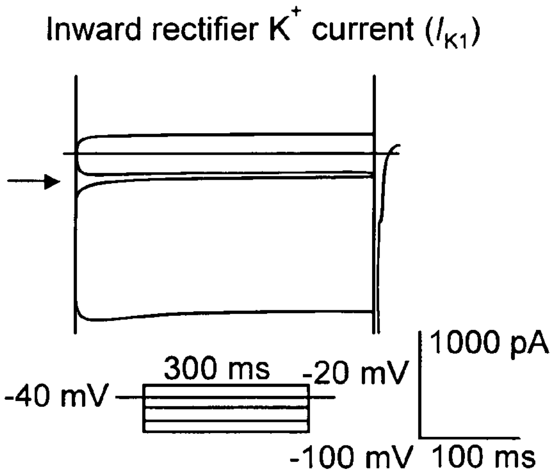
FIG. 12 depicts examples of inward-rectifier (a), transient outward (b), and delayed-rectifier (c) currents recorded from single rabbit ventricular myocytes, with the voltage protocols shown in insets delivered at 0.1 Hz. Experiments were performed at 34-35° C. Slow ($I_{Ks}$) and rapid ($I_{Kr}$) components were separated with the use of 5 μM E-4031.
Figure 12B:
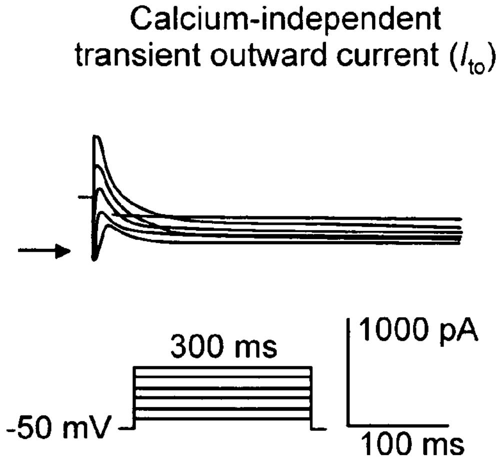
Figure 12C:
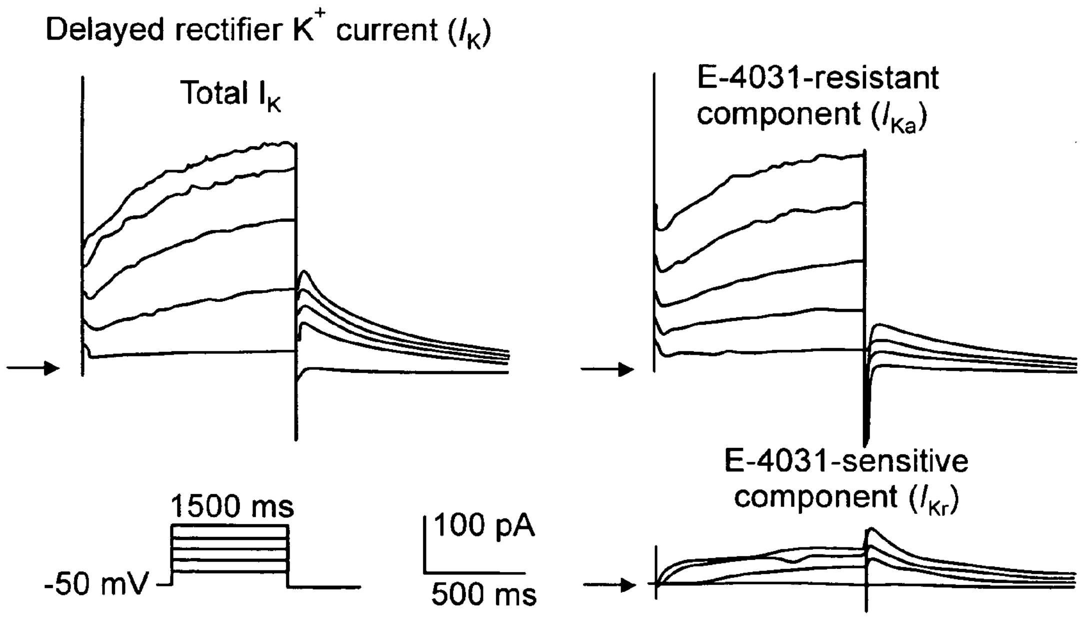

An example of a typical action potential recording of a rabbit ventricular cardiomyocyte is illustrated in FIG. 11, and the inward and outward potassium currents are shown in FIG. 12. Whether the elimination of one of the inward and outward potassium currents will result in a compensatory remodelling of the other potassium current in ventricular myocytes derived from the epicardial or endocardial layers or modulation of the L-type calcium currents expressed in these cells may be determined. If so, it may be the first time that the long-term remodelling of cardiomyocytes derived from a large mammal with genetically induced suppression of $I_{Kr}$ or $I_{Ks}$ will be tested. A gender difference in the expression of $I_{Kr}$ is anticipated, with reduced currents in female rabbits compared with male rabbits. Whether the long-term attenuation of $I_{Ks}$ will modulate $I_{Kr}$ in a gender-specific manner, i.e., will male rabbits be more capable than female rabbits of upregulating $I_{Kr}$, may be tested. Further, whether the epicardial, mid-myocardial, and endocardial surfaces of the heart differentially respond to the prolongation of the APD and the elimination of the different components of the repolarizing currents may be tested. This site-specific or layer-specific remodelling could be critical to the pathogenesis of arrhythmias. Whether the downregulation of $I_{Kr}$ in ERG-DN cardiomyocytes induces remodelling of $I_{Ks}$ may be tested and compared to the remodelling observed in KvLQT1-DN cardiomyocytes. Of note, $I_{Na}$, $I_{to}$, or $I_{K1}$ are not expected to be perturbed by the transgenes, since these currents were not altered in models of overexpression of pore mutants of other voltage-gated potassium channels in the mouse heart. However, as mentioned earlier, prolonged APD is believed to be associated with an increase in calcium influx through L-type Ca2+ channels Voltage clamp studies have consistently been observed to show a greater ratio of $I_{Kr}/I_{Ks}$ currents at the apex than at the base. Using optical mapping of epicardial surface, Choi et al. observed that APDs are slightly shorter at the apex than at the base. Blockade of $I_{Kr}$ by E4031 (0.5 μM) has been observed to prolong APD to >1 s, producing a marked enhancement of the apex-to-base dispersion of repolarization with reversal of repolarization (APDs in the apex longer than base). Thus, whether cells derived from the epicardial layer of the apex and the base of ERG-DN rabbit hearts will have different APDs may be tested. These studies may show whether the observation of Choi et al. obtained in acute pharmacologic studies can be confirmed in a LQT2 model with long-term inhibition of IKr. Collectively, these studies may enable us to compare the long-term differential effects of the dominant negative transgenes KvLQT1-Y315S and HERG-G628S on cardiomyocytes derived from different regions and different layers of the KvLQT1-DN and ERG-DN hearts.

The rabbit $\beta^{-}$-MyHC promoter will likely drive expression of the transgene in slow-twitch skeletal muscle. This is not expected to present a significant problem for the study, since the founders and F1 rabbits are developing normally and reproducing without problems. It is possible that $I_{Kr}$ and $I_{Ks}$ do not play an important role in the function of slow-twitch muscles, but the soleus skeletal muscle may be used as a model system to study the expression of these transgenes.

Example 5

Expression of Adenoviral-Encoded Myc-KvLQT1 Channels in Cardiomyocytes

The efficient delivery and long-term expression of exogenous channels is an important factor for any genetic manipulation of cardiac cell excitation. Adenoviral vectors have been observed to be highly efficient in the delivery of reporter genes into the heart. Adenoviral vectors coding for KvLQT1 may be used to rescue the cellular phenotype of cardiomyocytes derived from KvLQT1-DN rabbits as a proof of principle. KvLQT1 may be tagged with a Myc epitope at the N-terminus and used to infect cultured cardiomyocytes. This system has been successfully with AV-Kv1.5 (Brunner M, Guo W, Mitchell G F, Buckett P, Nerbonne J, Koren G. *Characterization of mice with a combined suppression of $I_{to}$ and $I_{K,slow}$*. American Journal of Physiology 2001; 281: H1201-H1209). As an alternative, the in vivo gene transfer may be accomplished by direct injection into the lateral walls of the left ventricle of the rabbit. These channels may be tagged with a Myc epitope at the N-terminus to distinguish these polypeptides from the endogenous polypeptides and KvLQT1-Y315 S polypeptides that are tagged with a FLAG epitope at the N-terminus. AV-Myc-KvLQT1 is expected to reverse the phenotype of the cardiomyocytes derived from KvLQT1-DN rabbit.

Myocytes may first be infected with AV-Myc-KvLQT1. 72 hours post-infection, the cells may be analyzed for the expression of the encoded channels by immunofluorescence and co-immunoprecipitation assays. The hearts may be removed quickly and rinsed twice in an ice-cold, modified Krebs-Henseleit (K-H) solution containing (in mM): NaCl 112, KCl 4.7, $KH_2PO_4$ 1.2, $MgSO_4$ 1.2, $CaCl_2$ 1.8, Glucose 11, $NaHCO_3$ 25, Na-pyruvate 2, and $Na_2$-EDTA 0.25; the solution saturated with 95% O2+5% CO2 at pH 7.4. The aorta may be cannulated and the hearts perfused using a Langendorff apparatus. The hearts may then be perfused with an enzyme solution containing collagenase I (Worthington) 0.2 mg/ml, and 1% BSA. The ventricles may be removed, chopped, and incubated in the same enzyme solution. The cells may then be repeatedly washed using a series of centrifugations at 500 rpm for 2-3 min and may be resuspended in 0.25, 0.5, and 1.0 mM $Ca^{2+}$-containing K-H solution supplemented with 2% FCS. The cells may then be strained through a 200-μm nylon mesh filter and plated on P30 petri dishes coated with laminin (Collaborative Research, Inc., MA). For in vitro infections, the aliquots of 1011 pfu/ml of adenoviral vectors may be added directly into the culture medium after the myocytes settle onto the bottom of the petri dishes ($5\times10^4$ cells/ml).

The Myc-KvLQT1 cDNA may be cloned into an adenoviral vector coexpressing GFP (AdGFP). As a control, the vehicle may be used alone and AdGFP may be used alone. The infected myocytes may be analyzed for the steady-state levels of the polypeptides of Myc-KvLQT1 and KvLQT1-Y315S. The pattern of expression of the two channels may be studied by detailed immunocytochemistry (as described above) and western blots. In addition, electrophysiological analysis of the outward and inward potassium currents expressed by cardiomyocytes derived from the control and infected myocytes may be carried out to determine whether AdMyc-KvLQT1 rescues the chromanol 293B-sensitive current in KvLQT1-DN rabbits.

The phenotype may be rescued in cultured myocytes. AV-Myc-KvLQT1 may code for a substantial current that may override the rest of the currents in rabbit myocytes, as observed with AV-FL-Kv1.5. If difficulties in maintaining the cells in culture for a sufficient time to observe the rescue of the phenotype are encountered, or if the cells undergo extensive remodelling and substantial decrease in IKr as described by Nuss et al., in vivo injection of the vectors into the myocardium may be used. Using a lateral intercostal incision, the lateral free wall of the left ventricle may be identified and i50 μl containing 1×109 pfu of AV-Myc-KvLQT1 injected. The rabbits may be sacrificed after 7 to 10 days, and the cells harvested for analysis by immunocytochemistry and whole-cell recordings. This series of experiments may prove that an excess of the channel will reverse the expected phenotype of prolonged APD90, spontaneous EADs, and attenuated $I_{Ks}$.

Example 6

To Elucidate the Mechanisms that Trigger and Maintain Arrhythmias in LQT1 and LQT2 Using Left Ventricular Wedge Preparations The arterially-perfused left ventricular wedge preparation may be used to examine the influence of the β adrenergic agonist isoproterenol (10-100 nmol/L) on transmural distribution of electrical activity across the ventricular wall in the KvLQT1-DN and ERG-DN rabbit models of congenital long QT syndrome and littermate controls.

APD of cells at epicardial, M, and endocardial sites and the transmural dispersion of repolarization may be measured. The contribution of transmural electrical heterogeneity induced by isoproterenol to the development of long QT intervals, broad-based T-waves, transmural dispersion of repolarization, and the development of spontaneous and stimulation-induced TdP may be examined. As observed in the canine wedge studies of chromanol 293B perfused wedges, TdP may be observed in the KvLQT1-DN wedges only in the presence of isoproterenol, while in the ERG-DN wedges, TdP may be observed even in the absence of isoproterenol. By contrast, neither spontaneous nor stimulation-induced TdP is expected to be observed in wedge preparations derived from control rabbits. These studies may be used to examine the effects of isoproterenol in the absence of any other drug.

In another series of studies, the arterially perfused left ventricular wedge preparation may be used to examine the effect of the β adrenergic blocker propranolol in suppressing the isoproterenol-induced increase in transmural dispersion of repolarization and TdP in the KvLQT1-DN and ERG-DN rabbit models. The dose-dependent effects of propranolol (0.1-3 μmol/L) on the QT interval and transmural electrical heterogeneity across the left ventricular wall may be examined in these two models. The ability of the β adrenergic blocker to suppress isoproterenol-induced EADs and triggered activity may also be examined.

If methoxamine induces arrhythmia in LQT1 and/or LQT2 rabbits (see above), this α1-adrenoreceptor agonist (1-10 μmol/L) may be added to LV wedge preparation to examine its effects on APD and transmural distribution of electrical activity across the ventricular wall in the KvLQT1-DN and ERG-DN rabbit models and littermate controls. Whether it induces EADs and triggered activity may also be examined. The α1b-antagonist, chloroethylclonidine (0.1-1.0 μmol/L), and the α1α-antagonist, WB-4101 (0.1-1.0 μmol/L), may be used to test which receptor suppresses the methoxamine-induced effects in different layers of the heart.

Collectively, these investigations should advance our understanding of the mechanisms responsible for the genesis and maintenance of TdP, a potentially fatal arrhythmia that often accompanies LQTS. We estimate that a minimum of 20 perfused wedge preparations from each group (1 per rabbit) will be needed to successfully complete each experimental series.

Figure 13:
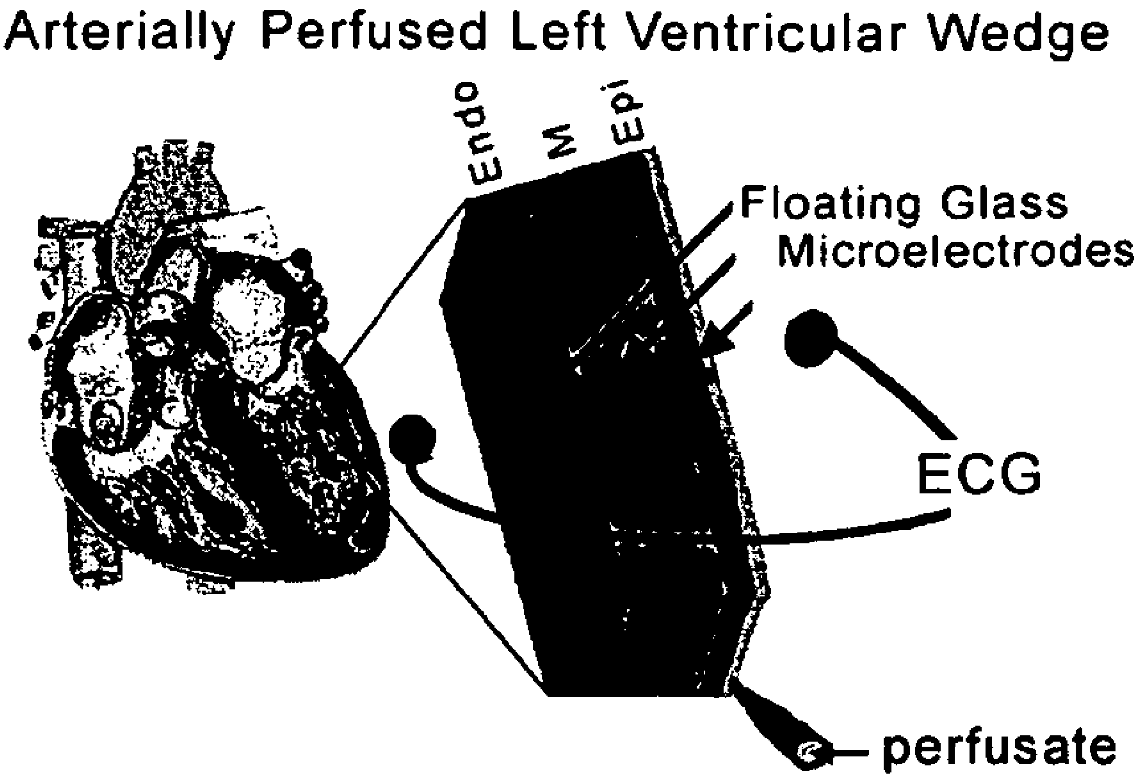
FIG. 13 is a cartoon depicting an arterially perfused left ventricular wedge preparation.

An arterially-perfused wedge of rabbit left ventricle is shown in FIG. 13. Rabbits weighing 2.5 3.5 kg may be anticoagulated with heparin and anesthetized with pentobarbital (30-35 mg/kg, i.v.). Transmural wedges with dimensions of approximately 2×1.5×0.9 cm to 3×2×1.5 cm may be dissected from the left ventricle. The tissue may be cannulated via a small (diameter ~100 μm) native branch of the left descending coronary artery and perfused with cardioplegic solution. Unperfused tissue may be carefully removed using a razor blade. The preparation may then be placed in a small tissue bath and arterially perfused with Tyrode's solution of the following composition (mM): 129 NaCl, 4 KCl, 0.9 NaH2PO4, 20 NaHCO3, 1.8 CaCl2, 0.5 MgSO4, 5.5 glucose, buffered with 95% O2 and 5% CO2 (37±1° C.). The preparations may be stimulated at basic cycle lengths ranging from 300 to 2,000 msec using bipolar silver electrodes insulated (except at the tips) and applied to the endocardial surface. A transmural ECG may be recorded using electrodes consisting of AgCl half cells attached to Tyrode's-filled tapered polyethylene electrodes which will be placed in the Tyrode's solution bathing the preparation, 1.0 to 1.5 cm from the epicardial and endocardial surfaces of the preparation, along the same vector as the transmembrane recordings. In previous experiments, the morphology of the ECG was observed to be not altered other than in amplitude when the distance of the electrodes from the preparation is increased beyond 1 cm. Thus, the electrocardiographic registration is believed to represent a pseudo-ECG. Transmembrane action potentials may be simultaneously recorded from epicardial, M, and endocardial sites using three to four separate intracellular floating microelectrodes (DC resistance: 10 to 20 MΩ) filled with 2.7 M KCl and connected to a high-input impedance amplifier.

Impalements may be obtained from the cut surface and from epicardial and endocardial surfaces of the preparation at positions approximating the transmural axis of the ECG recording. Plunge electrodes, consisting of silver wire (50-120 μm diameter) insulated with Teflon except at the tip, may be introduced to various depths within the preparation using a 21- or higher-gauge needle, which may be immediately withdrawn. Each electrode may be referenced to the bath ground (AgCl electrode). Each unipolar recording may be differentiated, and the activation recovery interval (ARI) approximating the action potential duration at each site may be measured as the interval between the time minimum of the first derivative (Vmin) of the QRS deflection and the maximum first derivative (Vmax) of the T-wave. ARI may be compared with either APD at 90% repolarization (APD90) or the interval between Vmax and Vmin of the differentiated action potential trace. All amplified signals may be digitized, stored, and analyzed using Spike 2 (Cambridge Electronic Design, Cambridge, UK-CED).

Figures 14A, 14B, 14C:
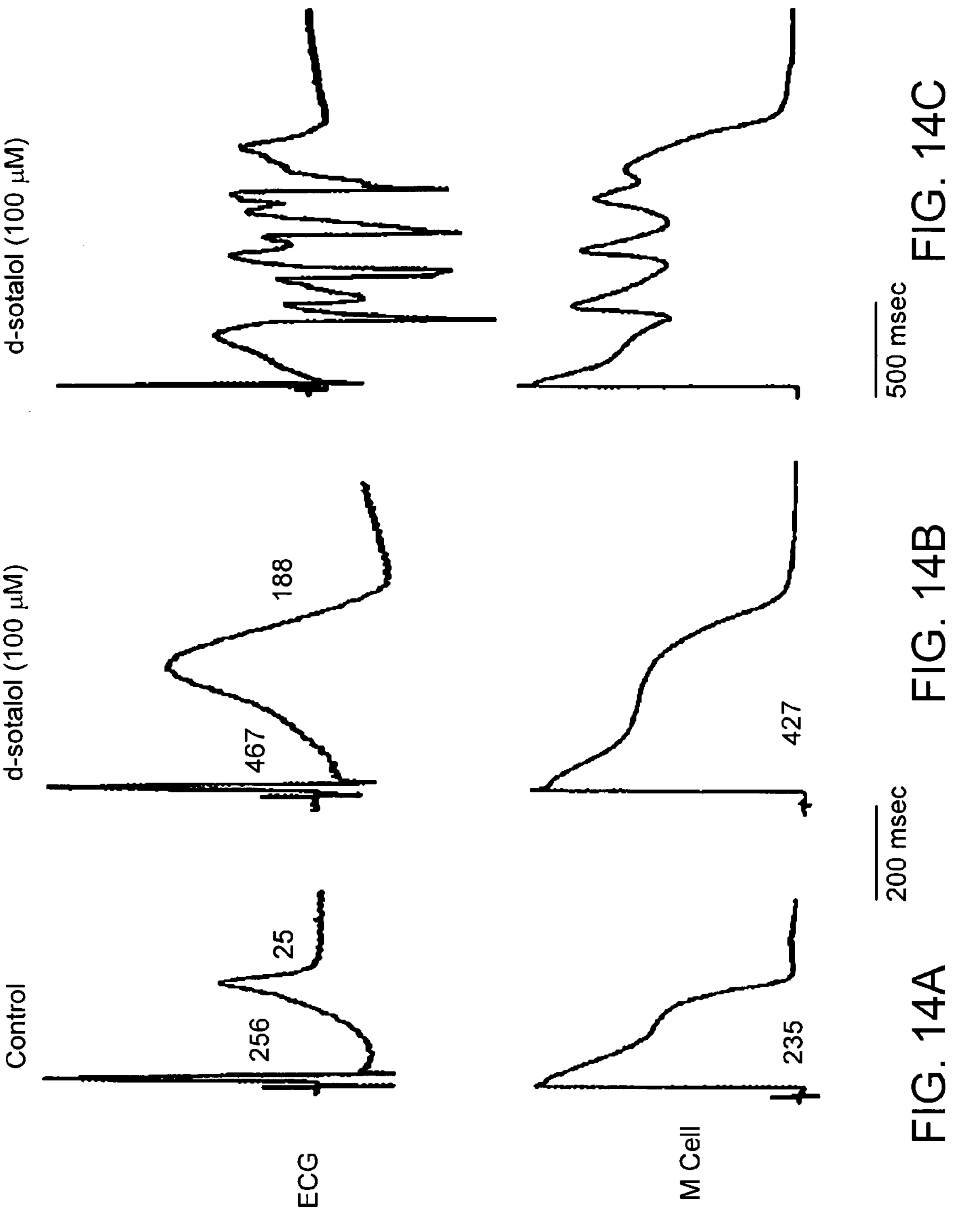
FIG. 14 depicts the Sotalol-induced increase in transmural dispersion of repolarization (Tpeak-Tend) and induction of TdP in the rabbit left ventricular wedge preparation. Shown are floating microelectrode recordings from an M cell in the subendocardial region of the wedge preparation and an ECG recorded across the bath. Action potential duration at 90% repolarization (APD90) was 235 msec and 427 msec after the addition of d-sotalol (100 μM). QT interval increased from 235 to 467, and Tpeak-Tend (an index of transmural dispersion of repolarization) increased from 28 to 188 msec. A brief episode of spontaneous TdP occurs in the presence of d-sotalol (100 μM) (Panel C).

In both KvLQT1 and ERG-DN models, we anticipate recording a relatively long QT interval with abnormal T-waves. As with other models of congenital and acquired LQTS, we anticipate recording an increased transmural dispersion of repolarization, manifest as relatively large differences in the repolarization time of the three principal cell types within the ventricular myocardium and as the presence of a prolonged Tpeak-Tend interval in the ECG. These models should also provide insights into the cellular mechanisms responsible for the development of life-threatening TdP arrhythmias and the mechanism by which sympathetic stimuli precipitate lethal events. Examples of these characteristics of the rabbit left ventricular wedge are illustrated in FIG. 14.

In LQT1 and LQT2 experimental models, preferential prolongation of the M cell APD has been observed to lead to an increase in the QT interval as well as to an increase in TDR, the latter providing the substrate for the development of spontaneous as well as stimulation-induced TdP. M cells differ from epicardial and endocardial cells in that they display a much greater APD at slow rates. A weaker $I_{Ks}$ and a larger "late sodium current" contribute to the longer action potential of the M cell (in the dog). The weaker net outward current active during the plateau phase also contributes to the greater response of M cells to agents that produce APD prolongation. At slow rates, M cells show a preferential response to agents that inhibit IK (e.g., quinidine, erythromycin, sotalol, E-4031), augment $I_{Ca}$ (e.g., BAY K 8644) or slow the inactivation of $I_{Na}$ (e.g. ATX-II). Preferential prolongation of the M cell APD under these conditions results in a prolongation of the QT interval as well as an increase in transmural dispersion of repolarization. In the KvLQT1-DN model, we therefore expect to encounter a relatively uniform prolongation of APD in all three-cell types with relatively little change in TDR. Although the QT interval is prolonged, TdP may not occur under these conditions because of the insufficient TDR. Addition of isoproterenol would be expected to result in abbreviation of epicardial and endocardial APD, while the M-cell APD either becomes prolonged or remains the same. The increase in TDR would be expected to provide the substrate for the development of spontaneous as well as stimulation-induced TdP. These findings would be consistent with the high sensitivity of patients with congenital LQT1 to sympathetic stimulation. The results would also support the hypothesis that the problem with the long QT syndrome is not the long QT interval itself but rather the increase in TDR that often accompanies prolongation of the QT interval. In the ERG-DN model, although all three-cell types may exhibit a prolonged APD, the M cell APD is expected to be even longer, resulting in accentuation of TDR and spontaneous and stimulation-induced TdP. Isoproterenol would be expected to further exaggerate TDR and thus increase the incidence of TdP in this model.

The response to sympathetic activation displays a very different time course in the case of LQT1 and LQT2, both in experimental models and in the clinic. In LQT1, β adrenergic stimulation has been observed to induce an increase in TDR that is most prominent during the first 2 minutes, but which persists, although to a lesser extent, at a steady-state thereafter. TdP incidence is observed to be enhanced during the initial period as well as during steady-state. In LQT2, isoproterenol appears to produce only a transient increase in TDR that persists for less than 2 minutes. TdP incidence is therefore enhanced only for a brief period. These differences in time course may explain the important changes in autonomic activity and other gene-specific triggers that contribute to events in patients with different LQTS genotypes. We expect to encounter similar differences in time courses of the action of sympathetic stimulation in the KvLQT1-DN and ERG-DN rabbit models. β blockers are considered the first line of therapy in patients with LQT1. We anticipate that β blockers will reduce dispersion of repolarization in our transgenic rabbit models, particularly in ERG-DN rabbits. These studies of wedge preparations will be compared and contrasted with the APDs, outward potassium currents, and inward calcium currents of single cells derived from epicardial, mid-myocardial, and endocardial layers from the same region from which the wedge preparations will be taken, as well as with the biochemical studies (see above).

In his original studies, Carlsson noted that pretreatment with prazosin was as effective as pretreatment with propranolol in suppressing the arrhythmias in his rabbit model. Methoxamine infusion has been shown to prolong the QTc in a patient with LQTS. The activation of PKC pathway by α1-adrenoreceptor agonists has a complex and variable effect on cardiomyocytes. The list of cardiac channels modulated by PKC includes $I_{Ks}$, $I_{Kr}$, $I_{to}$, $I_{Kl}$, $I_{Ca}$, L, $I_{Na}$, and the Na/H+ exchanger. Thus, the net effect of methoxamine on the APD at different layers of the heart is hard to predict. Of note, methoxamine produced a dose- and rate-dependent prolongation of APD90 in Purkinje fibers, but an abbreviation of APD90 in tissues from the M region in canine wedge preparations as a result of its interaction with different α1-adrenoreceptors subtypes. We reason that studying the differential effects of methoxamine on epicardial mid-myocardial and endocardial layers of the myocardium will likely reveal the mechanism that underlies the proarrhythmic effect of methoxamine in LQT rabbits.

Optical mapping of the wedge preparation for simultaneous endocardial and epicardial recordings may be used to look at triggers and substrate of TdP. The optical mapping will complement our studies by localizing the precise site of origin of the triggered arrhythmia, and if dispersion is indeed involved, the studies could localize the site of initiation of reentry. While M cells might be involved in initiating the arrhythmias, at this point we cannot rule out the possibility that the EADs are formed in the Purkinje fibers. Optical mapping of Langendorff-perfused hearts of LQT1 and LQT2 rabbits may be carried out to characterize properties such as frequency dependence of APD, conduction velocity, and dynamics of reentry. Questions as to whether the transgenic hearts show more complex patterns of reentry and fibrillation than hearts from littermate control rabbits could be addressed. If there is significant dispersion of APD at high frequencies, the patterns of fibrillatory conduction and wavelet formation should be more complex in the transgenic rabbits than in the controls. We believe that our multi-pronged approach to studying the phenotype of these LQT rabbits will likely yield important information regarding the mechanisms that underlie the arrhythmias in LQTS.

EQUIVALENTS

The present invention provides, among other things, novel animal models of LQTS. While specific embodiments of the subject invention have been discussed, the above specification is illustrative and not restrictive. Many variations of the invention will become apparent to those skilled in the art upon review of this specification. The appended claims are not intended to claim all such embodiments and variations, and the full scope of the invention should be determined by reference to the claims, along with their full scope of equivalents, and the specification, along with such variations.

REFERENCES

The practice of the present invention will employ, unless otherwise indicated, conventional techniques of cell biology, cell culture, molecular biology, transgenic biology, microbiology, recombinant DNA, and immunology, which are within the skill of the art. Such techniques are described in the literature. See, for example, *Molecular Cloning A Laboratory Manual,* 2nd Ed., ed. by Sambrook, Fritsch and Maniatis (Cold Spring Harbor Laboratory Press: 1989); *DNA Cloning*, Volumes I and II (D. N. Glover ed., 1985); *Oligonucleotide Synthesis* (M. J. Gait ed., 1984); Mullis et al. U.S. Pat. No. 4,683,195; *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Methods In Enzymology*, Vols. 154 and 155 (Wu et al. eds.), *Immunochemical Methods In Cell And Molecular Biology* (Mayer and Walker, eds., Academic Press, London, 1987); *Handbook Of Experimental Immunology*, Volumes I-IV (D. M. Weir and C. C. Blackwell, eds., 1986); *Manipulating the Mouse Embryo*, (Cold Spring Harbor Laboratory Press, Cold Spring Harbor, N.Y., 1986).

All publications and patents mentioned herein, including those items listed below, are hereby incorporated by reference in their entirety as if each individual publication or patent was specifically and individually indicated to be incorporated by reference. In case of conflict, the present application, including any definitions herein, will control.

1. Article by Wojciech Zareba, MD, PhD, FACC on http://www.emedicine.com/med/topic1983.htm
2. Valverde P, Koren G. *Purification and preliminary characterization of a Kv1.5 repressor element binding factor*. Circulation Research 1999; 84:937-944.
3. Jeron A, Mitchell G F, Zhou J, Murata M, London B, Buckett P, Wiviott S D, Koren G. *Inducible polymorphic ventricular tachycardia in a transgenic mouse model with a long QT phenotype*. American Journal of Physiology 2000; 278: H1891-H1898.
4. Baker L C, London B, Chio B R, Koren G, Salama G. *Enhanced dispersion of repolarization and refractoriness in transgenic mice hearts promotes reentrant ventricular tachycardia*. Circulation Research 2000; 86: 396-407.
5. Brunner M, Guo W, Mitchell G F, Buckett P, Nerbonne J, Koren G. *Characterization of mice with a combined suppression of $I_{to}$ and $I_{K,slow}$*. American Journal of Physiology 2001; 281: H1201-H1209.
6. Zhou J, Kodirov S, Murata M, Buckett P, Nerbonne J M, Koren G. *Apical upregulation of Kv2.1-encoded current, $I_{k,slow2}$ in Kv1DN* mice is abolished by crossbreeding with Kv2*DN mice*. American Journal of Physiology 2003; 284: H491-H500.
7. Brunner M, Kodirov S, Mitchell G, Buckett P, Shibata K, Folco E, Baker L, Salama G, Chan D, Zhou J, Koren G. In vivo gene therapy of Kv1.5 normalizes action potential duration and shortens QT interval in mice with Long QT phenotype. American Journal of Physiology 2003; 285: H194-H203.
8. Kodirov S A, Brunner M, Busconi L, Koren G. *Long-term restitution of 4-aminopyritidine-sensitive currents in Kv1DN ventricular myocytes using adeno-associated virus-mediated delivery of Kv1.5*. FEBS Letters 2003; 550: 74-78.
9. Kodirov S A, Brunner M, Nerbonne J M, Buckett P, Mitchell G F, Koren G. *Attenuation of $I_{K,slow1}$ and $I_{K,slow2}$ in Kv1DN mice prolongs the APD and QT intervals but does not prevent spontaneous or inducible arrhythmias*. American Journal of Physiology 2003; In Press.
10. Pang L, Koren G, Wang Z, Nattel S. *Tissue-specific expressions of two human $Ca_v1.2$ isoforms under the control of distinct 5'-flanking regulatory elements*. FEBS Letters 2003; 543:349-354.
11. Folco E J, Roder K, Mitchell G F, Koren G. "*Cardiac memory" a struggle against forgetting* (*Editorial*). Circulation Research 2003; 93: 384-386.
12. Liu G-X, Zhou j, Nattel S, Koren G. Liu G-X, Zhou j, Nattel S, Koren G. *Single-channel recordings of a rapid delayed rectifier current in adult mouse ventricular myocytes: basic properties and effects of divalent cations. Journal of Physiology* (London) 2004; 556: 401-413.
13. Liu, G. X., et al., *Single-channel recordings of a rapid delayed rectifier current in adult mouse ventricular myocytes: basic properties and effects of divalent cations*. J Physiol, 2004. 556(Pt 2): p. 401-13.
14. Wilson, T. E., et al., *Identification of the DNA binding site for NGFI-B by genetic selection in yeast*. Science, 1991. 252(5010): p. 1296-300.
15. Law, S. W., et al., *Identification of a new brain-specific transcription factor, NURR1*. Mol Endocrinol, 1992. 6(12): p. 2129-35.
16. Ohkura, N., et al., *Molecular cloning of a novel thyroid/steroid receptor superfamily gene from cultured rat neuronal cells*. Biochem Biophys Res Commun, 1994. 205(3): p. 1959-65.
17. Mangelsdorf, D. J., et al., *The nuclear receptor superfamily: the second decade*. Cell, 1995. 83(6): p. 835-9.
18. Saucedo-Cardenas, O., et al., *Nurr1 is essential for the induction of the dopaminergic phenotype and the survival of ventral mesencephalic late dopaminergic precursor neurons*. Proc Natl Acad Sci USA, 1998. 95(7): p. 4013-8.
19. Le, W. D., et al., *Mutations in NR4A2 associated with familial Parkinson disease*. Nat Genet, 2003. 33(1): p. 85-9.
20. Hering, R., et al., *Extended mutation analysis and association studies of Nurr1* (NR4A2) *in Parkinson disease*. Neurology, 2004. 62(7): p. 1231-2.
21. Ishizaki, F., et al., *Prolonged QTc intervals in Parkinson's disease—relation to sudden death and autonomic dysfunction*. No To Shinkei, 1996. 48(5): p. 443-8.
22. Liu, D. W. and C. Antzelevitch, *Characteristics of the delayed rectifier current (IKr and IKs) in canine ventricular epicardial, midmyocardial, and endocardial myocytes. A weaker IKs contributes to the longer action potential of the M cell*. Circ Res, 1995. 76(3): p. 351-65.
23. Tristani-Firouzi, M., et al., *Molecular biology of K(+) channels and their role in cardiac arrhythmias*. Am J Med, 2001. 110(1): p. 50-9.
24. Nerbonne, J. M., *Molecular basis of functional voltage-gated K+ channel diversity in the mammalian myocardium*. J Physiol, 2000. 525: p. 285-98.
25. Curran, M. E., et al., *A molecular basis for cardiac arrhythmia: HERG mutations cause long QT syndrome. Cell,* 1995. 80(5): p. 795-803.
26. Wang, Q., et al., *Positional cloning of a novel potassium channel gene: KvLQT1 mutations cause cardiac arrhythmias*. Nat Genet, 1996. 12(1): p. 17-23.
27. Abbott, G. W., et al., *MiRP1 forms $I_{Kr}$ potassium channels with HERG and is associated with cardiac arrhythmia*. Cell, 1999. 97(2): p. 175-87.
28. Weerapura, M., et al., *A comparison of currents carried by HERG, with and without coexpression of MiRP1, and the native rapid delayed rectifier current. Is MiRP1 the missing link?* J Physiol, 2002. 540: p. 15-27.
29. Sanguinetti, M. C. and N. K. Jurkiewicz, *Two components of cardiac delayed rectifier K+ current. Differential sensi-*

*tivity to block by class III antiarrhythmic agents.* J Gen Physiol, 1990. 96(1): p. 195-215.

30. Attali, B., Ion channels. *A new wave for heart rhythms.* Nature, 1996. 384(6604): p. 24-5.

31. Barhanin, J., et al., *K(V)LQT1 and lsK (minK) proteins associate to form the I(Ks) cardiac potassium current.* Nature, 1996. 384(6604): p. 78-80.

32. Sanguinetti, M. C., et al., *Coassembly of K(V)LQT1 and minK (IsK) proteins to form cardiac I(Ks) potassium channel.* Nature, 1996. 384(6604): p. 80-3.

33. Wang, Q., et al., *SCN5A mutations associated with an inherited cardiac arrhythmia, long QT syndrome.* Cell, 1995. 80(5): p. 805-11.

34. Moss, A. J. and P. J. Schwartz, *Sudden death and the idiopathic long Q-T syndrome.* Am J Med, 1979. 66(1): p. 6-7.

35. Roden, D. M. and B. F. Hoffman, *Action potential prolongation and induction of abnormal automaticity by low quindine concentrations in canine Purkinje fibers: Relationship to potassium and cycle length.* Circ Res, 1986. 56: p. 857-867.

36. Davidenko, J. M., et al., *Quinidine-induced action potential prolongation, early afterdepolarizations, and triggered activity in canine Purkinje fibers. Effects of stimulation rate, potassium, and magnesium.* Circulation, 1989. 79(3): p. 674-86.

37. Shimizu, W., et al., *Early afterdepolarizations induced by isoproterenol in patients with congenital long QT syndrome.* Circulation, 1991. 84(5): p. 1915-23.

38. Shimizu, W., et al., *Effects of verapamil and propranolol on early afterdepolarizations and ventricular arrhythmias induced by epinephrine in congenital long QT syndrome.* J Am Coll Cardiol, 1995. 26(5): p. 1299-309.

39. el-Sherif, N., et al., *The electrophysiological mechanism of ventricular arrhythmias in the long QT syndrome. Tridimensional mapping of activation and recovery patterns.* Circ Res, 1996. 79(3): p. 474-92.

40. January, C. T., J. M. Riddle, and J. J. Salata, *A model for early afterdepolarizations: induction with the Ca2+* channel agonist Bay K 8644. *Circ Res,* 1988. 62(3): p. 563-71.

41. Moss, A. J., et al., *ECG T-wave patterns in genetically distinct forms of the hereditary long QT syndrome.* Circulation, 1995. 92(10): p. 2929-34.

42. Gbadebo, T. D., et al., *Calmodulin inhibitor W-7 unmasks a novel electrocardiographic parameter that predicts initiation of torsade de pointes.* Circulation, 2002. 105(6): p. 770-4.

43. Antzelevitch, C. and W. Shimizu, *Cellular mechanisms underlying the long QT syndrome.* Curr Opin Cardiol, 2002. 17(1): p. 43-51.

44. Roberds, S. L. and M. M. Tamkun, *Cloning and tissue-specific expression of five voltage-gated potassium channel cDNAs expressed in rat heart.* Proc Natl Acad Sci USA, 1991. 88(5): p. 1798-802.

45. Tseng-Crank, J. C., et al., *Molecular cloning and functional expression of a potassium channel cDNA isolated from a rat cardiac library.* FEBS Lett, 1990. 268(1): p. 63-8.

46. Matsubara, H., et al., *Pretranslational mechanisms determine the type of potassium channels expressed in the rat skeletal and cardiac muscles.* J Biol Chem, 1991. 266(20): p. 13324-8.

47. Drewe, J. A., et al., *Distinct spatial and temporal expression patterns of K+ channel mRNAs from different subfamilies.* J Neurosci, 1992. 12(2): p. 538-48.

48. Dixon, J. E. and D. McKinnon, *Quantitative analysis of potassium channel mRNA expression in atrial and ventricular muscle of rats.* Circ Res, 1994. 75(2): p. 252-60.

49. Benndorf, K., *Three types of single K channels contribute to the transient outward current in myocardial mouse cells.* Biomed Biochim Acta, 1988. 47(4-5): p. 401-16.

50. Nerbonne, J. M., et al., *Genetic manipulation of cardiac K(+) channel function in mice: what have we learned, and where do we go from here?* Circ Res, 2001. 89(11): p. 944-56.

51. Guo, W., et al., *Molecular basis of transient outward K+ current diversity in mouse ventricular myocytes.* J Physiol, 1999. 521 Pt 3: p. 587-99.

52. Guo, W., et al., *Functional consequences of elimination of i(to,f) and i(to,s): early afterdepolarizations, atrioventricular block, and ventricular arrhythmias in mice lacking Kv1.4 and expressing a dominant-negative Kv4 alpha subunit.* Circ Res, 2000. 87(1): p. 73-9.

53. Wickenden, A. D., et al., *Targeted expression of a dominant-negative K(v)4.2 K(+) channel subunit in the mouse heart.* Circ Res, 1999. 85(11): p. 1067-76.

54. Kuo, H. C., et al., *A defect in the Kv channel-interacting protein 2 (KChIP2) gene leads to a complete loss of I(to) and confers susceptibility to ventricular tachycardia.* Cell, 2001. 107(6): p. 801-13.

55. Wang, Z., et al., *Potential molecular basis of different physiological properties of the transient outward K+ current in rabbit and human atrial myocytes.* Circ Res, 1999. 84(5): p. 551-61.

56. Barry, D. M., et al., *Functional knockout of the transient outward current, long-QT syndrome, and cardiac remodeling in mice expressing a dominant-negative Kv4 alpha subunit.* Circ Res, 1998. 83(5): p. 560-7.

57. Xu, H., et al., *Attenuation of the slow component of delayed rectification, action potential prolongation, and triggered activity in mice expressing a dominant-negative Kv2 alpha subunit.* Circ Res, 1999. 85(7): p. 623-33.

58. London, B., et al., *Long QT and ventricular arrhythmias in transgenic mice expressing the N terminus and first transmembrane segment of a voltage-gated potassium channel.* Proc Natl Acad Sci USA, 1998. 95(6): p. 2926-31.

59. Xu, H., W. Guo, and J. M. Nerbonne, *Four kinetically distinct depolarization-activated K+ currents in adult mouse ventricular myocytes.* J Gen Physiol, 1999. 113(5): p. 661-78.

60. Zhou, J., et al., *Regional upregulation of Kv2.1-encoded current, IK,slow2, in Kv1DN mice is abolished by crossbreeding with Kv2DN mice.* Am J Physiol Heart Circ Physiol, 2003. 284(2): p. H491-500.

61. Kodirov, S., et al., *Attenuation of IK,slow1 and IK,slow2 in Kv1/Kv2DN mice prolongs the APD and QT intervals but does not suppress spontaneous or inducible arrhythmias.* American Journal of Physiology, 2003. In press.

62. Nuss, H. B. and E. Marban, *Electrophysiological properties of neonatal mouse cardiac myocytes in primary culture.* J Physiol, 1994. 479: p. 265-79.

63. Wymore, R. S., et al., *Tissue and species distribution of mRNA for the IKr-like K+ channel,* erg. Circ Res, 1997. 80(2): p. 261-8.

64. Zhou, J., et al., *Characterization of a slowly inactivating outward current in adult mouse ventricular myocytes.* Circ Res, 1998. 83(8): p. 806-14.

65. Wang, L., et al., *Developmental changes in the delayed rectifier K+ channels in mouse heart.* Circ Res, 1996. 79(1): p. 79-85.

66. Lees-Miller, J. P., et al., *Selective knockout of mouse ERG1 B potassium channel eliminates I(Kr) in adult ven-*

*tricular myocytes and elicits episodes of abrupt sinus bradycardia*. Mol Cell Biol, 2003. 23(6): p. 1856-62.
67. Babij, P., et al., *Inhibition of cardiac delayed rectifier K+ current by overexpression of the long-QT syndrome HERG G628S mutation in transgenic mice*. Circ Res, 1998. 83(6): p. 668-78.
68. Demolombe, S., et al., *Transgenic mice overexpressing human KvLQT1 dominant-negative isoform. Part I: Phenotypic characterisation*. Cardiovasc Res, 2001. 50(2): p. 314-27.
69. Vetter, D. E., et al., *Inner ear defects induced by null mutation of the isk gene*. Neuron, 1996. 17(6): p. 1251-64.
70. Kupershmidt, S., et al., *Replacement by homologous recombination of the minK gene with lacZ reveals restriction of minK expression to the mouse cardiac conduction system*. Circ Res, 1999. 84(2): p. 146-52.
71. Lee, M. P., et al., *Targeted disruption of the Kvlqt1 gene causes deafness and gastric hyperplasia in mice*. J Clin Invest, 2000. 106(12): p. 1447-55.
72. Casimiro, M. C., et al., *Targeted disruption of the Kcnq1 gene produces a mouse model of Jervell and Lange-Nielsen Syndrome*. Proc Natl Acad Sci USA, 2001. 98(5): p. 2526-31.
73. Drici, M. D., et al., *Involvement of IsK-associated K+ channel in heart rate control of repolarization in a murine engineered model of Jervell and Lange-Nielsen syndrome*. Circ Res, 1998. 83(1): p. 95-102.
74. Giles, W. R. and A. C. van Ginneken, *A transient outward current in isolated cells from the crista terminalis of rabbit heart*. J Physiol, 1985. 368: p. 243-64.
75. Varro, A., et al., *Ionic currents and action potentials in rabbit, rat, and guinea pig ventricular myocytes*. Basic Res Cardiol, 1993. 88(2): p. 93-102.
76. Dixon, J. E., et al., *Role of the Kv4.3 K+ channel in ventricular muscle. A molecular correlate for the transient outward current*. Circ Res, 1996. 79(4): p. 659-68.
77. Lengyel, C., et al., *Pharmacological block of the slow component of the outward delayed rectifier current (I(Ks)) fails to lengthen rabbit ventricular muscle QT(c) and action potential duration*. Br J Pharmacol, 2001. 132(1): p. 101-10.
78. Tsuji, Y., et al., *Ionic mechanisms of acquired QT prolongation and torsades de pointes in rabbits with chronic complete atrioventricular block*. Circulation, 2002. 106 (15): p. 2012-8.
79. Liu, Y. B., et al., *Sympathetic nerve sprouting, electrical remodeling, and increased vulnerability to ventricular fibrillation in hypercholesterolemic rabbits*. Circ Res, 2003. 92(10): p. 1145-52.
80. Lathrop, D. A., et al., *Ionic basis for OPC-8212-induced increase in action potential duration in isolated rabbit, guinea pig and human ventricular myocytes*. Eur J Pharmacol, 1993. 240(2-3): p. 127-37.
81. Lu, Z., et al., *Density and kinetics of I(Kr) and I(Ks) in guinea pig and rabbit ventricular myocytes explain different efficacy of I(Ks) blockade at high heart rate in guinea pig and rabbit: implications for arrhythmogenesis in humans*. Circulation, 2001. 104(8): p. 951-6.
82. Chinn, K., *Two delayed rectifiers in guinea pig ventricular myocytes distinguished by tail current kinetics*. J Pharmacol Exp Ther, 1993. 264(2): p. 553-60.
83. Virag, L., et al., *The slow component of the delayed rectifier potassium current in undiseased human ventricular myocytes*. Cardiovasc Res, 2001. 49(4): p. 790-7.
84. Stengl, M., et al., *Accumulation of slowly activating delayed rectifier potassium current (IKs) in canine ventricular myocytes*. J Physiol, 2003. 551: p. 777-86.
85. Mitcheson, J. S. and J. C. Hancox, *An investigation of the role played by the E-4031-sensitive (rapid delayed rectifier) potassium current in isolated rabbit atrioventricular nodal and ventricular myocytes*. Pflugers Arch, 1999. 438 (6): p. 843-50.
86. Carlsson, L., O. Almgren, and G. Duker, *QTU-prolongation and torsades de pointes induced by putative class III antiarrhythmic agents in the rabbit: etiology and interventions*. J Cardiovasc Pharmacol, 1990. 16(2): p. 276-85.
87. Lu, H. R., et al., *Species plays an important role in drug-induced prolongation of action potential duration and early afterdepolarizations in isolated Purkinje fibers*. J Cardiovasc Electrophysiol, 2001. 12(1): p. 93-102.
88. Zicha, S., et al., *Molecular basis of species-specific expression of repolarizing K+ currents in the heart*. Am J Physiol Heart Circ Physiol, 2003. 285(4): p. H1641-9.
89. Nuss, H. B., E. Marban, and D. C. Johns, *Overexpression of a human potassium channel suppresses cardiac hyperexcitability in rabbit ventricular myocytes*. J Clin Invest, 1999. 103(6): p. 889-96.
90. Fan, J. and T. Watanabe, *Transgenic rabbits as therapeutic protein bioreactors and human disease models*. Pharmacol Ther, 2003. 99(3): p. 261-82.
91. James, J., et al., *Genetic manipulation of the rabbit heart via transgenesis*. Circulation, 2000. 101(14): p. 1715-21.
92. Marian, A. J., et al., *A transgenic rabbit model for human hypertrophic cardiomyopathy*. J Clin Invest, 1999. 104 (12): p. 1683-92.
93. Patel, R., et al., *Simvastatin induces regression of cardiac hypertrophy and fibrosis and improves cardiac function in a transgenic rabbit model of human hypertrophic cardiomyopathy*. Circulation, 2001. 104(3): p. 317-24.
94. James, J., et al., *Transgenic rabbits expressing mutant essential light chain do not develop hypertrophic cardiomyopathy*. J Mol Cell Cardiol, 2002. 34(7): p. 873-82.
95. Donger, C., et al., *KVLQT1 C-terminal missense mutation causes aformefruste long-QT syndrome*. Circulation, 1997. 96(9): p. 2778-81.
96. Sanguinetti, M. C., et al., *Spectrum of HERG K+-channel dysfunction in an inherited cardiac arrhythmia*. Proc Natl Acad Sci USA, 1996. 93(5): p. 2208-12.
97. Chouabe, C., et al., *Properties of KvLQT1 K+ channel mutations in Romano-Ward and Jervell and Lange-Nielsen inherited cardiac arrhythmias*. Embo J, 1997. 16(17): p. 5472-9.
98. Babila, T., et al., *Assembly of mammalian voltage-gated potassium channels: evidence for an important role of the first transmembrane segment*. Neuron, 1994. 12(3): p. 615-26.
99. Folco, E., et al., *A cellular model for long QT syndrome. Trapping of heteromultimeric complexes consisting of truncated Kv1.1 potassium channel polypeptides and native Kv1.4 and Kv1.5 channels in the endoplasmic reticulum*. J Biol Chem, 1997. 272(42): p. 26505-10.
100. Mathur, R., et al., *Ile-177 and Ser-180 in the S1 segment are critically important in Kv1.1 channel function*. J Biol Chem, 1999. 274(17): p. 11487-93.
101. Mitchell, G. F., A. Jeron, and G. Koren, *Measurement of heart rate and Q-T interval in the conscious mouse*. Am J Physiol, 1998. 274(3): p. H747-51.
102. Jeron, A., et al., *Inducible polymorphic ventricular tachyarrhythmias in a transgenic mouse model with a long Q-T*

*phenotype*. Am J Physiol Heart Circ Physiol, 2000. 278(6): p. H1891-8.

103. Baker, L. C., et al., *Enhanced dispersion of repolarization and refractoriness in transgenic mouse hearts promotes reentrant ventricular tachycardia*. Circ Res, 2000. 86(4): p. 396-407.

104. Brunner, M., et al., *In vivo gene transfer of Kv1.5 normalizes action potential duration and shortens QT interval in mice with long QT phenotype*. Am J Physiol Heart Circ Physiol, 2003. 285(1): p. H194-203.

105. Kodirov, S. A., et al., *Long-term restitution of 4-aminopyridine-sensitive currents in Kv1DN ventricular myocytes using adeno-associated virus-mediated delivery of Kv1.5*. FEBS Lett, 2003. 550(1-3): p. 74-8.

106. Brunner, M., et al., *Characterization of mice with a combined suppression of I(to) and I(K,slow)*. Am J Physiol Heart Circ Physiol, 2001. 281(3): p. H1201-9.

107. Mori, Y., E. Folco, and G. Koren, *GH3 cell-specific expression of Kv1.5 gene. Regulation by a silencer containing a dinucleotide repetitive element*. J Biol Chem, 1995. 270(46): p. 27788-96.

108. Valverde, P. and G. Koren, *Purification and preliminary characterization of a cardiac Kv1.5 repressor element binding factor*. Circ Res, 1999. 84(8): p. 937-44.

109. Landsman, D. and M. Bustin, *A signature for the HMG-1 box DNA-binding proteins*. Bioessays, 1993. 15(8): p. 539-46.

110. Ho, W. K., et al., *Voltage-and time-dependent block of delayed rectifier K+ current in rabbit sino-atrial node cells by external Ca2+ and Mg2+*. J Physiol, 1996.494: p. 727-42.

111. Paquette, T., et al., *Effects of divalent cations on the E-4031-sensitive repolarization current, I(Kr), in rabbit ventricular myocytes*. Biophys J, 1998. 74(3): p. 1278-85.

112. Johnson, J. P., Jr., F. M. Mullins, and P. B. Bennett, *Human ether-a-go-go-related gene K+ channel gating probed with extracellular ca2+. Evidence for two distinct voltage sensors*. J Gen Physiol, 1999. 113(4): p. 565-80.

113. Ho, W. K., et al., *Blockade of HERG channels expressed in Xenopus oocytes by external H+*. Pflugers Arch, 1999. 438(1): p. 23-9.

114. London, B., et al., *Two isoforms of the mouse ether-a-go-go-related gene coassemble to form channels with properties similar to the rapidly activating component of the cardiac delayed rectifier K+ current*. Circ Res, 1997. 81(5): p. 870-8.

115. Pond, A. L., et al., *Expression of distinct ERG proteins in rat, mouse, and human heart. Relation to functional I(Kr) channels*. J Biol Chem, 2000. 275(8): p. 5997-6006.

116. Pond, A. L. and J. M. Nerbonne, *ERG proteins and functional cardiac I(Kr) channels in rat, mouse, and human heart*. Trends Cardiovasc Med, 2001. 11(7): p. 286-94.

117. Ito, H. and K. Ono, *A rapidly activating delayed rectifier K+ channel in rabbit sinoatrial node cells*. Am J Physiol, 1995. 269(2): p. H443-52.

118. Matsuura, H., et al., *Rapidly and slowly activating components of delayed rectifier K(+) current in guinea-pig sino-atrial node pacemaker cells*. J Physiol, 2002. 540: p. 815-30.

119. Noma, A., et al., *Resting K conductances in pacemaker and non-pacemaker heart cells of the rabbit*. Jpn J Physiol, 1984. 34(2): p. 245-54.

120. Nathan, R. D., *Two electrophysiologically distinct types of cultured pacemaker cells from rabbit sinoatrial node*. Am J Physiol, 1986. 250(2): p. H325-9.

121. Wu, Y., D. M. Roden, and M. E. Anderson, *Calmodulin kinase inhibition prevents development of the arrhythmogenic transient inward current*. Circ Res, 1999. 84(8): p. 906-12.

122. Zygmunt, A. C., *Intracellular calcium activates a chloride current in canine ventricular myocytes*. Am J Physiol, 1994. 267(5 Pt 2): p. H1984-95.

123. Takei, M., et al., *The autonomic control of the transmural dispersion of ventricular repolarization in anesthetized dogs*. J Cardiovasc Electrophysiol, 1999. 10(7): p. 981-9.

124. Shimizu, W. and C. Antzelevitch, *Differential effects of beta-adrenergic agonists and antagonists in LQT1, LQT2 and LQT3 models of the long QT syndrome*. J Am Coll Cardiol, 2000. 35(3): p. 778-86.

125. Cheng, J., et al., *Heterogeneous distribution of the two components of delayed rectifier K+ current: a potential mechanism of the proarrhythmic effects of methanesulfonanilide class III agents*. Cardiovasc Res, 1999. 43(1): p. 135-47.

126. Choi, B. R., F. Burton, and G. Salama, *Cytosolic Ca2+ triggers early afterdepolarizations and Torsade de Pointes in rabbit hearts with type 2 long QT syndrome*. J Physiol, 2002. 543: p. 615-31.

127. Antzelevitch, C., et al., *Cellular and ionic mechanisms underlying erythromycin-induced long QT intervals and torsade de pointes*. J Am Coll Cardiol, 1996. 28(7): p. 1836-48.

128. Shimizu, W. and C. Antzelevitch, *Sodium channel block with mexiletine is effective in reducing dispersion of repolarization and preventing torsade des pointes in LQT2 and LQT3 models of the long-QT syndrome*. Circulation, 1997. 96(6): p. 2038-47.

129. Noda, T., et al., *Gene-specific response of dynamic ventricular repolarization to sympathetic stimulation in LQT1, LQT2 and LQT3 forms of congenital long QT syndrome*. Eur Heart J, 2002. 23(12): p. 975-83.

130. Antzelevitch, C., *Sympathetic modulation of the long QT syndrome*. Eur Heart J, 2002. 23(16): p. 1246-52.

131. Ali, R. H., et al., *Clinical and genetic variables associated with acute arousal and nonarousal-related cardiac events among subjects with long QT syndrome*. Am J Cardiol, 2000. 85(4): p. 457-61.

132. Schwartz, P. J., et al., *Genotype-phenotype correlation in the long-QT syndrome: gene-specific triggers for life-threatening arrhythmias*. Circulation, 2001. 103(1): p. 89-95.

133. Urao, N., et al., *Idiopathic long QT syndrome with early afterdepolarization induced by epinephrine*. A case report. Circ J, 2004. 68(6): p. 587-91.

134. Tateyama, M., et al., *Stimulation of protein kinase C inhibits bursting in disease-linked mutant human cardiac sodium channels*. Circulation, 2003. 107(25): p. 3216-22.

135. Thorneloe, K. S., et al., *Transmural differences in rat ventricular protein kinase C epsilon correlate with its functional regulation of a transient cardiac K+ current*. J Physiol, 2001. 533(Pt 1): p. 145-54.

136. Hu, K., D. Mochly-Rosen, and M. Boutjdir, *Evidence for functional role of epsilon PKC isozyme in the regulation of cardiac Ca(2+) channels*. Am J Physiol Heart Circ Physiol, 2000. 279(6): p. H2658-64.

137. Burashnikov, A. and C. Antzelevitch, *Differences in the electrophysiologic response of four canine ventricular cell types to alpha 1-adrenergic agonists*. Cardiovasc Res, 1999. 43(4): p. 901-8.

We claim:

1. A transgenic HERG or KvLQT1 dominant negative rabbit, whose genome comprises a mammalian cardiac β-MyHc promoter operably linked to the KvLQT1-Y315S or HERG-G628S cDNA sequence encoding a mutant form of the human cardiac ion channel protein KvLQT 1 (KCNQ 1) or HERG (KCNH2), wherein the mutant ion channel is overexpressed in the heart and the transgenic rabbit exhibits a longer QT interval than wild-type rabbits.

2. A cell isolated from the transgenic rabbit of claim 1.

3. A cell line derived from a cell of claim 2.

4. A method of making a transgenic rabbit of claim 1, said method comprising the steps of: introducing into a zygote a nucleic acid construct comprising a mammalian cardiac β-MyHC promoter operably linked to the KvLQT1-Y315S or HERG-G628S cDNA sequences encoding a mutant form of the human cardiac ion channel protein KvLQT 1 (KCNQ 1) or HERG (KCNH2); allowing said zygote to develop to term; obtaining a rabbit whose genome comprises the nucleic acid construct; breeding said rabbit with a non-transgenic rabbit to obtain $F_1$ offspring and selecting a rabbit whose genome comprises the nucleic acid construct, wherein said rabbit expresses the mutant human cardiac ion channel protein and exhibits a longer QT interval than wild-type rabbits.

* * * * *